US009267945B2

(12) United States Patent
Weiner et al.

(10) Patent No.: US 9,267,945 B2
(45) Date of Patent: Feb. 23, 2016

(54) DIAGNOSIS OF MULTIPLE SCLEROSIS

(75) Inventors: Howard L. Weiner, Brookline, MA (US); Irun R. Cohen, Rehovot (IL); Francisco J. Quintana, Buenos Aires (AR)

(73) Assignees: Yeda Research and Development Co. Ltd., Rehovot (IL); The Brigham and Women's Hospital, Boston, MA (US)

( * ) Notice: Subject to any disclaimer, the term of this patent is extended or adjusted under 35 U.S.C. 154(b) by 905 days.

(21) Appl. No.: 13/128,862

(22) PCT Filed: Nov. 12, 2009

(86) PCT No.: PCT/IL2009/001066
§ 371 (c)(1),
(2), (4) Date: Dec. 16, 2011

(87) PCT Pub. No.: WO2010/055510
PCT Pub. Date: May 20, 2010

(65) Prior Publication Data
US 2012/0077686 A1  Mar. 29, 2012

Related U.S. Application Data

(60) Provisional application No. 61/113,645, filed on Nov. 12, 2008.

(51) Int. Cl.
*G01N 33/564* (2006.01)

(52) U.S. Cl.
CPC ........ *G01N 33/564* (2013.01); *G01N 2800/285* (2013.01)

(58) Field of Classification Search
None
See application file for complete search history.

(56) References Cited

U.S. PATENT DOCUMENTS

| | | | |
|---|---|---|---|
| 7,785,819 B2 | 8/2010 | Robinson | |
| 2003/0092089 A1 | 5/2003 | Moscarello | |
| 2004/0014069 A1* | 1/2004 | Cohen et al. | 435/6 |
| 2005/0009096 A1 | 1/2005 | Genain | |
| 2005/0260770 A1 | 11/2005 | Cohen | |
| 2006/0089302 A1 | 4/2006 | Abulafia-Lapid | |
| 2007/0020691 A1* | 1/2007 | Kanter et al. | 435/7.1 |
| 2008/0193440 A1 | 8/2008 | Jensen | |

FOREIGN PATENT DOCUMENTS

| | | |
|---|---|---|
| WO | 02/08755 A2 | 1/2002 |
| WO | 02/067760 A2 | 9/2002 |
| WO | 2006/077126 A2 | 7/2006 |
| WO | 2006/088833 A2 | 8/2006 |
| WO | 2006/117689 A2 | 11/2006 |
| WO | WO2006116155 | * 11/2006 |
| WO | 2007/056332 A2 | 5/2007 |
| WO | 2007/137410 A1 | 12/2007 |
| WO | 2008/125651 A2 | 10/2008 |

OTHER PUBLICATIONS

Lily et al., Brain (2004), 127, 269-279.*
Annunziata et al., Early synthesis and correlation of serum anti-thyroid antibodies with clinical parameters in multiple sclerosis. J Neurol Sci. 1999; 168:32-6.
Archelos et al., The role of B cells and autoantibodies in multiple sclerosis. Ann Neurol. 2000; 47:694-706.
Barned et al., Frequency of anti-nuclear antibodies in multiple sclerosis. Neurology 1995; 45:384-5.
Bitsch and Brück, Differentiation of multiple sclerosis subtypes: implications for treatment. CNS Drugs 2002; 16 (6):405-18.
Cepok et al., Identification of Epstein-Barr virus proteins as putative targets of the immune response in multiple sclerosis. J Clin Invest. 2005; 115:1352-60.
Cohen, Real and artificial immune systems: computing the state of the body. Nat Rev Immunol. 2007; 7:569-74.
Colaco et al., Anti-cardiolipin antibodies in neurological disorders: cross-reaction with anti-single stranded DNA activity. Clin Exp Immunol. 1987; 68:313-9.
Dalakas, B cells in the pathophysiology of autoimmune neurological disorders: a credible therapeutic arget. Pharmacol Ther. 2006; 112:57-70.
Genain et al., Identification of autoantibodies associated with myelin damage in multiple sclerosis. Nat Med. 1999; 5:170-5.
Jihui et al., Clinical Analysis of Complications of Multiple Sclerosis patients. Chinese Journal for Clinicians. 2007; 35 (10) 28-9—Translated abstract.
Kanter et al., Lipid microarrays identify key mediators of autoimmune brain inflammation. Nat Med 2006; 12:138-43.
Keegan et al., Relation between humoral pathological changes in multiple sclerosis and response to therapeutic plasma exchange. Lancet 2005; 366:579-82.
Lalive et al., Antibodies to native myelin oligodendrocyte glycoprotein are serologic markers of early inflammation in multiple sclerosis. Proc Natl Acad Sci US. 2006; 103;2280-5.
Lassmann et al., The immunopathology of multiple sclerosis: an overview. Brain Pathol. 2007; 17(2): 210-8.
Lefran et al., Distortion of the Self-Reactive IgG Antibody Repertoire in Multiple Sclerosis as a New Diagnostic Tool. J Immunol. 2004; 172: 669-78.
Li et al., Identification of autoantibody clusters that best predict lupus disease activity using glomerular proteome arrays. J Clin Invest. 2005; 115:3428-39.
Lim et al., Anti-myelin antibodies do not allow earlier diagnosis of multiple sclerosis. Mult Scler. 2005; 11:492-4.
Lorenz et al., Probing the epitope signatures of IgG antibodies in human serum from patients with autoimmune disease. Methods Mol Biol. 2009; 524:247-58.

(Continued)

*Primary Examiner* — John Ulm
(74) *Attorney, Agent, or Firm* — Rodney J. Fuller; Booth Udall Fuller, PLC

(57) ABSTRACT

The present invention relates to methods and kits for diagnosing multiple sclerosis (MS) in a subject. Particularly, the present invention relates to methods and kits for diagnosing a subtype of MS in a subject, the subtype selected from relapsing-remitting MS (RRMS), secondary progressive MS (SPMS), primary progressive MS (PPMS) and a pathologic sub-type of MS lesions selected from Pattern I and Pattern II MS lesion.

16 Claims, 12 Drawing Sheets

(56) References Cited

OTHER PUBLICATIONS

Lucchinetti et al., Evidence for pathogenic heterogeneity in multiple sclerosis. Ann Neurol 2004; 56(2):308.

Lucchinetti et al., Heterogeneity of multiple sclerosis lesions: implications for the pathogenesis of demyelination. Ann Neurol. 2000; 47:707-17.

Meinl et al., B lineage cells in the inflammatory central nervous system environment: migration, maintenance, local antibody production, and therapeutic modulation. Ann Neurol. 2006; 59:880-92.

Merbl et al., Newborn humans manifest autoantibodies to defined self molecules detected by antigen microarray informatics. J Clin Invest 2007; 117(3):712-8.

Miller and Leary, Primary-progressive multiple sclerosis. Lancet Neurol. 2007; 6:903-12.

O'Connor et al., Self-antigen tetramers discriminate between myelin autoantibodies to native or denatured protein. Nat Med. 2007; 13(2):211.

Gusman et al., Protective and therapeutic role for alphaB-crystallin in autoimmune demyelination. Nature 2007; 448:474-9.

Ponmarenko et al., Autoantibodies to myelin basic protein catalyze site-specific degradation of their antigen. Proc Natl Acad Sci US. 2006; 103:281-6.

Poser, Revisions to the 2001 McDonald diagnostic criteria. Ann Neurol. 2006; 59(4):727-8.

Quintana and Cohen, Autoantibody patterns in diabetes-prone NOD mice and in standard C57BL/6 mice. J Autoimmun. 2001; 17:191-7.

Quintana et al., Cluster analysis of human autoantibody reactivities in health and in type 1 diabetes mellitus: a bio-informatic approach to immune complexity. J Autoimmun. 2003; 21:65-75.

Quintana et al., Functional immunomics: microarray analysis of IgG autoantibody repertoires predicts the future response of mice to induced diabetes. Proc Natl Acad Sci. 2004; 101(suppl 2):14615-21.

Quintana et al., Antigen-chip technology for accessing global information about the state of the body. Lupus 2006; 15:428-30.

Quintana et al., Antigen microarrays identify unique serum autoantibody signatures in clinical and pathologic subtypes of multiple sclerosis. Proc Nat Acad Sci. 2008; 105:18889-94.

Rinaldi and Gallo, Immunological markers in multiple sclerosis: tackling the missing elements. Neurol Sci. 2005; 26: S215-7.

Robinson et al., Autoantigen microarrays for multiplex characterization of autoantibody responses. Nat Med. 2002; 8:295-301.

Robinson et al., Protein microarrays guide tolerizing DNA vaccine treatment of autoimmune encephalomyelitis. Nat Biotechnol. 2003; 21:1033-9.

Roussel et al., Prevalence and clinical significance of anti-phospholipid antibodies in multiple sclerosis: a study of 89 patients. J Autoimmun. 2000; 14:259-65.

Silber et al., Patients with progressive multiple sclerosis have elevated antibodies to neurofilament subunit. Neurology. 2002; 58(9):1372-81.

Spadaro et al., Autoimmunity in multiple sclerosis: study of a wide spectrum of autoantibodies. Mult Scler J. 1999; 5:121-5.

Wucherpfennig et al., Recognition of the immunodominant myelin basic protein peptide by autoantibodies and HLA-DR2-restricted T cell clones from multiple sclerosis patients. Identity of key contact residues in the B-cell and T-cell epitopes. J Clin Invest. 1997; 100:1114-22.

Zhen et al., Identification of autoantibody clusters that best predict lupus disease activity using glomerular proteome arrays. The Journal of Clinical Investigation. 2005; 115(12): 3428-39.

Zhou et al., Identification of a pathogenic antibody response to native myelin oligodendrocyte glycoprotein in multiple sclerosis. Proc Natl Acad Sci US. 2006; 103:19057-62.

* cited by examiner

DIAGNOSIS OF MULTIPLE SCLEROSIS

RELATED APPLICATION DATA

This application is the U.S. National Stage of PCT/IL2009/001066, filed Nov. 12, 2009, which claims the benefit of U.S. Provisional Patent Application No. 61/113,645, filed Nov. 12, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 96,669 byte ASCII (text) file named "Seq_List" created on May 11, 2011.

FIELD OF THE INVENTION

The present invention relates to methods and kits for diagnosing multiple sclerosis (MS) in a subject. Particularly, the present invention relates to methods and kits for diagnosing a subtype of MS in a subject, the subtype selected from relapsing-remitting MS (RRMS), secondary progressive MS (SPMS), primary progressive MS (PPMS) and a pathologic sub-type of MS lesions selected from Pattern I and Pattern II MS lesion.

BACKGROUND OF THE INVENTION

Multiple sclerosis (MS) is a chronic inflammatory disease of the central nervous system (CNS) of presumed autoimmune etiology. MS is characterized by focal lesions (plaques) in the brain and spinal cord leading to progressive neurological dysfunction. The etiology of MS is unknown, but it is thought to result from a combination of genetic and environmental factors. Currently, there is no specific test for diagnosing MS and the diagnosis relies on recognition of the clinical history of the subject. The diagnosis can be supported by MRI of the brain and spinal cord, analysis of the cerebrospinal fluid, and evoked potential studies of the visual and somatosensory pathways. In addition, systemic or infectious etiologies with similar presentation must be excluded. Multiple sclerosis may progress and regress unpredictably; however, there are several patterns of symptoms. Approximately 85-90% of patients begin with a relapsing-remitting (RRMS) course and 40% eventually become progressive (secondary progressive MS, SPMS); in 10%, MS presents a primary progressive course (PPMS). The different MS subtypes are characterized by the past course of the disease (e.g. unpredictable relapses, remissions and progression of neurologic decline). From a clinical perspective, patients with different disease courses show different treatment responses. For instance, patients with relapsing-remitting MS are more likely to respond to immunomodulatory therapy than those with a progressive disease course (Bitsch and Bruck, CNS Drugs, 2002; 16(6):405-18). Thus, characterizing the MS subtype is important not only for prognosis but also for therapeutic decisions.

MS is not only heterogeneous in its clinical symptoms and rate of progression, but also in its response to therapy and histopathological findings (Lucchinetti et al., 2000, Ann Neurol 47, 707-17). The pattern of active demyelination is identical among multiple lesions examined from a given MS patient, yet heterogeneous between patients, suggesting pathogenic heterogeneity. Pattern I is characterized by T-cell/macrophage-mediated demyelination. Pattern II is characterized by antibody/complement-associated demyelination. Pattern III is defined by a distal oligodendrogliopathy, and pattern IV is characterized by oligodendrocyte degeneration in the periplaque white matter; to date pattern IV has only been identified in autopsy cases. Patterns I and II lesions show the typical perivenous distribution and sharp borders that are the pathological hallmarks of MS lesions and are thought to result from classical autoimmune mechanisms (Lucchinetti, et al., 2004, Ann Neurol 56, 308). MRI is commonly used to visualize MS lesions in vivo. The use of MRI to study MS lesions is limited, however, because it cannot provide information about the pathological composition of the lesions. From a clinical standpoint patients with Pattern II, but not Pattern I, have been reported to respond to plasmapheresis (Keegan et al., 2005, Lancet 366, 579-82). Thus, there is a need for identifying patients that would be responsive to treatment with plasmapheresis.

The McDonald criteria was introduced in 2001, and revised in 2005 (Polman et al., 2006, Ann Neurol.; 59(4):727-8), as guidelines to facilitate early and accurate diagnosis of multiple sclerosis (MS). Diagnostic classifications are reduced to a) having MS, b) not having MS, or c) having possible MS. Advantages to the Criteria include the capability of making a definitive diagnosis of MS either after a monosymptomatic presentation or in the context of a primary progressive course. However, the diagnostic classification scheme and MRI criteria remain complicated and tedious, and this complexity limits their use in everyday practice. Furthermore, the specificity of these criteria is relatively low, emphasizing the importance of clinical judgment in excluding other diagnoses. In addition, studies have observed that standard MS disease-modifying medications can benefit patients who do not yet fulfill these diagnostic criteria. Finally, the McDonald criteria decreased the time required for MS diagnosis substantially, however it is still limited for those individuals who are diagnosed with possible MS, or those who will eventually receive a diagnosis of PPMS.

Although MS is considered a T cell mediated disease, several pieces of evidence support a role for B cells in the disease (Archelos et al., 2000, Ann Neurol. 47, 694-706). B cells can contribute to MS progression by their secretion of antibodies and cytokines, or by acting as antigen presenting cells (APC) to activate pathogenic T cells. B cells are significantly more efficient in processing and presenting antigens recognized by the antibodies they produce. Thus, it is not surprising that linear B and T cell epitopes are co-localized in CNS antigens targeted by the autoimmune response in human and experimental models of MS (Meinl et al., 2006, Ann Neurol. 59, 880-92; Wucherpfennig et al., 1997, J Clin Invest. 100, 1114-22).

Immune System Biomarkers

The immune system in both its innate and adaptive arms can be viewed as a type of biological health-maintenance system. In physiological terms, the cells and molecules comprising the immune system are considered to act to manage inflammation (Cohen, 2000, Academic Press, London). Inflammation is classically defined as the collective processes activated by injury that lead to healing. The immune system, by the way it initiates and manages inflammation, maintains the body by healing wounds, containing pathogens, organizing the structure of connective tissue, growing (angiogenesis) or destroying blood vessels, triggering regeneration of certain organs, activating the apoptosis of aged cells and those with irreparable DNA damage, degrading accumulations of abnormal molecules, disposing of waste, and performing other vital activities (Cohen, 2000). These varied expressions of inflammation maintain the integrity of the organism in response to its relentless post-developmental decomposition due to neoplasia, environmental injuries and infections, accumulations of metabolic products, waste, and other intoxications, and the inexorable advance of entropy.

The possibility that cerebrospinal fluid (CSF) antibodies in MS patients are generated as a response to myelin self-antigens has been investigated in detail. Antibodies reactive with several CNS antigens have been described, including those directed against myelin oligodendrocyte glycoprotein (MOG), oligodendrocyte-specific protein (OSP), myelin basic protein (MBP), proteolipid protein (PLP), myelin associated glycoprotein, 2',3'-cyclic nucleotide 3' phosphodiesterase (CNPase) and ab-crystallin. When analyzed, the subclasses of these antibodies correlated with a pro-inflammatory immune response. Many of these autoantibodies have been detected also in blood (Lalive et al., 2006, *Proc Natl Acad Sci US.* 103, 2280-5). In addition, higher titers of antibodies reactive with non myelin autoantigens (Annunziata et al., 1999, *J Neurol Sci.* 168, 32-6; Barned et al., 1995, *Neurology.* 45, 384-5; Colaco et al., 1987, *Clin Exp Immunol.* 68, 313-9; Roussel et al., 2000, *J Autoimmun.* 14, 259-65; Spadaro et al., 1999, *Mult Scler.* 5, 121-5) and to pathogens (Cepok et al., 2005, *J Clin Invest.* 115, 1352-60) have been also found in MS patients.

The role played by antibodies in MS still awaits further clarification. Antibodies to conformational epitopes in MOG have been purified from MS lesions and shown to alter the physiology of CNS cells (Lalive et al., 2006). Accordingly, U.S. Pat. App. Pub. No. 2005/0009096 provides methods utilizing detection or quantification of autoantibodies to specific epitopes of myelin/MOG components for diagnosis or prognosis of MS.

Antibodies reactive with linear epitopes in CNS antigens have also been isolated from MS lesions (Dalakas, 2006, *Pharmacol Ther.* 112, 57-70; Genain et al., 1999, *Nat. Med.* 5, 170-5), suggesting that they also play a direct role in MS pathology. Moreover, antibodies to MBP isolated from MS patients have been shown to have direct proteolytic activity (Ponmarenko et al., 2006, *Proc Natl Acad Sci US.* 103, 281-6). U.S. Pat. App. Pub. No. 2003/0092089 relates to an assay for detecting MBP autoantibodies, and alternatively in conjunction with the measurement of other biochemical markers associated with MS and related diseases.

Biomarkers are anatomic, physiologic, biochemical or molecular parameters associated to specific disease states. The search for MS biomarkers has been focused on indicators of the general activity of the inflammatory process. Several biomarkers aim at following not the inflammatory process itself, but its consequences such us neurodegeneration and axonal loss. Thus, altered levels of neurofilament light chains, tau and 14-3-3 protein have been described to correlate with axonal loss in MS patients.

Since MS is felt to be an organ specific autoimmune disorder, immune biomarkers have the potential to reflect disease activity and its response to therapy. Several large-scale proteomic studies have attempted the characterization of antibodies in CSF and serum, aiming to identify yet unknown targets of the autoimmune attack in MS patients (Lefran et al., 2004, *J Immunol* 172, 669-78). Moreover, specific antibodies have been investigated as biomarkers in MS, resulting in the identification of several up-regulated antibody responses to myelin antigens in CSF and/or serum. However, these biomarkers were not generalizable to the majority of MS patients or could not be validated in independent studies (Rinaldi and Gallo, 2005, *Neurol Sci.* 26, S215-7; Lim et al., 2005, *Mult Scler.* 11, 492-4). Similarly to what has been observed in other autoimmune diseases such as diabetes (Quintana et al., 2004, *Proc Natl Acad Sci,* 14615-21) and systemic lupus erythematosus (Li et al., 2005, *J Clin Invest.* 115, 3428-39), it is possible that no single biomarker will be conclusive, but rather a pattern of several biomarkers forming a fingerprint will be required.

The Antigen Chip

Antigen microarrays are newly developed tools for the high-throughput characterization of the immune response (Robinson et al., 2002, *Nat Med* 8, 295-301), and have been used to analyze immune responses in vaccination and in autoimmune disorders (Robinson et al., 2002; Robinson et al., 2003, *Nat. Biotechnol.* 21, 1033-9; Quintana et al., 2004; Kanter et al., 2006, *Nat Med* 12, 138-43). It has been hypothesized, that patterns of multiple reactivities may be more revealing than single antigen-antibody relationships (Quintana et al., 2006, *Lupus* 15, 428-30) as shown in previous analyses of autoimmune repertoires of mice (Quintana et al., 2004; Quintana et al., 2001, *J Autoimmun* 17, 191-7) and humans (Merbl et al., 2007, *J Clin Invest* 117, 712-8; Quintana et al., 2003, *J Autoimmun* 21, 65-75) in health and disease. Thus, autoantibody repertoires have the potential to provide both new insights into the pathogenesis of the disease and to serve as immune biomarkers (Cohen, 2007, *Nat Rev Immunol.* 7, 569-74) of the disease process.

Antigen microarrays have been used to characterize serum autoantibodies in systemic lupus erythematosus, rheumatoid arthritis and neuromyelitis optica. However, high-affinity specific antibodies in MS have not been reported with any regularity in serum (Meinl et al., 2006, *Ann Neurol.* 59, 880-92; O'Connor et al., 2007, *Nat Med* 12, 12; Zhou et al., 2006, *Proc Natl Acad Sci US.* 103, 19057-62). In contrast to autoantibodies in serum, Kanter and associates have used microarrays to detect lipid (Kanter et al., 2006) and αB-crystallin (Ousman et al., 2007, *Nature.* 448, 474-9) reactive antibodies in the CSF. Strikingly, the antibodies to αB-crystallin were of low affinity, detectable at 1:20 dilution (Ousman et al., 2007).

PCT Pub. No. WO 02/08755 to some of the inventors of the present invention is directed to a method, system and an article of manufacture for clustering and thereby identifying predefined antigens reactive with undetermined immunoglobulins of sera derived from patient subjects in need of diagnosis of disease or monitoring of treatment. The '755 publication discloses the use of antigen arrays for identifying antigens reactive with immunoglobulins of sera derived from subjects afflicted with various diseases. Further disclosed are diagnostic methods, and systems useful in these methods, employing the step of clustering a subset of antigens of a plurality of antigens, said subset of antigens being reactive with a plurality of antibodies being derived from a plurality of patients having an impaired immune system and suffering from a disease, and associating or deassociating the antibodies of a subject with the resulting cluster. While WO 02/08755 discloses methods useful in diagnosis of MS among other autoimmune diseases, there is no disclosure of diagnosing different subtypes of MS or monitoring MS progression.

U.S. Pat. App. Pub. No. 2005/0260770 to some of the inventors of the present invention discloses an antigen array system and diagnostic uses thereof. The application provides a method of diagnosing an immune disease, and particularly type 1 diabetes, or a predisposition thereto in a subject, comprising determining a capacity of immunoglobulins of the subject to specifically bind each antigen probe of an antigen probe set. The antigen probe set comprises a plurality of antigen probes selected from the group consisting of at least a portion of a cell/tissue structure molecule, at least a portion of a heat shock protein, at least a portion of an immune system molecule, at least a portion of a homopolymeric polypeptide, at least a portion of a hormone, at least a portion of a metabolic enzyme, at least a portion of a microbial antigen, at least a portion of a molluscan antigen, at least a portion of a nucleic acid, at least a portion of a plant antigen, at least a portion of a plasma molecule, and at least a portion of a tissue antigen, wherein the binding capacity of the immunoglobulin of the subject is indicative of the immune disease or the predisposition thereto. However, none of the prior art discloses an antigen array that can provide a specific, reliable, accurate and discriminatory assay for diagnosing MS, specifically for discriminating between different subtypes of MS and predicting or monitoring disease progression. Such discriminatory assays would be highly valuable in tailoring adequate therapeutic approach for each patient.

PCT Pub. No. WO 07/137,410 relates to methods for the diagnosis MS, different forms of MS or another demyelinating disorder. Particularly, WO 07/137,410 relates to specific metabolites, identified by their molecular masses, found to have different abundances or intensities between clinically diagnosed MS or other neurological disorders, and normal patients. Nevertheless, WO 07/137,410 does not disclose nor mention the use of testing an antibody reactivity pattern for identifying unique signature patterns in different subtypes of MS, and to further differentiate between patients having MS and those afflicted with other neurological disorders.

Thus, there remains a need for improved diagnostic methods and kits useful in diagnosing MS and particularly, diagnosing subtypes of MS in a subject.

SUMMARY OF THE INVENTION

The present invention provides methods and kits for diagnosing multiple sclerosis (MS) in a subject, antigen probe arrays for practicing such a diagnosis, and antigen probe sets for generating such arrays. Particularly, the present invention provides methods and kits for diagnosing a subtype of MS in a subject, wherein the subtype of MS is selected from relapsing-remitting MS (RRMS), secondary progressive MS (SPMS), primary progressive MS (PPMS) and a pathologic sub-type of MS lesions selected from Pattern I and Pattern II MS lesion.

The present invention is based in part on the unexpected results obtained when testing the antibody reactivity of MS patients using an antigen array. The analysis resulted in the identification of unique signature patterns of autoantibody reactivities. It is now disclosed for the first time that unique autoantibody signature patterns characterize sub-types of MS, namely relapsing-remitting MS (RRMS), secondary progressive MS (SPMS) and primary progressive MS (PPMS) based on reactivity to central nerve system (CNS) antigens, heat shock proteins (HSP) and lipid antigens. Strikingly, the unique autoantibody signature patterns distinguished the MS subtype from other neurologic or autoimmune driven diseases including Alzheimer's disease (AD), adrenoleukodystrophy (ALD) and lupus erythematosus. It is further disclosed that unique autoantibody signature patterns characterize different immunopathologic patterns of MS lesions, based on the reactivity to lipids and CNS-derived peptides, thus providing for the first time a biomarker-based assay for sub-typing MS classes and stages.

Thus, the present invention relates to methods and kits for the diagnosis of a subtype of MS. According to the principles of the invention the kits comprise a plurality of antigens also referred to herein as antigen probe sets. These antigen probe sets comprising a plurality of antigens are reactive specifically with the sera of subjects having MS. According to the principles of the invention, the plurality of antigens may advantageously be used in the form of an antigen array. According to some embodiments the antigen array is conveniently arranged in the form of an antigen chip.

The present invention identifies clusters of antigens relevant to subtypes of MS and defines the reactivity observed with test sera versus control sera. While no single antigen was identified that was sufficient on its own to adequately diagnose a subject with MS or a subtype of MS, specific combinations of these antigens, as detailed in Table 1 to 4 herein below, were significantly more accurate and reliable in discriminating patients and control subjects than each antigen alone. Table 1, as detailed below, contains SEQ ID NOS: 7, 14, 23-83 and 98-100, fragments derived from SEQ ID NOS: 4-6, 10 and 12, and the non-peptide moiety lactocerebroside. Table 2, as detailed below, contains SEQ ID NOS: 7, 8, 13, 16, 22, 29, 42, 51, 60, 67-71 84, 85 and 101, fragments derived from SEQ ID NOS: 4-6, 9, 10, 12 and 20, and the non-peptide moieties *S. minnesota* LPS, *E. coli* LPS and chondroitin 4-sulfate. Table 3, as detailed below, contains SEQ ID NOS: 6, 7, 19, 21, 25, 26, 28, 29, 31, 32, 35-38, 40-42, 44, 48, 53, 55, 56, 64, 70, 73, 75, 85-96, 100, 102 and 103, fragments derived from SEQ ID NOS: 4-6, 10, 12 and 15, and the non-peptide moieties asialoganglioside-GM2, cardiolipin and cholesterol. Table 4, as detailed below, contains SEQ ID NOS: 17, 29, 43, 85 and 97, fragments derived from SEQ ID NOS: 5 and 12, and the non-peptide moieties: 15-ketocholestane, 15α-hydroxycholestene, Ganglioside-GM4, 15-ketocholestene, Tetrasialoganglioside-GQ1B, Brain L-α-lysophosphatidylserine and Lactosylceramide.

TABLE 1

Antigens Discriminating RRMS and healthy controls (HC)

| Antigen | Type | Sequence/SEQ ID NO: |
|---|---|---|
| MBP 31-50 | peptide | derived from SEQ ID NO: 6 |
| HSP70 481-500 | peptide | ANGILNVTATDKSTGKANKI (SEQ ID NO: 23) |
| PLP 65-84 | peptide | derived from SEQ ID NO: 12 |
| GFAP | protein | SEQ ID NO: 14 |
| HSP70 511-530 | peptide | KEEIERMVQEAEKYKAEDEV (SEQ ID NO: 24) |
| MBP 41-60 | peptide | derived from SEQ ID NO: 6 |
| HSP60 286-305 | peptide | LVLNRLKVGLQVVAVKAPGF (SEQ ID NO: 25) |

TABLE 1-continued

Antigens Discriminating RRMS and healthy controls (HC)

| Antigen | Type | Sequence/SEQ ID NO: |
| --- | --- | --- |
| HSP60 496-515 | peptide | QSSSEVGYDAMAGDFVNMVE (SEQ ID NO: 26) |
| HSP70 151-170 | peptide | NDSQRQATKDAGVIAGLNVL (SEQ ID NO: 27) |
| HSP60 526-545 | peptide | RTALLDAAGVASLLTTAEVV (SEQ ID NO: 28) |
| MBP 11-30 | peptide | derived from SEQ ID NO: 6 |
| OSP 61-80 | peptide | GLYHCKPLVDILILPGYVQA (SEQ ID NO: 29) |
| HSP70 31-50 | peptide | NDQGNRTTPSYVAFTDTERL (SEQ ID NO: 30) |
| CNP 286-305 | peptide | ISALFVTPKTTGARVELSEG (SEQ ID NO: 31) |
| HSP60 255-275 | peptide | QSIVPALEIANAHRKPLVIIA (SEQ ID NO: 32) |
| HSP60 106-125 | peptide | NEEAGDGTTTATVLARSIAK (SEQ ID NO: 33) |
| OSP 31-50 | peptide | VVTCGYTIPTCRKLDELGSK (SEQ ID NO: 34) |
| P2 61-80 | peptide | derived from SEQ ID NO: 10 |
| MBP 84-94 | peptide | derived from SEQ ID NO: 6 |
| HSP60 376-395 | peptide | EQLDVTTSEYEKEKLNERLA (SEQ ID NO: 35) |
| HSP70 286-305 | peptide | SLFEGIDFYTSITRARFEEL (SEQ ID NO: 36) |
| HSP60 136-155 | peptide | NPVEIRRGVMLAVDAVIAEL (SEQ ID NO: 37) |
| HSP70 136-155 | peptide | GYPVTNAVITVPAYFNDSQR (SEQ ID NO: 38) |
| P2 46-65 | peptide | derived from SEQ ID NO: 10 |
| OSP 136-155 | peptide | VATIWFPVCAHRETTIVSFG (SEQ ID NO: 39) |
| P2 1-20 | peptide | derived from SEQ ID NO: 10 |
| MOG 91-110 | peptide | derived from SEQ ID NO: 5 |
| HSP60 361-380 | peptide | KGDKAQIEKRIQEIIEQLDV (SEQ ID NO: 40) |
| HSP70 451-470 | peptide | KDNNLLGRFELSGIPPAPGV (SEQ ID NO: 41) |
| HSP70 210-229 | peptide | TIDDGIFEVKATAGDTHLGG (SEQ ID NO: 42) |
| HSP60 240-259 | peptide | QDAYVLLSEKKISSIQSIVP (SEQ ID NO: 43) |
| HSP60 271-290 | peptide | LVIIAEDVDGEALSTLVLNR (SEQ ID NO: 44) |
| OSP 76-95 | peptide | GYVQACRALMIAASVLGLPA (SEQ ID NO: 45) |
| PLP 178-191 | peptide | derived from SEQ ID NO: 12 |
| CNP 271-290 | peptide | QDVLKKSYSKAFTLTISALF (SEQ ID NO: 46) |
| P2 76-95 | peptide | derived from SEQ ID NO: 10 |
| HSP70 631-640 | peptide | GSGPTIEEVD (SEQ ID NO: 47) |
| PLP 248-259 | peptide | derived from SEQ ID NO: 12 |
| HSP60 195-214 | peptide | RKGVITVKDGKTLNDELEII (SEQ ID NO: 48) |
| CNP 61-80 | peptide | SGKSTLARVIVDKYRDGTKM (SEQ ID NO: 49) |
| MOG 196-215 | peptide | derived from SEQ ID NO: 5 |
| HSP60 46-65 | peptide | LLADAVAVTMGPKGRTVIIE (SEQ ID NO: 50) |
| HSP70 195-214 | peptide | LIFDLGGGTFDVSILTIDDG (SEQ ID NO: 51) |
| HSP70 436-455 | peptide | PGVLIQVYEGERAMTKDNNL (SEQ ID NO: 52) |
| HSP60 166-185 | peptide | EEIAQVATISANGDKEIGNI (SEQ ID NO: 53) |

TABLE 1-continued

Antigens Discriminating RRMS and healthy controls (HC)

| Antigen | Type | Sequence/SEQ ID NO: |
|---|---|---|
| MBP 104-123 | peptide | derived from SEQ ID NO: 6 |
| MBP 71-92 | peptide | derived from SEQ ID NO: 6 |
| PLP 180-199 | peptide | derived from SEQ ID NO: 12 |
| HSP70 255-275 | peptide | NKRAVRRLRTACERAKRTLS (SEQ ID NO: 54) |
| MOBP 166-185 | peptide | derived from SEQ ID NO: 4 |
| CNP 240-259 | peptide | YFGKRPPGVLHCTTKFCDYG (SEQ ID NO: 55) |
| HSP60 16-35 | peptide | RVLAPHLTRAYAKDVKFGAD (SEQ ID NO: 56) |
| HSP60 301-320 | peptide | KAPGFGDNRKNQLKDMAIAT (SEQ ID NO: 57) |
| MOBP 151-170 | peptide | derived from SEQ ID NO: 4 |
| CNP 91-110 | peptide | GARGAFSEEYKRLDEDLAAY (SEQ ID NO: 58) |
| HSP70 106-125 | peptide | SYKGETKAFYPEEISSMVLT (SEQ ID NO: 59) |
| CNP 406-421 | peptide | TQGSRKGGALQSCTII (SEQ ID NO: 60) |
| HSP60 421-440 | peptide | VTDALNATRAAVEEGIVLGG (SEQ ID NO: 61) |
| HSP60 61-80 | peptide | TVIIEQSWGSPKVTKDGVTV (SEQ ID NO: 62) |
| AB10-20 | peptide | YEVHHQKLVFF (SEQ ID NO: 98) |
| HSP60 511-530 | peptide | VNMVEKGIIDPTKVVRTALL (SEQ ID NO: 63) |
| LACTOCEREBROSIDE | lipid | PubChem Subtance ID: 24892591 |
| HSP70 406-425 | peptide | AGGVMTALIKRNSTIPTKQT (SEQ ID NO: 64) |
| MOG 76-95 | peptide | derived from SEQ ID NO: 5 |
| HSP70 316-335 | peptide | PVEKALRDAKLDKAQIHDLV (SEQ ID NO: 65) |
| HSP60 225-244 | peptide | SPYFINTSKGQKCEFQDAYV (SEQ ID NO: 66) |
| HSP60 76-95 | peptide | DGVTVAKSIDLKDYKNIGA (SEQ ID NO: 67) |
| MOG 106-125 | peptide | derived from SEQ ID NO: 5 |
| HSP70 466-485 | peptide | PAPGVPQIEVTFDIDANGIL (SEQ ID NO: 68) |
| CNP 1-20 | peptide | MNRGFSRKSHTFLPKIFFRK (SEQ ID NO: 69) |
| HSP70 166-185 | peptide | GLNVLRIINEPTAAAIAYGL (SEQ ID NO: 70) |
| HSP70 121-140 | peptide | SMVLTKMKEIAEAYLGYPVT (SEQ ID NO: 71) |
| AB1-42 | peptide | DAEFRHDSGYEVHHQKLVFFAEDVGSNKGAIIGL MVGGVVIA (SEQ ID NO: 99) |
| MBP 89-101 | peptide | derived from SEQ ID NO: 6 |
| CNP 301-320 | peptide | ELSEQQLQLWPSDVDKLSPT (SEQ ID NO: 72) |
| HSP70 1-20 | peptide | MAKAAAVGIDLGTTYSCVGV (SEQ ID NO: 73) |
| MBP 51-70 | peptide | derived from SEQ ID NO: 6 |
| HSP70 496-515 | peptide | KANKITITNDKGRLSKEEIE (SEQ ID NO: 74) |
| CNP 16-35 | peptide | IFFRKMSSSGAKDKPELQFP (SEQ ID NO: 75) |
| CNP 76-95 | peptide | DGTKMVSADAYKITPGARGA (SEQ ID NO: 76) |
| PLP 10-29 | peptide | derived from SEQ ID NO: 12 |
| PLP 190-209 | peptide | derived from SEQ ID NO: 12 |
| HSP60 346-365 | peptide | GEVIVTKDDAMLLKGKGDKA (SEQ ID NO: 77) |

TABLE 1-continued

Antigens Discriminating RRMS and healthy controls (HC)

| Antigen | Type | Sequence/SEQ ID NO: |
|---|---|---|
| HSP60 151-170 | peptide | VIAELKKQSKPVTTPEEIAQ (SEQ ID NO: 78) |
| HSP70 376-395 | peptide | QAAILMGDKSENVQDLLLLD (SEQ ID NO: 79) |
| bovineMBP | protein | SEQ ID NO: 7 |
| HSP70 556-575 | peptide | GLKGKISEADKKKVLDKCQE (SEQ ID NO: 80) |
| CNP 391-410 | peptide | RAIFTGYYGKGKPVPTQGSR (SEQ ID NO: 81) |
| MOG 211-230 | peptide | derived from SEQ ID NO: 5 |
| PLP 220-249 | peptide | derived from SEQ ID NO: 12 |
| HSP70 616-635 | peptide | PGPGGFGAQGPKGGSGSGPT (SEQ ID NO: 82) |
| AB1-12 | peptide | DAEFRHDSGYEV (SEQ ID NO: 100) |
| HSP60 556-573 | peptide | PGMGAMGGMGGGMGGGMF (SEQ ID NO: 83) |
| PLP 250-269 | peptide | derived from SEQ ID NO: 12 |

TABLE 2

Antigens Discriminating PPMS and healthy controls (HC)

| Antigen | Type | Sequence/SEQ ID NO: |
|---|---|---|
| PLP 215-232 | peptide | derived from SEQ ID NO: 12 |
| mMBP | protein | SEQ ID NO: 8 |
| HSP70 195-214 | peptide | LIFDLGGGTFDVSILTIDDG (SEQ ID NO: 51) |
| smLPS (*Salmonella minnesota* LPS) | lipid + saccharide | |
| HSP70 210-229 | peptide | TIDDGIFEVKATAGDTHLGG (SEQ ID NO: 42) |
| Chondroitin 4-Sulfate | saccharide | |
| HSP70 166-185 | peptide | GLNVLRIINEPTAAAIAYGL (SEQ ID NO: 70) |
| bovineMBP | protein | SEQ ID NO: 7 |
| PLP 137-150 | peptide | derived from SEQ ID NO: 12 |
| MOG 46-65 | peptide | derived from SEQ ID NO: 5 |
| CNP 406-421 | peptide | TQGSRKGGALQSCTII (SEQ ID NO: 60) |
| P2 31-50 | peptide | derived from SEQ ID NO: 10 |
| CNP 1-20 | peptide | MNRGFSRKSHTFLPKIFFRK (SEQ ID NO: 69) |
| MOG 16-35 | peptide | derived from SEQ ID NO: 5 |
| P2 76-95 | peptide | derived from SEQ ID NO: 10 |
| Neurofilament 68 kDa | peptide | SEQ ID NO: 16 |
| Amyloid Beta (AB) | protein | DAEFRHDSGYEVHHQKLVFFAEDVGSNKGAII GLMVGGVVIAT (SEQ ID NO: 13) |
| HSP70 466-485 | peptide | PAPGVPQIEVTFDIDANGIL (SEQ ID NO: 68) |
| AB 1-40 | peptide | DAEFRHDSGYEVHHQKLVFFAEDVGSNKGAII GLMVGGVV (SEQ ID NO: 101) |
| PLP 161-180 | peptide | derived from SEQ ID NO: 12 |
| PLP 40-59 | peptide | derived from SEQ ID NO: 12 |

TABLE 2-continued

Antigens Discriminating PPMS and healthy controls (HC)

| Antigen | Type | Sequence/SEQ ID NO: |
| --- | --- | --- |
| PLP 137-150 | peptide | derived from SEQ ID NO: 12 |
| HSP60 76-95 | peptide | DGVTVAKSIDLKDKYKNIGA (SEQ ID NO: 67) |
| MOG 151-170 | peptide | derived from SEQ ID NO: 5 |
| P2 1-20 | peptide | derived from SEQ ID NO: 10 |
| OSP 61-80 | peptide | GLYHCKPLVDILILPGYVQA (SEQ ID NO: 29) |
| Secreted APPalpha | peptide | derived from SEQ ID NO: 20 |
| PLP 178-191 | peptide | derived from SEQ ID NO: 12 |
| gpMBP | protein | derived from SEQ ID NO: 9 |
| HSP70 16-35 | peptide | SCVGVFQHGKVEIIANDQGN (SEQ ID NO: 84) |
| MBP 104-123 | peptide | derived from SEQ ID NO: 6 |
| SOD | protein | SEQ ID NO: 22 |
| ecLPS (E. Coli LPS) | lipid + saccharide | |
| HSP70 121-140 | peptide | SMVLTKMKEIAEAYLGYPVT (SEQ ID NO: 71) |
| MOBP 61-80 | peptide | derived from SEQ ID NO: 4 |
| OSP 1-20 | peptide | MVATCLQVVGFVTSFVGWIG (SEQ ID NO: 85) |

TABLE 3

Antigens Discriminating SPMS and RRMS

| Antigen | Type | Sequence/SEQ ID NO: |
| --- | --- | --- |
| MOG 61-80 | peptide | derived from SEQ ID NO: 5 |
| HSP60 376-395 | peptide | EQLDVTTSEYEKEKLNERLA (SEQ ID NO: 35) |
| MOG 31-50 | peptide | derived from SEQ ID NO: 5 |
| CNP 361-380 | protein | GEEVGELSRGKLYSLGNGRW (SEQ ID NO: 86) |
| Amyloid beta 1-23 | peptide | DAEFRHDSGYEVHHQKLVFFAED (SEQ ID NO: 102) |
| CNP 346-365 | peptide | LDLLEILRQEKGGSRGEEVG (SEQ ID NO: 87) |
| HSP60 496-515 | peptide | QSSSEVGYDAMAGDFVNMVE (SEQ ID NO: 26) |
| OSP 1-20 | peptide | MVATCLQVVGFVTSFVGWIG (SEQ ID NO: 85) |
| HSP60 511-530 | peptide | VNMVEKGIIDPTKVVRTALL (SEQ ID NO: 63) |
| OSP 61-80 | peptide | GLYHCKPLVDILILPGYVQA (SEQ ID NO: 29) |
| HSP60 286-305 | peptide | LVLNRLKVGLQVVAVKAPGF (SEQ ID NO: 25) |
| CNP 240-259 | peptide | YFGKRPPGVLHCTTKFCDYG (SEQ ID NO: 55) |
| HSP70 601-620 | peptide | VCNPIISGLYQGAGGPGPGG (SEQ ID NO: 88) |
| HSP60 210-229 | peptide | ELEIIEGMKFDRGYISPYFI (SEQ ID NO: 89) |
| HSP60 451-470 | peptide | LDSLTPANEDQKIGIEIIKR (SEQ ID NO: 90) |
| MOBP 166-185 | peptide | derived from SEQ ID NO: 4 |
| HSP60 166-185 | peptide | EEIAQVATISANGDKEIGNI (SEQ ID NO: 53) |

TABLE 3-continued

Antigens Discriminating SPMS and RRMS

| Antigen | Type | Sequence/SEQ ID NO: |
|---|---|---|
| MBP 138-147 | peptide | derived from SEQ ID NO: 6 |
| CNP 195-214 | peptide | KKSSETLRKAGQVFLEELGN (SEQ ID NO: 91) |
| MBP 1-20 | peptide | derived from SEQ ID NO: 6 |
| HSP60 526-545 | peptide | RTALLDAAGVASLLTTAEVV (SEQ ID NO: 28) |
| P2 1-20 | peptide | derived from SEQ ID NO: 10 |
| HSP70 286-305 | peptide | SLFEGIDFYTSITRARFEEL (SEQ ID NO: 36) |
| MBP 155-178 | peptide | derived from SEQ ID NO: 6 |
| P2 46-65 | peptide | derived from SEQ ID NO: 10 |
| HSP60 195-214 | peptide | RKGVITVKDGKTLNDELEII (SEQ ID NO: 48) |
| P2 31-50 | peptide | derived from SEQ ID NO: 10 |
| HSP60 271-290 | peptide | LVIIAEDVDGEALSTLVLNR (SEQ ID NO: 44) |
| HSP60 136-155 | peptide | NPVEIRRGVMLAVDAVIAEL (SEQ ID NO: 37) |
| CNP 286-305 | peptide | ISALFVTPKTTGARVELSEG (SEQ ID NO: 31) |
| HSP70 210-229 | peptide | TIDDGIFEVKATAGDTHLGG (SEQ ID NO: 42) |
| HSP70 136-155 | peptide | GYPVTNAVITVPAYFNDSQR (SEQ ID NO: 38) |
| PLP 150-163 | peptide | derived from SEQ ID NO: 12 |
| HSP70 166-185 | peptide | GLNVLRIINEPTAAAIAYGL (SEQ ID NO: 70) |
| HSP60 255-275 | peptide | QSIVPALEIANAHRKPLVI IA (SEQ ID NO: 32) |
| HSP60 16-35 | peptide | RVLAPHLTRAYAKDVKFGAD (SEQ ID NO: 56) |
| bovineMBP | protein | SEQ ID NO: 7 |
| CNP 181-199 | peptide | LEKDFLPLYFGWFLTKKS SE (SEQ ID NO: 92) |
| CNP 121-140 | peptide | LDDTNHERERLEQLFEMADQ (SEQ ID NO: 93) |
| Asialoganglioside-GM2 | lipid | |
| Amyloid beta 1-12 | peptide | DAEFRHDSGYEV (SEQ ID NO: 100) |
| OSP 121-140 | peptide | QLAGVLLILLALCALVATIW (SEQ ID NO: 94) |
| Secreted APPbeta | protein | SEQ ID NO: 21 |
| Cardiolipin | lipid | |
| HSP70 406-425 | peptide | AGGVMTALIKRNSTIPTKQT (SEQ ID NO: 64) |
| HSP60 361-380 | peptide | KGDKAQIEKRIQEIIEQLDV (SEQ ID NO: 40) |
| Amyloid beta 17-40 | peptide | LVFFAEDVGSNKGAIIGLMVGGVV (SEQ ID NO: 103) |
| Cholesterol | lipid | PubChem Substance ID: 24893094 |
| Amyloid beta 1-42 | peptide | DAEFRHDSGYEVHHQKLVFFAEDVGSNKGAIIGLMVGGVVIA (SEQ ID NO: 73) |
| PLP 80-99 | peptide | derived from SEQ ID NO: 12 |
| PLP 65-84 | peptide | derived from SEQ ID NO: 12 |
| PLP 40-59 | peptide | derived from SEQ ID NO: 12 |
| PLP 1-19 | peptide | derived from SEQ ID NO: 12 |
| PLP 151-173 | peptide | derived from SEQ ID NO: 12 |

TABLE 3-continued

Antigens Discriminating SPMS and RRMS

| Antigen | Type | Sequence/SEQ ID NO: |
|---|---|---|
| HSP70 421-440 | peptide | PTKQTQIFTTYSDNQPGVLI (SEQ ID NO: 95) |
| huMBP | protein | SEQ ID NO: 6 |
| MOBP 16-35 | peptide | derived from SEQ ID NO: 4 |
| CNP 16-35 | peptide | IFFRKMSSSGAKDKPELQFP (SEQ ID NO: 75) |
| RBP | protein | SEQ ID NO: 19 |
| HSP70 331-350 | peptide | IHDLVLVGGSTRIPKVQKLL (SEQ ID NO: 96) |
| MBP 113-132 | peptide | derived from SEQ ID NO: 6 |
| beta Crystallin | protein | derived from SEQ ID NO: 15 |
| PLP 178-191 | peptide | derived from SEQ ID NO: 12 |

TABLE 4

Antigens discriminating lesion Pattern I and Pattern II

| Antigen | Type | Sequence/SEQ ID NO: |
|---|---|---|
| 15-ketocholestane | lipid | |
| 15α-hydroxycholestene | lipid | |
| Ganglioside-GM4 | lipid | |
| 15-ketocholestene | lipid | |
| Tetrasialoganglioside-GQ1B | lipid | |
| Brain L-α-lysophosphatidylserine | lipid | |
| Lactosylceramide | lipid | |
| 160 kDa. neurofilament | peptide | SEQ ID NO: 17 |
| HSP60 240-259 | peptide | QDAYVLLSEKKISSIQSIVP (SEQ ID NO: 43) |
| OSP 166-185 | peptide | VLCLVGGCVILCCAGDAQAF (SEQ ID NO: 97) |
| MOG 196-215 | peptide | derived from SEQ ID NO: 5 |
| OSP 61-80 | peptide | GLYHCKPLVDILILPGYVQA (SEQ ID NO: 29) |
| OSP 1-20 | peptide | MVATCLQVVGFVTSFVGWIG (SEQ ID NO: 85) |
| PLP 215-232 | peptide | derived from SEQ ID NO: 12 |

TABLE 5

Accession No. and SEQ ID NO. of the proteins listed in Table 1 to 4

| Protein (abbreviation) | Protein | Accession No. | SEQ ID NO: |
|---|---|---|---|
| HSP60 | 60 kDa Heat Shock Protein | GI: 41399285 | SEQ ID NO: 1 |
| HSP70 | 70 kDa Heat Shock Protein | GI: 38327039 | SEQ ID NO: 2 |
| CNP | 2',3'-cyclic nucleotide 3'-phosphodiesterase | GI: 94721261 | SEQ ID NO: 3 |
| MOBP | Myelin-Associated Oligodendrocytic Basic Protein | GI: 1408050 | SEQ ID NO: 4 |
| MOG | Myelin/oligodendrocyte glycoprotein | GI: 56788381 | SEQ ID NO: 5 |

TABLE 5-continued

Accession No. and SEQ ID NO. of the proteins listed in Table 1 to 4

| Protein (abbreviation) | Protein | Accession No. | SEQ ID NO: |
|---|---|---|---|
| MBP/huMBP | human Myelin Basic Protein | GI: 68509930 | SEQ ID NO: 6 |
| bovineMBP | *Bos Taurus* Myelin Basic Protein | GI: 74268137 | SEQ ID NO: 7 |
| mMBP | *Mus musculus* Myelin Basic Protein | GI: 6754658 | SEQ ID NO: 8 |
| gpMBP | *Cavia porcellus* Myelin Basic Protein | GI: 3309629 | SEQ ID NO: 9 |
| P2 | Myelin Protein 2 | GI: 4505909 | SEQ ID NO: 10 |
| OSP | Oligodendrocyte-Specific Protein | GI: 3283415 | SEQ ID NO: 11 |
| PLP | Proteolipid Protein | GI: 41349499 | SEQ ID NO: 12 |
| GFAP | Glial fibrillary acidic protein | GI: 4503979 | SEQ ID NO: 14 |
| beta Crystalline | | GI: 12056461 | SEQ ID NO: 15 |
| Neurofilament 68 kDa | | GI: 105990539 | SEQ ID NO: 16 |
| Neurofilament 160 kDa | | GI: 157738649 | SEQ ID NO: 17 |
| Amyloid beta | | GI: 41406057 | SEQ ID NO: 18 |
| RBP | Retinol-binding protein 4, plasma precursor | GI: 55743122 | SEQ ID NO: 19 |
| APP alpha | amyloid beta protein precursor isoform b | GI: 4502167 | SEQ ID NO: 20 |
| APP beta | amyloid beta protein precursor isoform a | GI: 41406055 | SEQ ID NO: 21 |
| SOD | superoxide dismutase 1 | GI: 4507149 | SEQ ID NO: 22 |

According to a first aspect, the present invention provides a method of diagnosing a subtype of multiple sclerosis (MS) in a subject, the method comprising determining the reactivity of antibodies in a sample obtained from the subject to a plurality of antigens selected from the group consisting of the antigens listed in Tables 1 to 4, thereby determining the reactivity pattern of the sample to the plurality of antigens, and comparing the reactivity pattern of said sample to a control reactivity pattern, wherein the subtype of MS is selected from the group consisting of:

(i) relapsing remitting multiple sclerosis (RRMS) wherein said plurality of antigens is selected from the group consisting of the antigens listed in Table 1;

(ii) primary progressive multiple sclerosis (PPMS) wherein said plurality of antigens is selected from the group consisting of the antigens listed in Table 2;

(iii) secondary progressive multiple sclerosis (SPMS) wherein said plurality of antigens is selected from the group consisting of the antigens listed in Table 3; and (iv) a pathologic subtype of MS selected form MS characterized by Pattern I lesions and Pattern II lesions wherein said plurality of antigens is selected from the group consisting of the antigens listed in Table 4.

According to certain embodiments of this aspect, a significant difference between the reactivity pattern of said sample obtained from the subject compared to a reactivity pattern of a control sample is an indication that the subject is afflicted with a subtype of MS.

As used herein, the "reactivity of antibodies in a sample" to "a plurality of antigens" refers to the immune reactivity of each antibody in the sample to a specific antigen selected from the plurality of antigens. The immune reactivity of the antibody to the antigen, i.e. its ability to specifically bind the antigen, may be used to determine the amount of the antibody in the sample. The reactivity pattern of the sample thus reflects the levels of each one of the tested antibodies in the sample.

Typically, determining the reactivity of antibodies in the sample to the plurality of antigens is performed using an immunoassay. Advantageously, the plurality of antigens may be used in the form of an antigen array.

A "significant difference" between reactivity patterns refers, in different embodiments, to a statistically significant difference, or in other embodiments to a significant difference as recognized by a skilled artisan. Advantageously, the methods of the invention may employ the use of learning and pattern recognition analyzers, clustering algorithms and the like, in order to discriminate between reactivity patterns of control subjects to those of patients having a subtype of MS. As such, this term specifically includes a difference measured by, for example, determining the reactivity of antibodies in a test sample to a plurality of antigens, and comparing the resulting reactivity pattern to the reactivity patterns of negative and positive control samples (e.g. samples obtained from control subjects which are not afflicted with a subtype of MS or patients afflicted with the tested MS subtype, respectively) using such algorithms and/or analyzers. According to certain embodiments, the control sample is obtained from patients afflicted with another subtype of MS (i.e. the sample may be tested for SPMS while the control sample is obtained form RRMS patients). The difference may also be measured by comparing the reactivity pattern of the test sample to a predetermined classification rule obtained in such manner.

Thus, in another embodiment, a significant difference between the reactivity pattern of a test sample compared to a reactivity pattern of a control sample, wherein the difference is computed using a learning and pattern recognition algorithm, indicates that the subject is afflicted with a subtype of MS. For example, the algorithm may include, without limitation, supervised or non-supervised classifiers including statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor, artificial neural networks, coupled two-way clustering algorithms, multi-layer perceptrons (MLP), generalized regression neural network (GRNN), fuzzy inference systems (FIS), self-organizing map (SOM), genetic algorithms (GAS), neuro-fuzzy systems (NFS), adaptive resonance theory (ART).

According to certain embodiments of the methods of the present invention, the control is selected from the group consisting of a sample from at least one individual, a panel of control samples from a set of individuals, and a stored set of data from control individuals.

According to additional embodiments the sample is a serum sample. According to another embodiment the sample is cerebrospinal fluid (CSF). In other particular embodiments, the test sample and control samples may comprise IgG and/or IgM antibodies. In another embodiment, tables 1 to 4 of the methods and kits of the invention comprise duplicates of particular antigens (e.g. PLP 215-232, bovineMBP and CNP 1-20 in table 2 and PLP 1-19, OSP 121-140 and CNP 240-259 in Table 3) for determining the reactivity of IgG and IgM antibodies. In another embodiment, the reactivity of one antibody to a specific antigen (from the plurality of antigens) is up-regulated. In another embodiment, the reactivity of one antibody to a specific antigen is down-regulated.

According to some embodiments, the method further comprises diluting the sample e.g. 1:10 or more before determining the reactivity of antibodies in the sample.

According to other embodiments, the plurality of antigens is used in the form of an antigen array. According to some embodiments the antigen array is arranged in the form of an antigen chip.

According to certain embodiments, the subtype of MS is relapsing remitting multiple sclerosis (RRMS) and the plurality of antigens is selected from Table 1. According to this particular embodiment, the control reactivity pattern is obtained from healthy patients or a stored set of data from healthy patients. According to specific embodiments, the plurality of antigens comprises at least 5, at least 10, at least 15, at least 20, at least 25, at least 30, at least 35, at least 40, at least 45, at least 50, at least 55, at least 60, at least 65, at least 70, at least 75, at least 80, at least 85, at least 90 different antigens of the antigens listed in Table 1. According to another embodiment, the plurality of antigens comprises all the antigens listed in Table 1. Preferably the antigen set required to provide a reliable and accurate correlation between the diagnosis and the patient's condition consists of no more than 100, preferably no more than 115, more preferably no more than 130, and most preferably no more than 150 antigens. In another embodiment, the plurality of antigens consists of the antigens listed in Table 1. Each possibility represents a separate embodiment of the present invention.

According to certain embodiments, the subtype of MS is primary progressive multiple sclerosis (PPMS) and the plurality of antigens is selected from Table 2. According to this particular embodiment, the control reactivity pattern is obtained from healthy patients or a stored set of data from healthy patients. According to specific embodiments, the plurality of antigens comprises at least 5, at least 10, at least 15, at least 20, at least 25, at least 30, at least 35 different antigens of the antigens listed in Table 2. According to another embodiment, the plurality of antigens comprises all the antigens listed in Table 2. Preferably the antigen set required to provide a reliable and accurate correlation between the diagnosis and the patient's condition consists of no more than 50, preferably no more than 70, more preferably no more than 80, and most preferably no more than 100 antigens. In another embodiment, the plurality of antigens consists of the antigens listed in Table 2. Each possibility represents a separate embodiment of the present invention.

According to certain embodiments, the subtype of MS is secondary progressive multiple sclerosis (SPMS) and the plurality of antigens is selected from Table 3. According to this particular embodiment, the control reactivity pattern is selected from the group consisting of a sample from at least one individual afflicted with RRMS, a panel of control samples from a set of individuals afflicted with RRMS, and a stored set of data from control individuals afflicted with RRMS. According to specific embodiments, the plurality of antigens comprises at least 5, at least 10, at least 15, at least 20, at least 25, at least 30, at least 35, at least 40, at least 45, at least 50, at least 55, at least 60 different antigens of the antigens listed in Table 3. According to another embodiment, the plurality of antigens comprises all the antigens listed in Table 3. Preferably the antigen set required to provide a reliable and accurate correlation between the diagnosis and the patient's condition, consists of no more than 80, preferably no more than 90, and most preferably no more than 100 antigens. In another embodiment, the plurality of antigens consists of the antigens listed in Table 3. Each possibility represents a separate embodiment of the present invention.

According to some embodiments, the subtype of MS is a pathologic pattern of MS selected from Pattern I MS lesion and Pattern II MS lesions and the plurality of antigens is selected from Table 4. According to one embodiment, the present invention provides a method for diagnosing Pattern I lesions in a subject with MS and the control reactivity pattern is obtained from patients having Pattern II lesions. According to another embodiment, the present invention provides a method for diagnosing Pattern II lesions in a subject with MS and the control reactivity pattern is obtained from patients having Pattern I lesions. According to another embodiment, the present invention provides a method for distinguishing between subjects having lesion Pattern I and subjects having lesion Pattern II in subjects afflicted with MS. According to specific embodiments, the plurality of antigens comprises at least 4, at least 6, at least 8, at least 10, at least 12 different antigens of the antigens listed in Table 4. According to another embodiment, the plurality of antigens comprises all the antigens listed in Table 4. Preferably the antigen set required to provide a reliable and accurate correlation between the diagnosis and the patient's condition, consists of no more than 20, preferably no more than 30, and most preferably no more than 50 antigens. In another embodiment, the plurality of antigens consists of the 14 antigens listed in Table 4. Each possibility represents a separate embodiment of the present invention.

According to certain embodiments, the present invention provides a method for diagnosing a subtype of MS in a subject, the method comprising:
(a) determining the reactivity of antibodies in a sample obtained from the subject to a plurality of antigens selected from the group consisting of the antigens listed in Tables 1, thereby determining the reactivity pattern of the sample to the plurality of antigens, and comparing the reactivity pattern of said sample to a control reactivity pattern obtained from healthy subjects;
(b) determining the reactivity of antibodies in a sample obtained from the subject to a plurality of antigens selected from the group consisting of the antigens listed in Tables 2, thereby determining the reactivity pattern of the sample to the plurality of antigens, and comparing the reactivity pattern of said sample to a control reactivity pattern obtained from healthy subjects;
(c) determining the reactivity of antibodies in a sample obtained from the subject to a plurality of antigens selected from the group consisting of the antigens listed in Tables 3, thereby determining the reactivity pattern of the sample to the plurality of antigens, and comparing the reactivity pattern of said sample to a control reactivity pattern obtained from subjects afflicted with RRMS;

(d) determining the reactivity of antibodies in a sample obtained from the subject to a plurality of antigens selected from the group consisting of the antigens listed in Tables 4, thereby determining the reactivity pattern of the sample to the plurality of antigens, and comparing the reactivity pattern of said sample to a control reactivity pattern obtained from subjects having Pattern I lesions, and/or to a control reactivity pattern obtained from subjects having Pattern II lesions;

wherein:

(i) a significant difference between the reactivity pattern of (a) compared to said control reactivity pattern is an indication that the subject is afflicted with RRMS;

(ii) a significant difference between the reactivity pattern of (b) compared to said control reactivity pattern is an indication that the subject is afflicted with PPMS;

(iii) a significant difference between the reactivity pattern of (c) compared to said control reactivity pattern is an indication that the subject is afflicted with SPMS; and (iv) a significant difference between the reactivity pattern of (d) compared to a control reactivity pattern obtained from subjects having Pattern I lesions is an indication that the subject is afflicted with Pattern II lesions, and a significant difference between the reactivity pattern of (d) compared to a control reactivity pattern obtained from subjects having Pattern II lesions is an indication that the subject is afflicted with Pattern I lesions.

According to some embodiments, the control reactivity pattern for Table 1 and Table 2 is obtained from healthy control subjects or a stored set of data from healthy control subjects. According to another embodiment, the control reactivity pattern for Table 3 is obtained from subjects afflicted with RRMS or a stored set of data from subjects afflicted with RRMS.

According to another aspect, the present invention provides a kit for the diagnosis of a subtype of MS comprising:

(i) a plurality of antigens for the diagnosis of RRMS selected from the group consisting of the antigens listed in Table 1;

(ii) a plurality of antigens for the diagnosis of PPMS selected from the group consisting of the antigens listed in Table 2;

(iii) a plurality of antigens for the diagnosis of SPMS selected from the group consisting of the antigens listed in Table 3; and (iv) a plurality of antigens for discriminating between Pattern I lesions to Pattern II lesions in a subject with MS, selected from the group consisting of the antigens listed in Table 4.

According to certain embodiments, the present invention provides a kit for the diagnosis of RRMS, comprising a plurality of antigens selected from the group consisting of the antigens listed in Table 1. According to specific embodiments, the plurality of antigens comprises at least 5, at least 10, at least 15, at least 20, at least 25, at least 30, at least 35, at least 40, at least 45, at least 50, at least 55, at least 60, at least 65, at least 70, at least 75, at least 80, at least 85, at least 90 different antigens of the antigens listed in Table 1. According to another embodiment, the plurality of antigens comprises all the antigens listed in Table 1. Each possibility represents a separate embodiment of the present invention.

According to certain embodiments, the present invention provides a kit for the diagnosis of PPMS, comprising a plurality of antigens selected from the group consisting of the antigens listed in Table 2. According to specific embodiments, the plurality of antigens comprises at least 5, at least 10, at least 15, at least 20, at least 25, at least 30, at least 35 different antigens of the antigens listed in Table 2. According to another embodiment, the plurality of antigens comprises all the antigens listed in Table 2. Each possibility represents a separate embodiment of the present invention.

According to certain embodiments, the present invention provides a kit for the diagnosis of SPMS, comprising a plurality of antigens selected from the group consisting of the antigens listed in Table 3. According to specific embodiments, the plurality of antigens comprises at least 5, at least 10, at least 15, at least 20, at least 25, at least 30, at least 35, at least 40, at least 45, at least 50, at least 55, at least 60 different antigens of the antigens listed in Table 3. According to another embodiment, the plurality of antigens comprises all the antigens listed in Table 3. Each possibility represents a separate embodiment of the present invention.

According to certain embodiments, the present invention provides a kit for discriminating between Pattern I lesions to Pattern II lesions in a subject with MS, comprising a plurality of antigens selected from the group consisting of the antigens listed in Table 4. According to specific embodiments, the plurality of antigens comprises at least 4, at least 6, at least 8, at least 10, at least 12 different antigens of the antigens listed in Table 4. According to another embodiment, the plurality of antigens comprises all the antigens listed in Table 4. Each possibility represents a separate embodiment of the present invention.

In other embodiments, the kit may further comprise means for determining the reactivity of antibodies in a sample to the plurality of antigens. For example, the kit may contain reagents, detectable labels and/or containers which may be used for measuring specific binding of antibodies to the antigen probes of the invention. In a particular embodiment, said kit is in the form of an antigen array. In other embodiments, said kit may further comprise negative and/or positive control samples. For example, a negative control sample may contain a sample from at least one healthy individual or at least one individual identified with another subtype of MS (e.g. samples obtained from at least one individual afflicted with RRMS are used as a negative control while the kit is for means of diagnosing SPMS in a test sample). A positive control may contain a sample from at least one individual afflicted with the sub-type of MS which is being diagnosed. Other non-limiting examples are a panel of control samples from a set of healthy individuals or diseased individuals, or a stored set of data from control individuals.

In other embodiments, the kit may further comprise means for comparing reactivity patterns of antibodies in different samples to the plurality of antigens. In a specific embodiment, the means for comparing reactivity patterns comprises a learning and pattern recognition analyzer (e.g. utilizing learning and pattern recognition algorithms as detailed herein).

According to other embodiments, the methods and kits of the present invention are useful for monitoring MS progression.

According to another aspect, the present invention provides an antigen probe set comprising the antigen probes listed in Table 1. According to certain embodiments, the antigen probe set comprises a subset of the antigens listed in Table 1, as detailed herein.

According to another aspect, the present invention provides an antigen probe set comprising the antigen probes listed in Table 2. According to certain embodiments, the antigen probe set comprises a subset of the antigens listed in Table 2, as detailed herein.

According to another aspect, the present invention provides an antigen probe set comprising the antigen probes listed in Table 3. According to certain embodiments, the antigen probe set comprises a subset of the antigens listed in Table 3, as detailed herein.

According to another aspect, the present invention provides an antigen probe set comprising the antigen probes listed in Table 4. According to certain embodiments, the antigen probe set comprises a subset of the antigens listed in Table 4, as detailed herein.

According to another aspect, the present invention provides an article of manufacture comprising the antigen probe set of the present invention.

According to another aspect, the present invention provides use of an antigen probe set for the preparation of a diagnostic composition for diagnosing a subtype of MS, the antigen probe set containing a plurality of antigens selected from the group consisting of the antigens listed in one of Tables 1 to 4, wherein the subtype of MS is selected from the group consisting of:
  (i) RRMS wherein said plurality of antigens is selected from the group consisting of the antigens listed in Table 1;
  (ii) PPMS wherein said plurality of antigens is selected from the group consisting of the antigens listed in Table 2;
  (iii) SPMS wherein said plurality of antigens is selected from the group consisting of the antigens listed in Table 3; and
  (iv) a pathologic subtype of MS selected form Pattern I lesions and Pattern II lesions wherein said plurality of antigens is selected from the group consisting of the antigens listed in Table 4.

In one embodiment, the diagnostic composition is useful for determining the reactivity of antibodies in a sample, thereby determining the reactivity pattern of the sample to said plurality of antigens, wherein a significant difference between the reactivity pattern of said sample compared to a reactivity pattern of a control sample is an indication for a subtype of MS.

Other objects, features and advantages of the present invention will become clear from the following description and drawings.

BRIEF DESCRIPTION OF THE DRAWINGS

FIG. 2 shows the serum antibody reactivity in RRMS, PPMS and SPMS.

DETAILED DESCRIPTION OF THE INVENTION

Figure 1A:
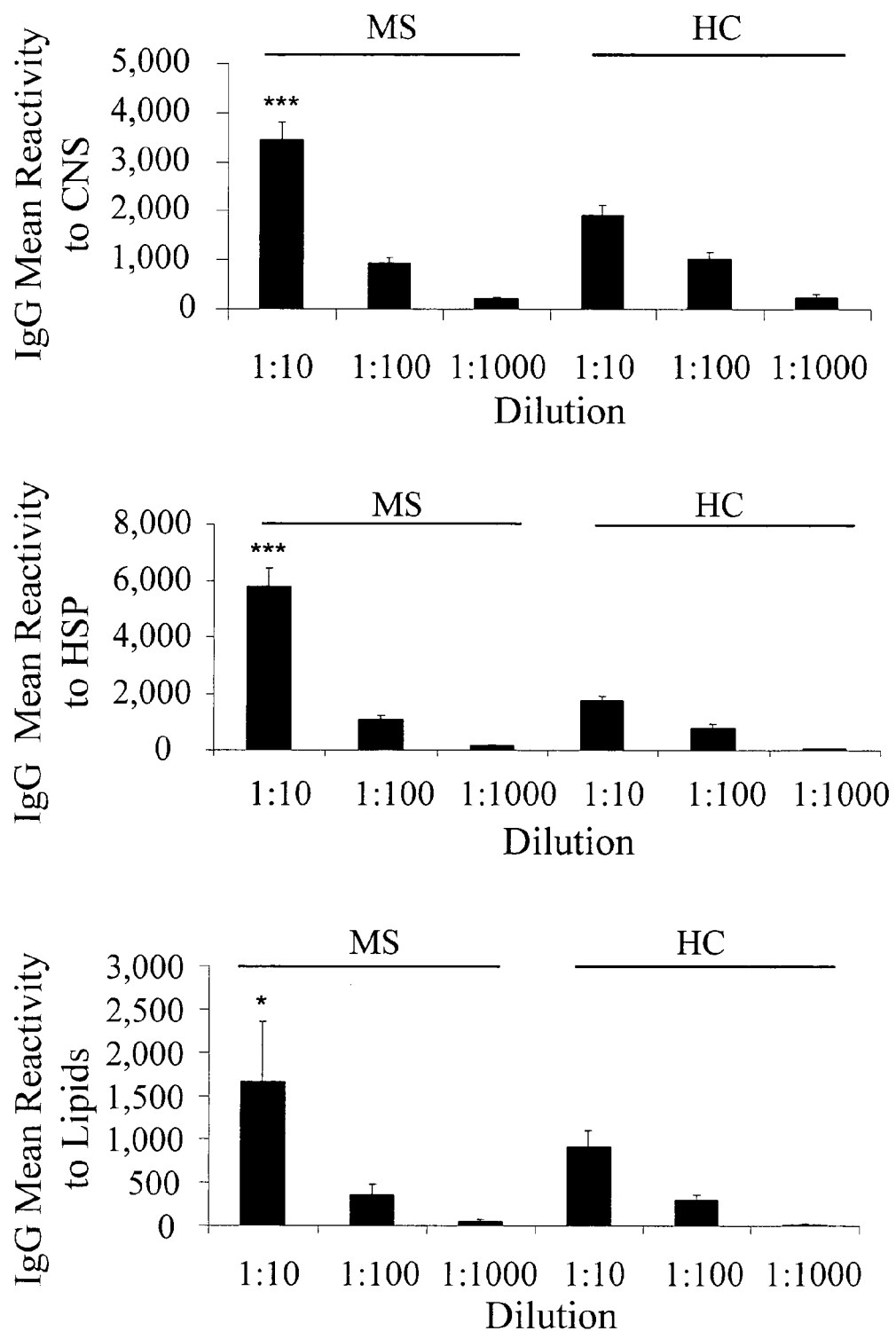
FIG. 1 shows the performance of antigen microarrays. RRMS or healthy controls (HC) serum samples were hybridized on antigen microarrays at different concentrations and the mean IgG (FIG. 1A) and IgM (FIG. 1B) reactivity to the CNS, HSP or lipid antigens spotted on the microarrays were measured. Results are presented as mean±SEM of the IgG or IgM reactivity for CNS, HSP or lipid antigens at each dilution. *$P<0.05$, $P<0.01$ and *$P<0.001$ (two-way ANOVA) when compared to HC samples tested at the same dilution.
FIG. 1C shows RRMS sera (1:10 dilution) preincubated with different concentrations of PLP261-277 or HSP601-20 and their IgG reactivity to PLP261-277 was measured on antigen microarrays. $P<0.01$ and *$P<0.001$ (one-way ANOVA) when compared to samples that were pre-incubated with no competitor.

The present invention provides methods of diagnosing multiple sclerosis (MS) in a subject, using antigen probe arrays for practicing such a diagnosis, and identifies specific antigen probe sets for generating such arrays. According to some embodiments, the present invention relates to an autoantibody-based biomarker test for early diagnosis and for monitoring the progress of MS. Particularly, the methods and kits of the present invention can distinguish the form of MS (namely RRMS, SPMS or PPMS) in a subject. Further, the methods and kits of the invention can distinguish the lesion pattern, particularly between lesion pattern I to lesion pattern II, in MS patients.

As exemplified herein below, antigen-microarray analysis of autoantibodies can identify serum and CSF autoantibody signatures associated with different clinical forms and pathologic subtypes of MS; the signatures were based on collective autoantibody patterns, not single autoantibody reactivities. These informative patterns emerged from autoantibodies that bound peptides of myelin molecules and HSP, proteins and lipids. Moreover, the informative patterns included decreases as well as increases of autoantibody reactivities relative to those found in HC.

Further, the unique antibody patterns were associated with different patterns of MS pathology. Pattern II MS pathology was associated with increased IgG antibodies to HSP60, OSP, MOG and PLP peptide epitopes, whereas increased antibody reactivity to gangliosides, lactosylceramide and L-α-lysophosphatidylserine was linked to pattern I. Antibodies to lactosylceramide and L-α-lysophosphatidylserine have been described in the CSF of MS patients and EAE mice (Kanter et al., 2006). Pattern I serum samples also contained antibodies to oxidized cholesterol derivatives (15-ketocholestene, 15-ketocholestane and 15a-hydroxycholestene). Increased levels of 7-ketocholesterol, a related oxidized derivative of cholesterol, have been found in the CSF of MS patients. Notably, 7-ketocholesterol and gangliosides activate microglial cells by PARP and toll-like receptor 4 dependent pathways, respectively.

A significant finding of the studies presented herein was that the antibody repertoires in CSF and serum of MS patients were clearly distinct. These results are consistent with the compartmentalization of the immune response in the CSF of MS subjects. Although antibodies in the CSF have been extensively investigated in MS, the unique antibody immune signatures as described herein have not been described before.

Initial studies suggest that unique signatures may be associated with response to therapy and disease progression. For example, approximately 50% of RMSS patients become SPMS, and this conversion is associated with changes in immunological and neurodegenerative mechanisms. As exhibited herein below, studies of SPMS with antigen arrays revealed antibody signatures that share characteristics of both RRMS and PPMS patients, suggesting that antigen arrays are useful to monitor this change in disease pattern. Moreover, if these antibody patterns are established early in the course of the disease, they will be useful for early diagnosis and screening for MS susceptibility as they can be measured in small quantities of serum. Thus, the findings presented herein demonstrate that serum microarray antibody patterns provide a new avenue both to monitor MS, e.g., to determine the prognosis of the disease, and to characterize immunopathogenic mechanisms of the disease.

Antigen Probes and Antigen Probe Sets

According to further embodiments, the invention provides antigen probes and antigen probe sets useful for diagnosing MS, as detailed herein.

According to the principles of the invention, the invention further provides a plurality of antigens also referred to herein as antigen probe sets. These antigen probe sets comprising a plurality of antigens are reactive specifically with the sera of subjects having MS. According to the principles of the invention, the plurality of antigens may advantageously be used in the form of an antigen array. According to some embodiments the antigen array is conveniently arranged in the form of an antigen chip.

A "probe" as used herein means any compound capable of specific binding to a component. According to one aspect, the present invention provides an antigen probe set comprising the antigen probes listed in Table 1. According to certain embodiments, the antigen probe set comprises a subset of the antigens listed in Table 1. According to certain embodiments, the antigen probe sets of the invention comprise a plurality of antigens selected from Table 1, as detailed herein, for the diagnosis of RRMS. Preferably, the plurality of antigens comprises a set of the antigens listed in Table 1. Yet in other embodiments, the antigen probe set comprises or consists of a subset thereof, e.g. at least 5, 10, 15, 20, 25, 30, 35, 40, 45, 50, 55, 60, 65, 70, 75, 80, 85, 90 different antigens each selected from the list as specified in Table 1 wherein each possibility represents a separate embodiment of the invention. Such subsets may be selected so as to result in optimal sensitivity and/or specificity of the diagnostic assay. In other embodiments, the probe set comprises up to 115, or in other embodiments up to 130 or 150 different antigens. In other embodiments, a probe set consisting of the antigens as specified in Table 1 is sufficient to discriminate between RRMS patients, and healthy individuals that are not afflicted with RRMS. It should be noted, that while such probe sets are considered sufficient for reliably identifying a subject with RRMS, the antigen probe sets of the invention may conveniently be used, in certain embodiments, in the form of antigen arrays comprising a greater number of antigens, e.g. about 130 antigens or more. According to another aspect, the present invention provides an antigen probe set comprising the antigen probes listed in Table 2. According to certain embodiments, the antigen probe set comprises a subset of the antigens listed in Table 2. According to other embodiments, the antigen probe sets of the invention comprise a plurality of antigens selected from Table 2, as detailed herein, for the diagnosis of PPMS. Preferably, the plurality of antigens comprises a set of the antigens listed in Table 2. Yet in other embodiments, the antigen probe set comprises or consists of a subset thereof, e.g. at least 5, 10, 15, 20, 25, 30, 35 different antigens each selected from the list as specified in Table 2 wherein each possibility represents a separate embodiment of the invention. Such subsets may be selected so as to result in optimal sensitivity and/or specificity of the diagnostic assay. In other embodiments, the probe set comprises up to 50, or in other embodiments up to 70 or 100 different antigens. In other embodiments, a probe set consisting of the antigens as specified in Table 2 is sufficient to discriminate between PPMS patients, and healthy individuals that are not afflicted with PPMS. It should be noted, that while such probe sets are considered sufficient for reliably identifying a subject with PPMS, the antigen probe sets of the invention may conveniently be used, in certain embodiments, in the form of antigen arrays comprising a greater number of antigens, e.g. about 100 antigens or more.

According to another aspect, the present invention provides an antigen probe set comprising the antigen probes listed in Table 3. According to certain embodiments, the antigen probe set comprises a subset of the antigens listed in Table 3. According to certain embodiments, the antigen probe sets of the invention comprise a plurality of antigens selected from Table 3, as detailed herein, for the diagnosis of SPMS. Preferably, the plurality of antigens comprises a set of the antigens listed in Table 3. Yet in other embodiments, the antigen probe set comprises or consists of a subset thereof, e.g. at least 5, 10, 15, 20, 25, 30, 35, 40, 45, 50, 55, 60 different antigens each selected from the list as specified in Table 3, wherein each possibility represents a separate embodiment of the invention. Such subsets may be selected so as to result in optimal sensitivity and/or specificity of the diagnostic assay. In other embodiments, the probe set comprises up to 80, or in other embodiments up to 100 or 150 different antigens. In other embodiments, a probe set consisting of the antigens as specified in Table 3 is sufficient to discriminate between SPMS patients and RRMS patients. It should be noted, that while such probe sets are considered sufficient for reliably identifying a subject with SPMS, the antigen probe sets of the invention may conveniently be used, in certain embodiments, in the form of antigen arrays comprising a greater number of antigens, e.g. about 130 antigens or more.

According to another aspect, the present invention provides an antigen probe set comprising the antigen probes listed in Table 4. According to certain embodiments, the antigen probe set comprises a subset of the antigens listed in Table 4. According to certain embodiments, the antigen probe sets of the invention comprise a plurality of antigens selected from Table 4, as detailed herein, for distinguishing between Pattern I and Pattern II MS lesions. Preferably, the plurality of antigens comprises a set of the 14 antigens listed in Table 4. Yet in other embodiments, the antigen probe set comprises or consists of a subset thereof, e.g. 4, 5, 6, 7, 8, 9, 10, 11, 12, 13 different antigens each selected from the list as specified in Table 4, wherein each possibility represents a separate embodiment of the invention. Such subsets may be selected so as to result in optimal sensitivity and/or specificity of the diagnostic assay. In other embodiments, the probe set comprises up to 20, or in other embodiments up to 30 or 50 different antigens. In other embodiments, a probe set consisting of 14 antigens as specified in Table 4 is sufficient to discriminate between patients having Pattern I or Pattern II MS lesions. It should be noted, that while such probe sets are considered sufficient for reliably identifying a MS pattern, the antigen probe sets of the invention may conveniently be used, in certain embodiments, in the form of antigen arrays comprising a greater number of antigens, e.g. about 50 antigens or more.

Antigen probes to be used in the assays of the invention may be purified or synthesized using methods well known in the art. For example, an antigenic protein or peptide may be produced using known recombinant or synthetic methods, including, but not limited to, solid phase (e.g. Boc or f-Moc chemistry) and solution phase synthesis methods (Stewart and Young, 1963; Meienhofer, 1973; Schroder and Lupke, 1965; Sambrook et al., 2001). One of skill in the art will possess the required expertise to obtain or synthesize the antigen probes of the invention. Some of the antigen probes are also commercially available, e.g. from Sigma (St. Louis, Mo., USA), Abnova (Taipei City, Taiwan), Matreya LLC (Pleasant Gap, Pa., USA), Avanti Polar Lipids (Alabaster, Ala., USA), Calbiochem (San Diego, Calif., USA), Chemicon (Temecula, Calif., USA), GeneTex (San Antonio, Tex., USA), Novus Biologicals (Littleton, Colo., USA) Assay Designs (Ann Arbor, Mich., USA), ProSci Inc. (Poway, Calif., USA), EMD Biosciences (San Diego, Calif., USA), Cayman Chemical (Ann Arbor, Mich., USA), HyTest (Turku, Finland), Meridian Life Science (Memphis, Tenn. USA) and Biodesign International (Saco, Me., USA), as detailed herein below.

It should be noted, that the invention utilizes antigen probes having the amino acid sequences as set forth in Table 1 to table 4, as well as homologs, fragments and derivatives thereof, as long as these homologs, fragments and derivatives are immunologically cross-reactive with these antigen probes. The term "immunologically cross-reactive" as used herein refers to two or more antigens that are specifically bound by the same antibody. The term "homolog" as used herein refers to a peptide which having at least 70%, at least 75%, at least 80%, at least 85% or at least 90% identity to the antigen's amino acid sequence. Cross-reactivity can be determined by any of a number of immunoassay techniques, such as a competition assay (measuring the ability of a test antigen to competitively inhibit the binding of an antibody to its known antigen).

The term peptide typically refers to a polypeptide of up to about 50 amino acid residues in length. According to particular embodiments, the antigenic peptides of the invention may be 10-50 amino acids in length and are typically about 10-30 or about 15-25 amino acids in length.

The term encompasses native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications.

The antigens of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid.

Functional derivatives consist of chemical modifications to amino acid side chains and/or the carboxyl and/or amino moieties of said peptides. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring or modified amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

The amino acid residues described herein are in the "L" isomeric form, unless otherwise indicated. However, residues in the "D" isomeric form can be substituted for any L-amino acid residue, as long as the peptide substantially retains the desired antibody specificity.

Suitable analogs may be readily synthesized by now-standard peptide synthesis methods and apparatus or recombinant methods. All such analogs will essentially be based on the antigens of the invention as regards their amino acid sequence but will have one or more amino acid residues deleted, substituted or added. When amino acid residues are substituted, such conservative replacements which are envisaged are those which do not significantly alter the structure or antigenicity of the polyeptide. For example basic amino acids will be replaced with other basic amino acids, acidic ones with acidic ones and neutral ones with neutral ones. In addition to analogs comprising conservative substitutions as detailed above, analogs comprising non-conservative amino acid substitutions are further contemplated, as long as these analogs are immunologically cross reactive with a peptide of the invention.

In other aspects, there are provided nucleic acids encoding these peptides, vectors comprising these nucleic acids and host cells containing them. These nucleic acids, vectors and host cells are readily produced by recombinant methods known in the art (see, e.g., Sambrook et al., 2001). For example, an isolated nucleic acid sequence encoding an antigen of the invention can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

The lipid antigens to be used in the assays of the invention may be purified or synthesized using methods well known in the art (see, for example, Biochemistry of Lipids, Lipoproteins, and Membranes, 4.sup.th Ed. (2002; Vance D E and Vance, J E, editors; Elsevier, Amsterdam, Boston); Enzymes in Lipid Modification (2000; Bornsheuer, U T, editor; Wiley-VCH, Weinheim, N.Y.); Lipid Synthesis and Manufacture (1999; Gunstone, F D, editor; Sheffield Academic Press, Sheffield, England; CRC Press, Boca Raton, Fla.); Lipid Biochemistry, 5.sup.th Ed (2002; Gun, M I, Harwood, J L, and Frayn, K N, editors; Blackwell Science, Oxford, Malden, Mass.). In another embodiment, the lipid antigens to be used in the assays of the invention may be commercially purchased as detailed herein below.

Diagnostic Methods

According to some embodiments, the invention provides diagnostic methods useful for the detection of MS, particularly RRMS, PPMS and SPMS. In anther embodiment, the invention provides diagnostic methods useful for discriminating MS demyelination patterns, particularly Pattern I and Pattern II MS lesions.

According to some embodiments, the methods of the invention are effected by determining the reactivity of antibodies in a sample obtained from a test subject to a plurality of antigens selected from the group consisting of the antigens listed in Table 1 to Table 4, thereby determining the reactivity pattern of the sample to the plurality of antigens, and comparing the reactivity pattern of said sample to a control reactivity pattern. In one embodiment, a significant difference between the reactivity pattern of said sample compared to a reactivity pattern of a control sample indicates that the subject is afflicted with MS. According to one embodiment, the antigens are selected from Table 1 for the diagnosis of RRMS and the control reactivity pattern is obtained from healthy patients. According to another embodiment, the antigens are selected from Table 2 for the diagnosis of PPMS and the control reactivity pattern is obtained from healthy patients. According to another embodiment, the antigens are selected from Table 3 for the diagnosis of SPMS and the control reactivity pattern is obtained from patients afflicted with RRMS. According to another embodiment, the antigens are selected from Table 4 for discriminating between Pattern I and Pattern II MS lesions (i.e. the sample is tested for Pattern I MS and the control reactivity pattern is obtained from patients having Pattern II MS lesions; or the sample is tested for Pattern II MS and the control reactivity pattern is obtained from patients having Pattern I MS lesions). According to particular embodiments, the antigens are selected from the group consisting of the antigens listed in any one of Tables 1 to Table 4, and said reactivity pattern of said sample indicates the stage of MS in the subject, wherein (i) a significant difference between the control reactivity pattern compared to the reactivity pattern of the sample to the plurality of antigens selected from Table 1 indicates the subject has RRMS; (ii) a significant difference between the control reactivity pattern compared to the reactivity pattern of the sample to the plurality of antigens selected from Table 2 indicates the subject has PPMS; (iii) a significant difference between the control reactivity pattern compared to the reactivity pattern of the sample to the plurality of antigens selected from Table 3 indicates the subject has SPMS; and (iv) a significant difference between the control reactivity pattern compared to the reactivity pattern of the sample to the plurality of antigens selected from Table 4 indicates the subject has Pattern I or Patter II MS lesions.

As used herein, the "reactivity of antibodies in a sample" to "a plurality of antigens" refers to the immune reactivity of each antibody in the sample to a specific antigen selected from the plurality of antigens. The immune reactivity of the antibody to the antigen, i.e. its ability to specifically bind the antigen, may be used to determine the amount of the antibody in the sample. The calculated levels of each one of the tested antibodies in the sample are selectively referred to as the reactivity pattern of the sample to these antigens. For instance, in the Examples below, the reactivity of each antigen was calculated and presented as the scaled mean log intensity of each spot (antigen).

In other embodiments, the methods comprise determining levels of antibodies directed to a plurality of antigens selected from the group consisting of the antigens listed in Table 1 to 4 in a sample obtained from the subject, wherein a statistically significant difference between the level of the antibodies in the sample obtained from the subject compared to a level of the antibodies in a control population, is an indication that the subject is afflicted with a subtype of MS, wherein the subtype of MS is selected from the group consisting of: (i) RRMS wherein said plurality of antigens is selected from the group consisting of the antigens listed in Table 1; (ii) PPMS wherein said plurality of antigens is selected from the group consisting of the antigens listed in Table 2; (iii) SPMS wherein said plurality of antigens is selected from the group consisting of the antigens listed in Table 3; and (iv) a pathologic subtype of MS selected form Pattern I lesions and Pattern II lesions wherein said plurality of antigens is selected from the group consisting of the antigens listed in Table 4.

An antibody "directed to" an antigen, as used herein is an antibody which is capable of specifically binding the antigen. Determining the levels of antibodies directed to a plurality of antigens includes measuring the level of each antibody in the sample, wherein each antibody is directed to a specific antigen of the antigens listed in Tables 1 to 4. This step is typically performed using an immunoassay, as detailed herein.

In other embodiments, the methods comprise determining the levels of a plurality of antibodies in a sample obtained from the subject, each antibody being directed to an antigen selected from the group consisting of the antigens listed in Tables 1 to 4, wherein a significant difference between the levels of the antibodies in the sample obtained from the subject compared to a control level of the antibodies is an indication that the subject is afflicted with a subtype of MS selected from the group consisting of: (i) RRMS wherein said antigen is selected from the antigens listed in Table 1; (ii) PPMS wherein said antigen is selected from the antigens listed in Table 2; (iii) SPMS wherein said antigen is selected from the antigens listed in Table 3; and (iv) a pathologic subtype of MS selected form Pattern I lesions and Pattern II lesions wherein said antigen is selected from the antigens listed in Table 4.

In other embodiments, determining the reactivity of antibodies in said sample to said plurality of antigens, (and the levels of each one of the tested antibodies in the sample) is performed by a process comprising:

contacting the sample, under conditions such that a specific antigen-antibody complex may be formed, with an antigen probe set comprising said plurality of antigens, and quantifying the amount of antigen-antibody complex formed for each antigen probe.

The amount of antigen-antibody complex is indicative of the level of the tested antibody in the sample (or the reactivity of the sample with the antigen).

According to certain embodiments, the present invention provides a method for the differential diagnosis of MS in a subject, the method comprising:

(a) determining the reactivity of antibodies in a sample obtained from the subject to a plurality of antigens selected from the group consisting of the antigens listed in Tables 1, thereby determining the reactivity pattern of the sample to the plurality of antigens, and comparing the reactivity pattern of said sample to a control reactivity pattern obtained from healthy subjects;

(b) determining the reactivity of antibodies in a sample obtained from the subject to a plurality of antigens selected from the group consisting of the antigens listed in Tables 2, thereby determining the reactivity pattern of the sample to the plurality of antigens, and comparing the reactivity pattern of said sample to a control reactivity pattern obtained from healthy subjects;

(c) determining the reactivity of antibodies in a sample obtained from the subject to a plurality of antigens selected from the group consisting of the antigens listed in Tables 3, thereby determining the reactivity pattern of the sample to the plurality of antigens, and comparing the reactivity pattern of said sample to a control reactivity pattern obtained from subjects afflicted with RRMS;

(d) determining the reactivity of antibodies in a sample obtained from the subject to a plurality of antigens selected from the group consisting of the antigens listed in Tables 4, thereby determining the reactivity pattern of the sample to the plurality of antigens, and comparing the reactivity pattern of said sample to a control reactivity pattern obtained from subjects having Pattern I lesions, and/or to a control reactivity pattern obtained from subjects having Pattern II lesions;

wherein:
(i) a significant difference between the reactivity pattern of (a) compared to said control reactivity pattern is an indication that the subject is afflicted with RRMS;
(ii) a significant difference between the reactivity pattern of (b) compared to said control reactivity pattern is an indication that the subject is afflicted with PPMS;
(iii) a significant difference between the reactivity pattern of (c) compared to said control reactivity pattern is an indication that the subject is afflicted with SPMS; and
(iv) a significant difference between the reactivity pattern of (d) compared to a control reactivity pattern obtained from subjects having Pattern I lesions is an indication that the subject is afflicted with Pattern II lesions, and a significant difference between the reactivity pattern of (d) compared to a control reactivity pattern obtained from subjects having Pattern II lesions is an indication that the subject is afflicted with Pattern I lesions.

According to some embodiments, the control reactivity pattern for Table 1 and Table 2 is obtained from healthy control subjects or a stored set of data from healthy control subjects. According to another embodiment, the control reactivity pattern for Table 3 is obtained from subjects afflicted with RRMS or a stored set of data from subjects afflicted with RRMS. According to another embodiment, the control reactivity pattern of the methods and kits of the present invention is obtained from subjects afflicted for other autoimmune or degenerative diseases (e.g. SLE, ALD and AD). According to another embodiment, the reactivity pattern of the sample is compared to a control reactivity pattern previously obtained from the same subject (e.g. kept as a stored set of data), for monitoring disease progression. It should be understood that antibody repertoires of the control sample and the sample obtained from the subject are obtained from the same compartment (e.g. an antibody repertoires of a serum control sample is compared to an antibody repertoires of the sample obtained from the subject's serum).

In another embodiment, there is provided a method of diagnosing a subtype of MS (i.e. RRMS, PPMS, SPMS, lesion Pattern I and lesion Pattern II) in a subject in need thereof, the method comprising:
a) obtaining an antibody-containing biological sample (e.g. serum) from a subject;
b) contacting the sample, under conditions such that an antigen-antibody complex may be formed, with an antigen probe set comprising plurality of antigens as specified in Table 1 to Table 4 herein (or immunogenic fragments, analogs, derivatives and salts thereof); and
c) determining the capacity of antibodies of said sample to specifically bind a plurality of antigens of the antigen probe set;

wherein a significant difference in said capacity compared to the capacity of a control sample (e.g. a sample obtained from a subject not having MS) is indicative that the subject is afflicted with a subtype of MS.

According to another embodiment, the present invention provides a method of diagnosing relapsing remitting multiple sclerosis (RRMS) in a subject, the method comprising determining the reactivity of antibodies in a sample obtained from the subject to a plurality of antigens selected from the group consisting of the antigens listed in Table 1, thereby determining the reactivity pattern of the sample to the plurality of antigens, and comparing the reactivity pattern of said sample to a control reactivity pattern (e.g. a sample obtained from a healthy control), wherein a significant difference between the reactivity pattern of said sample obtained from the subject compared to the reactivity pattern of the control sample is an indication that the subject is afflicted with RRMS.

According to another embodiment, the present invention provides a method of diagnosing primary progressive multiple sclerosis (PPMS) in a subject, the method comprising determining the reactivity of antibodies in a sample obtained from the subject to a plurality of antigens selected from the group consisting of the antigens listed in Table 2, thereby determining the reactivity pattern of the sample to the plurality of antigens, and comparing the reactivity pattern of said sample to a control reactivity pattern (e.g. a sample obtained from a healthy control), wherein a significant difference between the reactivity pattern of said sample obtained from the subject compared to the reactivity pattern of the control sample is an indication that the subject is afflicted with PPMS.

According to another embodiment, the present invention provides a method of diagnosing secondary progressive multiple sclerosis (SPMS) in a subject, the method comprising determining the reactivity of antibodies in a sample obtained from the subject to a plurality of antigens selected from the group consisting of the antigens listed in Table 3, thereby determining the reactivity pattern of the sample to the plurality of antigens, and comparing the reactivity pattern of said sample to a control reactivity pattern (e.g. a sample obtained from a patient afflicted with RRMS), wherein a significant difference between the reactivity pattern of said sample obtained from the subject compared to the reactivity pattern of the control sample is an indication that the subject is afflicted with SPMS.

According to another embodiment, the present invention provides a method of discriminating (i.e. distinguishing) between subjects having lesion pattern I and subjects having lesion pattern II in subjects with MS, the method comprising determining the reactivity of antibodies in a sample obtained from the subject to a plurality of antigens selected from the group consisting of the antigens listed in Table 4, thereby determining the reactivity pattern of the sample to the plurality of antigens, and comparing the reactivity pattern of said sample to a control reactivity pattern. According to certain embodiments, a difference (e.g. an increase) in the reactivity of an antibody to a plurality of antigens selected from the group consisting of 15-ketocholestane, 15a-hydroxycholestene, ganglioside-GM4, tetrasialoganglioside-GQ1B, brain L-α-lysophosphatidylserine, lactosylceramide or 160 kDa neurofilament is an indication that the subject has pattern I lesions and wherein a difference (e.g. an increase) in the reactivity of an antibody to a plurality antigens selected from the group consisting of HSP60, MOG, OSP and PLP peptide epitopes is an indication that the subject has pattern II lesions. In another embodiment, the antibodies for discriminating between subjects having lesion pattern I and subjects having lesion pattern II, are selected form IgM and/or IgG antibodies. In a particular embodiment, all of the antibodies reactive with the antigens listed in Table 4 are IgG antibodies, excluding the antibody reactive with 160 kDa neurofilament, which is an IgM antibody.

In certain embodiments, the test sample and control samples may comprise IgG and/or IgM antibodies. In another embodiment, the reactivity of at least one antibody to a specific antigen, from the plurality of antigens listed in Tables 1 to 4, is up-regulated. In another embodiment, the reactivity of at least one antibody to a specific antigen is down-regulated.

According to particular embodiments, the reactivity pattern for distinguishing RRMS from healthy patients consists of 94 antibody reactivities. According to one embodiment, said reactivity pattern consists of 90 up-regulated reactivities and 4 down-regulated reactivities. In another embodiment, the antibody in the sample obtained from the subject is an IgG antibody wherein the antibody is reactive with an antigen selected from the group consisting of: MBP 31-50; HSP70 481-500; PLP 65-84; and GFAP. In another embodiment, the antibody in the sample obtained from the subject is an IgM antibody wherein the antibody is reactive with an antigen selected from the group consisting of: HSP70 511-530; MBP 41-60; HSP60 286-305; HSP60 496-515; HSP70 151-170; HSP60 526-545; MBP 84-94; OSP 61-80; HSP70 31-50; CNP 286-305; HSP60 255-275; HSP60 106-125; OSP 31-50; P2 61-80; MBP 11-30; HSP60 376-395; HSP70 286-305; HSP60 136-155; HSP70 136-155; P2 46-65; OSP 136-155; P2 1-20; MOG 91-110; HSP60 361-380; HSP70 451-470; HSP70 210-229; HSP60 240-259; HSP60 271-290; OSP 76-95; PLP 178-191; CNP 271-290; P2 76-95; HSP70 631-640; PLP 248-259; HSP60 195-214; CNP 61-80; MOG 196-215; HSP60 46-65; HSP70 195-214; HSP70 436-455; HSP60 166-185; MBP 104-123; MBP 71-92; PLP 180-199; HSP70 255-275; MOBP 166-185; CNP 240-259; HSP60 16-35; HSP60 301-320; MOBP 151-170; CNP 91-110; HSP70 106-125; CNP 406-421; HSP60 421-40; HSP60 61-80; Amyloid beta 10-20; HSP60 511-530; Lactocerebroside; HSP70 406-425; MOG 76-95; HSP70 316-335; HSP60 225-244; HSP60 76-95; MOG 106-125; HSP70 466-485; CNP 1-21; HSP70 166-185; HSP70 121-140; Amyloid beta 1-42; MBP 89-101; CNP 301-320; HSP70 1-20; MBP 51-70; HSP70 496-515; CNP 16-35; CNP 76-95; PLP 10-29; PLP 190-209; HSP60 346-365; HSP60 151-170; HSP70 376-395; bovineMBP; HSP70 556-575; CNP 391-410; MOG 211-230; PLP 220-249; HSP70 616-635; Amyloid beta 1-12; HSP60 556-573; and PLP 250-269.

According to additional embodiments, the reactivity of at least one antibody to a specific antigen selected from the plurality of antigens listed in Table 1, or a subset thereof, is up-regulated, wherein the antigen is selected from HSP70 511-530, MBP 41-60, HSP60 286-305, HSP60 496-515, HSP70 151-170, HSP60 526-545, MBP 84-94, OSP 61-80, HSP70 31-50, CNP 286-305, HSP60 255-275, HSP60 106-125, OSP 31-50, P2 61-80, MBP 11-30, HSP60 376-395, HSP70 286-305, HSP60 136-155, HSP70 136-155, P2 46-65, OSP 136-155, P2 1-20, MOG 91-110, HSP60 361-380, HSP70 451-470, HSP70 210-229, HSP60 240-259, HSP60 271-290, OSP 76-95, PLP 178-191, CNP 271-290, P2 76-95, HSP70 631-640, PLP 248-259, HSP60 195-214, CNP 61-80, MOG 196-215, HSP60 46-65, HSP70 195-214, HSP70 436-455, HSP60 166-185, MBP 104-123, MBP 71-92, PLP 180-199, HSP70 255-275, MOBP 166-185, CNP 240-259, HSP60 16-35, HSP60 301-320, MOBP 151-170, CNP 91-110, HSP70 106-125, CNP 406-421, HSP60 421-40, HSP60 61-80, Amyloid beta 10-20, HSP60 511-530, Lactocerebroside, HSP70 406-425, MOG 76-95, HSP70 316-335, HSP60 225-244, HSP60 76-95, MOG 106-125, HSP70 466-485, CNP 1-21, HSP70 166-185, HSP70 121-140, Amyloid beta 1-42, MBP 89-101, CNP 301-320, HSP70 1-20, MBP 51-70, HSP70 496-515, CNP 16-35, CNP 76-95, PLP 10-29, PLP 190-209, HSP60 346-365, HSP60 151-170, HSP70 376-395, bovineMBP, HSP70 556-575, CNP 391-410, MOG 211-230, PLP 220-249, HSP70 616-635, Amyloid beta 1-12, HSP60 556-573 and PLP 250-26. According to other embodiments the reactivity of at least one antibody to a specific antigen selected from the plurality of antigens listed in Table 1, or a subset thereof, is down-regulated, wherein the antigen is selected from MBP 31-50, HSP70 481-500, PLP 65-84 and GFAP.

According to particular embodiments, the reactivity pattern for distinguishing PPMS from healthy patients consists of 39 antibody reactivities. In another embodiment, the antibody in the sample obtained from the subject is an IgG antibody wherein the antibody is reactive with an antigen selected from the group consisting of: PLP 215-232; HSP70 195-214; HSP70 166-185; bovineMBP; PLP 137-150; MOG 46-65; CNP 406-421; P2 31-50; CNP 1-20; MOG 16-35; P2 76-95; HSP70 466-485; HSP60 76-95; MOG 151-170; P2 1-20; OSP 61-80; PLP 178-191; HSP70 16-35; HSP70 121-140; and OSP 1-20. In another embodiment, the antibody in the sample obtained from the subject is an IgM antibody wherein the antibody is reactive with an antigen selected from the group consisting of: PLP 215-232; mMBP; smLPS; HSP70 210-229; Chondroitin 4-Sulfate; bovineMBP; Neurofilament 68 kDa; Beta Amyloid; AB 1-40; PLP 161-180; PLP 40-59; PLP 137-150; Secreted APPalpha; gpMBP; MBP 104-123; SOD; CNP 1-20; ecLPS; and MOBP 61-80.

According to additional embodiments, the reactivity of at least one antibody to a specific antigen selected from the plurality of antigens listed in Table 2, or a subset thereof, is up-regulated, wherein the antigen is selected from Beta Amyloid, HSP70 466-485, AB 1-40, PLP 161-180, PLP 40-59, PLP 137-150, HSP60 76-95, MOG 151-170, P2 1-20, OSP 61-80, Secreted APPalpha, PLP 178-191, gpMBP, HSP70 16-35, MBP 104-123, SOD, CNP 1-20, ecLPS, HSP70 121-140, MOBP 61-80 and OSP 1-20. According to other embodiments the reactivity of at least one antibody to a specific antigen selected from the plurality of antigens listed in Table 2, or a subset thereof, is down-regulated, wherein the antigen is selected from PLP 215-232, PLP 215-232, mMBP, HSP70 195-214, smLPS, HSP70 210-229, Chondroitin 4-Sulfate, HSP70 166-185, bovineMBP, PLP 137-150, MOG 46-65, CNP 406-421, P2 31-50, CNP 1-20, MOG 16-35, P2 76-95 and Neurofilament 68 kDa.

According to particular embodiments, the reactivity pattern for distinguishing SPMS from healthy patients consists of 66 antibody reactivities. In another embodiment, the antibody in the sample obtained from the subject is an IgM antibody wherein the antibody is reactive with an antigen selected from the group consisting of: MOG 61-80; HSP60

376-395; MOG 31-50; CNP 361-380; Amyloid beta 1-23; CNP 346-365; HSP60 496-515; OSP 1-20; HSP60 511-530; OSP 61-80; HSP60 286-305; CNP 240-259; HSP70 601-620; HSP60 210-229; HSP60 451-470; MOBP 166-185; HSP60 166-185; MBP 138-147; CNP 195-214; MBP 1-20; HSP60 526-545; P2 1-20; HSP70 286-305; MBP 155-178; P2 46-65; HSP60 195-214; P2 31-50; HSP60 271-290; HSP60 136-155; CNP 286-305; HSP70 210-229; HSP70 136-155; PLP 150-163; HSP70 166-185; HSP60 255-275; HSP60 16-35; bovineMBP; CNP 181-199; CNP 121-140; Asialoganglioside-GM2; Amyloid beta 1-12; OSP 121-140; Secreted APPbeta; Cardiolipin; HSP70 406-425; and IgM_PLP 1-19. In another embodiment, the antibody in the sample obtained from the subject is an IgG antibody wherein the antibody is reactive with an antigen selected from the group consisting of: HSP60 361-380; Amyloid beta 17-40; Cholesterol; Amyloid beta 1-42; PLP 80-99; PLP 65-84; PLP 40-59; PLP 1-19; PLP 151-173; HSP70 421-440; huMBP; MOBP 16-35; CNP 16-35; RBP; HSP70 331-350; OSP 121-140; MBP 113-132; beta Crystallin; CNP 240-259; and PLP 178-191.

According to additional embodiments, the reactivity of at least one antibody to a specific antigen selected from the plurality of antigens listed in Table 3, or a subset thereof, is up-regulated, wherein the antigen is selected from Amyloid beta 17-40, Cholesterol, Amyloid beta 1-42, PLP 80-99, PLP 65-84, PLP 40-59, PLP 1-19, PLP 1-19, PLP 151-173, HSP70 421-440, huMBP, MOBP 16-35, CNP 16-35, RBP, HSP70 331-350, OSP 121-140, MBP 113-132, beta Crystallin, CNP 240-259 and PLP 178-191. According to other embodiments the reactivity of at least one antibody to a specific antigen selected from the plurality of antigens listed in Table 3, or a subset thereof, is down-regulated, wherein the antigen is selected MOG 61-80, HSP60 376-395, MOG 31-50, CNP 361-380, Amyloid beta 1-23, CNP 346-365, HSP60 496-515, OSP 1-20, HSP60 511-530, OSP 61-80, HSP60 286-305, CNP 240-259, HSP70 601-620, HSP60 210-229, HSP60 451-470, MOBP 166-185, HSP60 166-185, MBP 138-147, CNP 195-214, MBP 1-20, HSP60 526-545, P2 1-20, HSP70 286-305, MBP 155-178, P2 46-65, HSP60 195-214, P2 31-50, HSP60 271-290, HSP60 136-155, CNP 286-305, HSP70 210-229, HSP70 136-155, PLP 150-163, HSP70 166-185, HSP60 255-275, HSP60 16-35, bovineMBP, CNP 181-199, CNP 121-140, Asialoganglioside-GM2, Amyloid beta 1-12, OSP 121-140, Secreted APPbeta, Cardiolipin, HSP70 406-425 and HSP60 361-380.

In some embodiments, the methods of the present invention employ an antigen microarray system for informatically characterizing informative patterns of antibodies as specific biomarkers for subtypes of MS, as detailed herein.

Antibodies, Samples and Immunoassays

Antibodies, or immunoglobulins, comprise two heavy chains linked together by disulfide bonds and two light chains, each light chain being linked to a respective heavy chain by disulfide bonds in a "Y" shaped configuration. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention (for example as immunoassay reagents, as detailed herein) are chimeric antibodies; recombinant and engineered antibodies, and fragments thereof.

Exemplary functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens. An "antigenic peptide" is a peptide which is capable of specifically binding an antibody.

In another embodiment, detection of the capacity of an antibody to specifically bind an antigen probe may be performed by quantifying specific antigen-antibody complex formation. The term "specifically bind" as used herein means that the binding of an antibody to an antigen probe is not competitively inhibited by the presence of non-related molecules.

In certain embodiments, the method of the present invention is performed by determining the capacity of a peptide of the invention to specifically bind antibodies of the IgG isotype, or, in other embodiments, antibodies of the IgM or IgE isotypes, isolated from a subject.

Methods for obtaining suitable antibody-containing biological samples from a subject are well within the ability of those of skill in the art. Typically, suitable samples comprise whole blood and products derived therefrom, such as plasma and serum. In other embodiments, other antibody-containing samples may be used, e.g. CSF, urine and saliva samples. A non-limiting example of obtaining serum samples from test subjects is presented in the Examples section below.

In accordance with the present invention, any suitable immunoassay can be used with the subject peptides. Such techniques are well known to the ordinarily skilled artisan and have been described in many standard immunology manuals and texts. In certain preferable embodiments, determining the capacity of the antibodies to specifically bind the antigen probes is performed using an antigen probe array-based method. Preferably, the array is incubated with suitably diluted serum of the subject (e.g. diluted 1:10) so as to allow specific binding between antibodies contained in the serum and the immobilized antigen probes, washing out unbound serum from the array, incubating the washed array with a detectable label-conjugated ligand of antibodies of the desired isotype, washing out unbound label from the array, and measuring levels of the label bound to each antigen probe.

According to some aspects the methods of the present invention may be practiced using antigen arrays as disclosed in WO 02/08755 and U.S. 2005/0260770 to some of the inventors of the present invention. WO 02/08755 is directed to a system and an article of manufacture for clustering and thereby identifying predefined antigens reactive with undetermined immunoglobulins of sera derived from patient subjects in need of diagnosis of disease or monitoring of treatment. Further disclosed are diagnostic methods, and systems useful in these methods, employing the step of clustering a subset of antigens of a plurality of antigens, said subset of antigens being reactive with a plurality of antibodies being derived from a plurality of patients, and associating or disassociating the antibodies of a subject with the resulting cluster. U.S. Pat. App. Pub. No. 2005/0260770 to some of the inventors of the present invention discloses an antigen array system and diagnostic uses thereof. The application provides a method of diagnosing an immune disease, particularly diabetes type 1, or a predisposition thereto in a subject, comprising determining a capacity of immunoglobulins of the subject to specifically bind each antigen probe of an antigen probe set. The teachings of said disclosures are incorporated in their entirety as if fully set forth herein.

In other embodiments, various other immunoassays may be used, including, without limitation, enzyme-linked immunosorbent assay (ELISA), flow cytometry with multiplex beads (such as the system made by Luminex), surface plasmon resonance (SPR), elipsometry, and various other immunoassays which employ, for example, laser scanning, light detecting, photon detecting via a photo-multiplier, photographing with a digital camera based system or video system, radiation counting, fluorescence detecting, electronic, magnetic detecting and any other system that allows quantitative measurement of antigen-antibody binding.

Various methods have been developed for preparing arrays suitable for the methods of the present invention. State-of-the-art methods involves using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. Conveniently, the glass surface is first activated by a chemical treatment that leaves a layer of reactive groups such as epoxy groups on the surface, which bind covalently any molecule containing free amine or thiol groups. Suitable supports may also include silicon, nitrocellulose, paper, cellulosic supports and the like.

Preferably, each antigen probe, or distinct subset of antigen probes of the present invention, which is attached to a specific addressable location of the array is attached independently to at least two, more preferably to at least three separate specific addressable locations of the array in order to enable generation of statistically robust data.

In addition to antigen probes of the invention, the array may advantageously include control antigen probes or other standard chemicals. Such control antigen probes may include normalization control probes. The signals obtained from the normalization control probes provide a control for variations in binding conditions, label intensity, "reading" efficiency and other factors that may cause the signal of a given binding antibody-probe ligand interaction to vary. For example, signals, such as fluorescence intensity, read from all other antigen probes of the antigen probe array are divided by the signal (e.g., fluorescence intensity) from the normalization control probes thereby normalizing the measurements. Normalization control probes can be bound to various addressable locations on the antigen probe array to control for spatial variation in antibody-ligand probe efficiency. Preferably, normalization control probes are located at the corners or edges of the array to control for edge effects, as well as in the middle of the array.

The labeled antibody ligands may be of any of various suitable types of antibody ligand. Preferably, the antibody ligand is an antibody which is capable of specifically binding the Fc portion of the antibodies of the subject used. For example, where the antibodies of the subject are of the IgM isotype, the antibody ligand is preferably an antibody capable of specifically binding to the Fc region of IgM antibodies of the subject.

The ligand of the antibodies of the subject may be conjugated to any of various types of detectable labels. Preferably the label is a fluorophore, most preferably Cy3. Alternately, the fluorophore may be any of various fluorophores, including Cy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of blood serum or plasma or a dilution thereof (e.g. 1:10 dilution), the antibodies may be subjected to any desired degree of purification prior to being tested for their capacity to specifically bind antigen probes. The method of the present invention may be practiced using whole antibodies of the subject, or antibody fragments of the subject which comprises an antibody variable region.

Data Analysis

Advantageously, the methods of the invention may employ the use of learning and pattern recognition analyzers, clustering algorithms and the like, in order to discriminate between reactivity patterns of subjects having a subtype of MS to control subjects. For example, the methods may include determining the reactivity of antibodies in a test sample to a plurality of antigens, and comparing the resulting pattern to the reactivity patterns of negative and positive control samples using such algorithms and/or analyzers.

In certain embodiments, one or more algorithms or computer programs may be used for comparing the amount of each antibody quantified in the test sample against a predetermined cutoff (or against a number of predetermined cutoffs). Alternatively, one or more instructions for manually performing the necessary steps by a human can be provided.

Algorithms for determining and comparing pattern analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flowchart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

Advantageously, the discrimination between patients having a form (e.g. subtype) of MS and control individuals (e.g. healthy individuals or individuals afflicted with another form of MS) is performed in multi-dimensional space. For example, a diagnostic test performed with an antigen array consisting of the antigens listed in Table 1 herein is performed in 94 dimensions. Conveniently, such analysis is performed by dividing the space into a region characteristic of patients and one for control individuals, as exemplified below.

The following examples are presented in order to more fully illustrate some embodiments of the invention. They should, in no way be construed, however, as limiting the broad scope of the invention.

EXAMPLES

Procedures

ELISA

Antigens (1 mg/ml in phosphate-buffered saline for proteins, 5 mg/ml in ethanol for lipids) were coated in 96-well Maxisorp ELISA plates (NalgeNunc, Rochester, N.Y.), and ELISA was performed as described (Quintana et al., *J Autoimmun* 21, 65-75, 2003).

Antigen Microarray Chips

Antigens diluted in PBS were placed in 384-well plates at a concentration of 0.1-1 milligram/ml. A robotic MicroGrid arrayer with solid spotting pins of 0.2 mm in diameter (BioRobotics, Cambridge, U.K.) was used to spot the antigens onto ArrayIt SuperEpoxi microarray substrate slides (TeleChem, Sunnyvale, Calif.). Each antigen was spotted in three or four replicates. The spotted microarrays were stored at 4° C.

The chips were washed with PBS, blocked for 1 h at 37° C. with 1% BSA, and incubated for 2 hours at 37° C. with a 1:10 dilution of the test serum in blocking buffer under a coverslip in a humid environment. The arrays were then washed and incubated for 45 min at 37° C. with a 1:500 dilution mixture of goat anti-human IgG Cy3-conjugated antibody and a goat anti-human IgM conjugated to Cy5, (both purchased from Jackson ImmunoResearch, West Grove, Pa. The arrays were scanned with a ScanArray 4000× scanner (GSI Luminomics, Billerica, Mass., USA) and the IgM and IgG results were recorded separately. The results were recorded as TIFF files.

Image and Data Processing

The pixels that comprised each spot in the TIFF files and the local background were identified by using histogram segmentation. The intensity of each spot and its local background were calculated as the mean of the corresponding pixel intensities. None of the spots containing antigens showed saturation. Technically faulty spots were identified by visual inspection and were removed from the data set. For each spot, the local background intensity was subtracted from the spot intensity. Spots with negative intensities were removed from the data set.

A log-base-2 transformation of the intensities resulted in reasonably constant variability at all intensity levels. The log intensity of each antigen was calculated as the mean of the log intensities of the replicates on each slide. The coefficient of variability between replicates on each array was under 10%. To remove overall differences in intensities between arrays, the mean log intensity of each antigen on each array was scaled by subtracting the median of the mean log intensities of all antigens on the array. The scaled mean log intensity of an antigen is denoted the reactivity of the antigen.

Raw data were normalized and analyzed using the GeneSpring software (Silicon Genetics, Redwood City, Calif.). Antigen reactivity was defined by the mean intensity of binding to the replicates of that antigen on the microarray. The data were analyzed with the non-parametric Wilcoxon-Mann-Whitney test, using the Benjamini and Hochberg method with a false discovery rate of 0.05 (analysis of RRMS and PPMS samples) or 0.2 (analysis of immunopathology pattern I and II samples) to determine significance. The leave-one-out cross-validation analysis (LOOCV) in the training set and the classification of samples on the test set was carried out using a support vector machine that classified samples based on the antibody reactivities identified to be discriminatory on the training set.

Patients and Sera Samples

Serum samples were collected at the Partners MS Center from untreated RRMS during clinical remission, PPMS patients or HC. The patients did not present with other autoimmune disorders. Sixty-two patients with biopsy proven CNS inflammatory demyelinating disease were identified from an original cohort of 780 central nervous system inflammatory demyelinating disease (CNS IDD) biopsy cases belonging to the MS Lesion Project (MSLP). The MSLP database consists of a unique collection of biopsy-proven CNS IDD cases with detailed pathological, clinical, imaging and serological material (NMSS RG3184-B-3-02). Active demyelinating lesions were classified into either pattern I or II based on previously published criteria (Lucchinetti et al., 2000). Sera and face to face neurological assessment was obtained on all included patients at the time of follow-up. Paired CSF and serum samples were collected at the University Hospital, School of Medicine, University of Sevilla from RRMS patients with confirmed intratecal IgG secretion and IgG oligoclonal bands. The clinical characteristics of the patients, pathological cohorts and healthy controls are listed in Table 6 herein below. Control samples were pair-wise matched for age, gender and ethnicity.

TABLE 6

Characteristics of the patients and healthy controls (HC)

| Group | N | Gender (F/M) | Age | Disease Duration | EDSS |
|---|---|---|---|---|---|
| RRMS (USA) | 39 | 31/8 | 42 (22-58) | 13.0 (6.0-27.0) | 1.5 (0.0-3.5) |
| RRMS (Spanish Cohort) | 51 | 33/17 | 44 (20-55) | 2.3 (0.0-24.0) | 1.3 (0.0-3.5) |
| SPMS | 30 | 23/7 | 50 (31-64) | 8 (2.0-27.0) | 6.0. (1.5-8.5) |
| PPMS | 37 | 20/17 | 55 (34-73) | 4.5 (0.0-25.0) | 6.0. (1.5-9.5) |
| Pattern I | 15 | 10/5 | 42 (20-70) | 4.1 (1.4-16.1) | 3 (0.0-7.0) |
| Pattern II | 53 | 25/28 | 44 (20-71) | 3.3 (0.6-37.8) | 2 (0.0-8.0) |
| HC | 30 | 18/12 | 51 (20-72) | NA | NA |

As used herein "EDSS" refers to the Kurtzke Expanded Disability Status Scale (EDSS), which is known in the art as a method for quantifying disability in multiple sclerosis. The EDSS quantifies disability in eight functional systems (i.e. pyramidal, cerebellar, brainstem, sensory, bowel and bladder, visual, cerebral, and other systems) and allows neurologists to assign a functional system score in each system. EDSS steps 1.0 to 4.5 refer to people with MS who are fully ambulatory. EDSS steps 5.0 to 9.5 are defined by the impairment to ambulation.

Serum and CSF samples from Alzheimer's disease patients were provided by Dr. Denis Selkoe of the Center for Neurologic Diseases, Brigham and Women's Hospital, Harvard Medical School, Boston, Mass. Serum samples from SLE patients were provided by Dr. Peter H. Schur of the Department of Rheumatology/Immunology, Brigham and Women's Hospital, Boston, Mass.

The samples were collected as follows: blood samples were collected into sterile test tubes and allowed to clot, by leaving the test tubes at room temperature for 30 minutes. Next, the tubes were centrifuged at 2000 g for 15 minutes. The liquid phase was transferred to new test tubes, divided into aliquots and stored at $\leq -20°$ C.

Antigens

Peptides were synthesized at the Biopolymers Facility of the Department of Biological Chemistry and Molecular Pharmacology of Harvard Medical School (HMS). Recombinant proteins and lipids were purchased from Sigma (St. Louis, Mo., USA), Abnova (Taipei City, Taiwan), Matreya LLC (Pleasant Gap, Pa., USA), Avanti Polar Lipids (Alabaster, Ala., USA), Calbiochem (San Diego, Calif., USA), Chemicon (Temecula, Calif., USA), GeneTex (San Antonio, Tex., USA), Novus Biologicals (Littleton, Colo., USA) Assay Designs (Ann Arbor, Mich., USA), ProSci Inc. (Poway, Calif., USA), EMD Biosciences (San Diego, Calif., USA), Cayman Chemical (Ann Arbor, Mich., USA), HyTest (Turku, Finland), Meridian Life Science (Memphis, Tenn. USA) and Biodesign International (Saco, Me., USA).

The antigens used in the construction of antigen microarrays were as follows: Heat shock Proteins 27 kDa (HSP27), HSP32, HSP40, HSP47, HSP60, *M. tuberculosis* HSP65, HSP70, *M. tuberculosis* HSP71, HSP90 and GroEL (all purchased from Stressgen); HSP60 peptides consisting of amino acids 106-125, 1-20, 121-140, 136-155, 151-170, 16-35, 166-185, 181-199, 195-214, 210-229, 225-244, 240-259, 255-275, 271-290, 286-305, 301-320, 31-50, 316-335, 331-350, 346-365, 361-380, 376-395, 391-410, 406-425, 421-440, 436-455, 451-470, 466-485, 46-65, 481-500, 496-515, 511-530, 526-545, 541-560, 556-573, 61-80, 76-95 and 91-110 (all synthesized at Biopolymers Facility, HMS); HSP70 peptides consisting of amino acids 106-125, 1-20, 121-140, 136-155, 151-170, 16-35, 166-185, 181-199, 195-214, 210-229, 225-244, 240-259, 255-275, 271-290, 286-305, 301-320, 31-50, 316-335, 331-350, 346-365, 361-380, 376-395, 391-410, 406-425, 421-440, 436/55, 451-470, 466-485, 46-65, 481-500, 496-515, 511-530, 526-545, 541-560, 556-575, 571-590, 586-605, 601-620, 616-635, 61-80, 631-640, 76-95 and 91-110 (all synthesized at Biopolymers Facility, HMS).

CNS proteins 2',3'-cyclic nucleotide 3'-phosphodiesterase peptides (CNP) consisting of amino acids 106-125, 1-20, 121-140, 136-155, 151-170, 16-35, 166-185, 181-200, 195-215, 211-230, 226-245, 241-260, 256-275, 271-290, 286-305, 301-320, 31-50, 316-335, 331-350, 346-365, 361-380, 376-395, 391-410, 406-421, 46-65, 61-80, 76-95 and 91-110 (all synthesized at Biopolymers Facility, HMS); Acetyl Cholinesterase, ADAM-10, beta-Cristallin, bovine Myelin Basic Protein, Brain Extract I, Brain Extract II, Brain Extract III, guinea pig Myelin Basic Protein, human Myelin Basic Protein (all purchased from Sigma Aldrich); alpha-Cristallin (purchased from Stressgen); Glial Filament Acidic Protein (GFAP) (purchased from Research Diagnostic); Myelin-Associated Oligodendrocytic Basic Protein (MOBP) peptides consisting of amino acids 106-125, 1-20, 121-140, 136-155, 151-170, 16-35, 166-185, 181-200, 31-50, 46-65, 61-80, 76-95 and 91-110 (all synthesized at Biopolymers Facility, HMS); Myelin/oligodendrocyte glycoprotein (MOG) peptides consisting of amino acids 106-125, 1-20, 121-140, 136-

155, 151-170, 16-35, 166-185, 181-200, 196-215, 211-230, 226-247, 31-50, 35-55, 46-65, 61-80, 76-95 and 91-110 (all synthesized at Biopolymers Facility, HMS); murine Myelin Basic Protein (mMBP) and Myelin Associated Glycoprotein (purchased from Sigma Aldrich); Myelin Basic Protein (MBP) peptides consisting of amino acids 104-123, 11-30, 113-132, 1-20, 121-138, 124-142, 138-147, 141-161, 143-168, 155-178, 26-35, 31-50, 41-60, 51-70, 61-80, 71-92, 84-94, 89-101 and 93-112 (all synthesized at Biopolymers Facility, HMS); Myelin Protein 2 (P2) peptides consisting of amino acids 106-125, 1-20, 121-132, 16-35, 31-50, 46-65, 61-80, 76-95 and 91-110 (synthesized at Biopolymers Facility, HMS); Neurofilament 160 kd, Neurofilament 200 kd, Neurofilament 68 kd (all purchased from Chemicon); Neuronal Enolase (purchased from Calbiochem); Nicastrin (purchased from GeneTex); NMDA receptor (purchased from Novus Biologicals); NOGO (purchased from Sigma Aldrich); Olygodendrocyte-Specific Protein (OSP) peptides consisting of amino acids 106-125, 1-20, 121-140, 136-155, 151-170, 16-35, 166-185, 181-199, 195-217, 31-50, 46-65, 61-80, 76-95 and 91-110 (all synthesized at Biopolymers Facility, HMS); Proteolipid Protein (Abnova); Proteolipid Protein peptides consisting of amino acids 100-119, 10-29, 110-129, 1-19, 125-141, 137-150, 137-154, 150-163, 151-173, 158-166, 161-180, 178-191, 180-199, 190-209, 20-39, 205-220, 215-232, 220-239, 220-249, 248-259, 250-269, 265-277, 35-50, 40-59, 50-69, 65-84, 80-99 and 91-110 (all synthesized at Biopolymers Facility, HMS); Retinol Binding Protein, Super Oxide Dismutase, beta Synuclein, gamma Synuclein (Sigma Aldrich); and S100beta protein (Assay Designs).

Tissue antigens (purchased from ProSci Inc.): Amydgala, Amydgala AD, Brain lysate, Brain Tissue Membrane, Cerebellar pedunculus, Cerebral meninges, Corpus Callosum, Corpus Callosum AD, Diencephalon, Fetal brain, Frontal lobe, Frontal lobe AD, Hippocampus, Hippocampus AD, Insula, Occipital lobe, Occipital lobe AD, Olfactory region, Optic Nerve, Parietal lobe, Parietal lobe AD, Pons, Pons AD, Postcentral gyrus, Postcentral gyrus AD, Precentral gyrus, Precentral gyrus AD, Spinal cord, Temporal lobe, Temporal lobe AD, Thalamus and Thalamus AD.

AD related antigens: Amyloid beta (AB), AB 10-20, AB 1-12, AB 12-28, AB 1-23, AB 1-38, AB 17-40, AB 25-35, AB 34-42, Amyloid bri protein precursor 227, Amyloid DAN Protein, Fragment 1-34, Amyloid Precursor Protein, Amyloid protein no AB component, Secreted amyloid precursor protein (SAP) beta, Tau isoform variant 0N3R, Tau isoform variant 1N3R, Tau isoform variant 0N4R, Tau isoform variant 2N3R, Tau phospho Ser412, Tau phospho Ser441 and Tau phospho Thr181 (all purchased from Sigma Aldrich); and Tau Protein human (purchased from EMD Biosciences).

Lipid antigen: 1 Palmitoyl-2-(5' oxo-Valeroyl)-sn-Glycero-3-Phosphocholine, 15a-hydroxycholestene, 15-ketocholestane, 15-ketocholestene, 1-Palmitoil-2-(9' oxo-Nonanoyl)-sn-Glycero-3-Phosphocholine, 1-Palmitoil-2-Azelaoyl-sn-Glycero-3-Phosphocholine, 1-Palmitoil-2-Glutaroyl-sn-Glycero-3-Phosphocholine, 5α-cholestane-3 β,15 α-diol, Brain ceramides, Brain D-erythrosphingosine, Brain lysophosphatidylethanolamine, Brain L-α-lysophosphatidylserine, Brain L-α-phosphatidylcholine, Brain L-α-phosphatidyl-ethanolamine, Brain L-α-phosphatidylserine, Brain polar lipid extract, Brain sphingomyelin, Brain sulfatide, Brain total lipid extract, Gangliotetraosylceramide asialo-GM1, Total brain gangliosides and Total cerebroside (all purchased from Avanti Polar Lipids); 9(S)-HODE, (±)9-HODE, Isoprostane F2 I (Cayman Chemical); Asialoganglioside-GM1, Asialoganglioside-GM2, Cardiolipin, Ceramide, Ceramide 1-phosphate, Cholesterol, Disialogaglioside-GD1B, Disialogaglioside-GD2, Disialoganglioside GD1a, Galactocerebrosides, Ganglioside Mixture, HDL, Hexacosanoic acid (26), Hydroxy fatty acid ceramide, Lactocerebrosides, LDL, Lipid A, diphosphoryl, from *Salmonella enterica*, Lipopolysaccharides from *Escherichia coli*, Lipopolysaccharides from *Pseudomona aeruginosa*, Lipopolysaccharides from *Salmonella enterica*, Monosialoganglioside GM1, Monosialoganglioside GM2, N-Hexanoyl-D-sphingosin, Non-hydroxy fatty acid ceramide, Phosphatidylinositol-4 phosphate, Squalene, Sulfatides, Tetracosanoic acid (24), TNPAL Galactocerebrosideand Trisialoganglioside-GT1B (Sigma Aldrich); Disialoganglioside GD3 and Trisialoganglioside GT1a (HyTest); Fucosyl-GM1, Ganglioside-GM4, Lactosylceramide, Lyso-GM1 and Tetrasialoganglioside-GQ1B (Calbiochem); and Monosialoganglioside GM3 (all purchased from Meridian).

Example 1

Conditions to Detect Specific Microarray Autoantibodies in MS

Antigen microarrays were constructed using 362 myelin and inflammation-related antigens (listed herein above) that encompassed CNS antigens suspected of being associated with MS, CNS antigens suspected of being associated with other neurological diseases and heat shock proteins (HSP). Antigens were spotted on epoxy glass slides using a robotic arrayer as previously described (Quintana et al., 2004).

The sensitivity of the antigen-microarray technique was compared to that of a standard ELISA technique using commercially available monoclonal and polyclonal antibodies directed against CNS, HSP and lipid antigens. The antigen microarray detected antigen reactivities at $log_{10}$ dilutions that were 1-2 logs greater than the reactivities detected by using the ELISA method (Table 7). Thus, the antigen microarray appears to be more sensitive than a standard ELISA assay.

TABLE 7

Comparison of antigen microarray with ELISA

| Dilution | HSP60-1 | | HSP60-2 | | HSP60-3 | |
|---|---|---|---|---|---|---|
| | Array | ELISA | Array | ELISA | Array | ELISA |
| 1:100 | MAX | 1.98 | MAX | 1.77 | 45,693 | 1.64 |
| 1:1,000 | MAX | 1.24 | MAX | 1.29 | 23,731 | 0.73 |
| 1:10,000 | 48,930 | 0.64 | 39,837 | 0.83 | 5,375 | 0.29 |
| 1:100,000 | 31,513 | 0 | 3,489 | 0.17 | 1,858 | 0 |
| 1:1,000,000 | 2,380 | 0 | 742 | 0 | 0 | 0 |
| 1:10,000,000 | 0 | 0 | 0 | 0 | 0 | 0 |

| | MBP | | PLP | | GM4 | |
|---|---|---|---|---|---|---|
| | Array | ELISA | Array | ELISA | Array | ELISA |
| 1:100 | MAX | 1.51 | MAX | 2.31 | MAX | 3.13 |
| 1:1,000 | 46,314 | 1.09 | MAX | 1.16 | 29,857 | 1.61 |
| 1:10,000 | 26,384 | 0.75 | 42,084 | 0.53 | 16,749 | 0.5 |
| 1:100,000 | 14,423 | 0.31 | 12,294 | 0.3 | 7,313 | 0 |
| 1:1,000,000 | 6,916 | 0 | 6,837 | 0 | 1,598 | 0 |
| 1:10,000,000 | 1,810 | 0 | 1,332 | 0 | 0 | 0 |

Figure 1B:
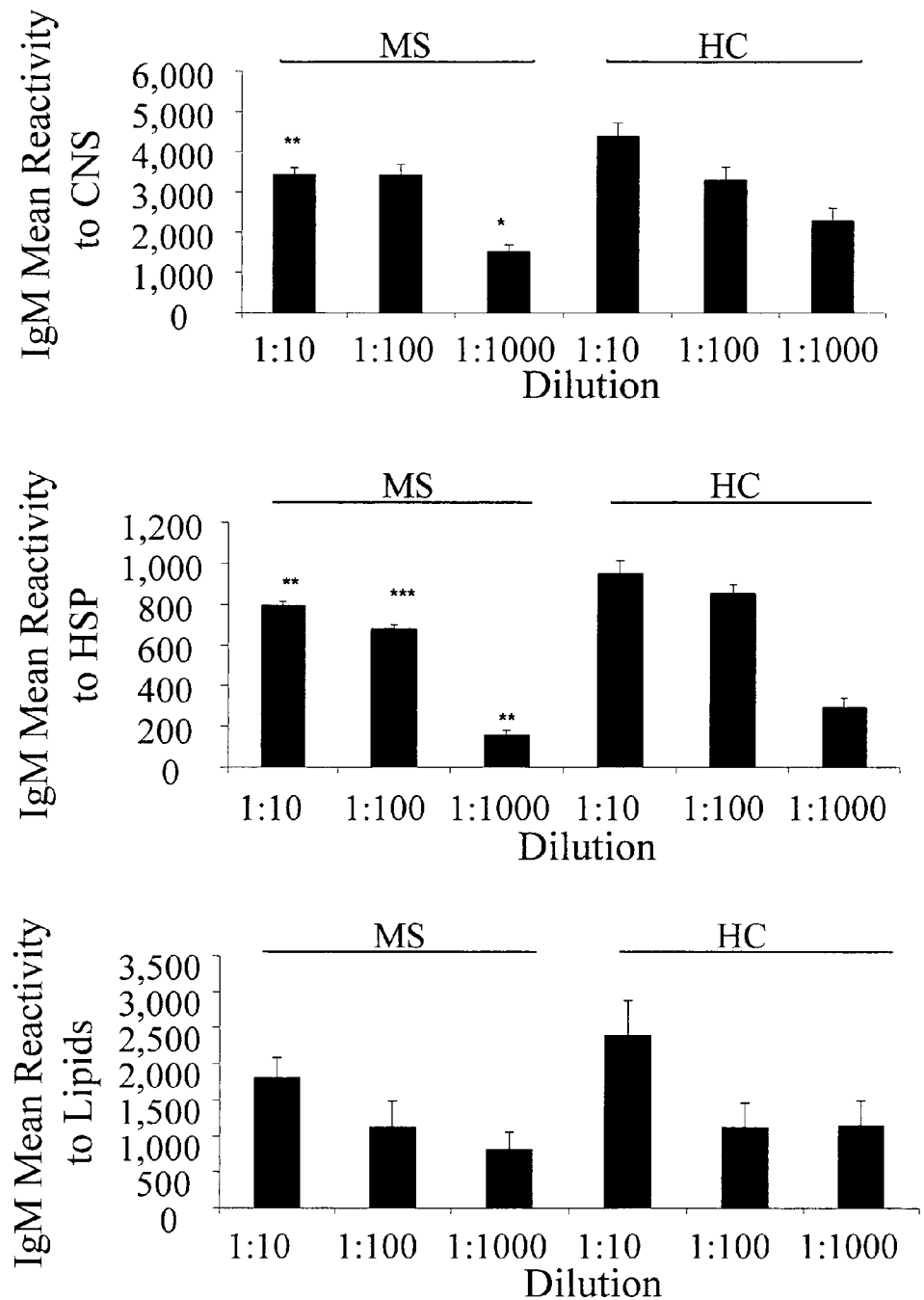

To determine which serum dilution was optimal to investigate immune signatures in MS, the reactivity of healthy controls (HC) and RRMS subjects was analyzed at dilutions of 1:10, 1:100 and 1:1000 for both IgG and IgM antibodies. As shown in FIG. 1A, in MS, the mean IgG antibody reactivity to CNS antigens, lipids and heat shock proteins (HSP) was highest at 1:10 as compared to 1:100 and 1:000 where minimal reactivity was observed (P<0.0001, two-way ANOVA). The mean IgG reactivity was also highest at a 1:10 dilution in HC (P<0.0001, two-way ANOVA), but this reactivity was less than that manifested in MS subjects (P<0.001, P<0.001 and P<0.05 for CNS antigens, lipids and heat shock proteins respectively, two-way ANOVA); indeed, at dilutions of 1:100 and 1:1000, there were no differences between the magnitude of IgG reactivity in MS compared to HC. The IgM reactivities in controls were as high, if not higher than in MS subjects (FIG. 1B). This is consistent with the observation that healthy humans are born with IgM autoantibodies to myelin antigens and heat shock proteins (Merbl et al., 2007, *J Clin Invest* 117, 712-8). Since MS subjects manifested significantly elevated serum IgG autoantibodies at a 1:10 dilution, serum antibody patterns with antigen microarrays were investigated using this dilution.

Figure 1C:
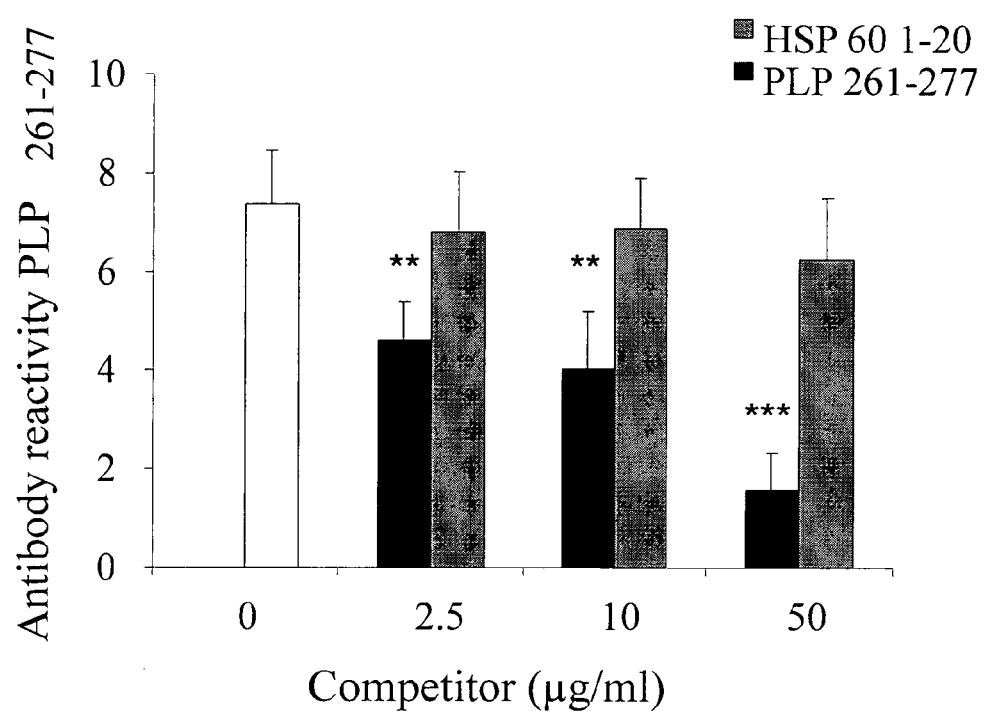

To establish that the reactivity detected at a 1:10 dilution was specific, inhibition experiments were carried out and demonstrated that reactivity to $PLP_{261-277}$ on the antigen array could be inhibited by pre-incubation of the serum with excess unbound $PLP_{261-277}$, but not with a control peptide, $HSP60_{1-20}$ (FIG. 1C).

Example 2

Autoantibody Pattern Analysis Identifies an Immune Signature for RRMS

To investigate if unique antibody signatures in RRMS could be identified, the antibody repertoire in 38 patients with RRMS and 30 healthy controls (HC) subjects was studied. Samples were allocated into a training set (24 RRMS and 20 controls) and a randomly selected test set (14 RRMS and 10 controls). The training set was used to determine whether patterns of antibody reactivity that could discriminate RRMS from control samples may be identified. If such patterns were found, they were then validated on the test set. The training set was analyzed using the Wilcoxon-Mann-Whitney test; the false discovery rate was controlled using the method of Benjamini and Hochberg (Cohen, I. R., 2007, *Nat Rev Immunol.* 7, 569-74). The clinical characteristics of the patients and HC are listed in Table 6.

Figure 2A:
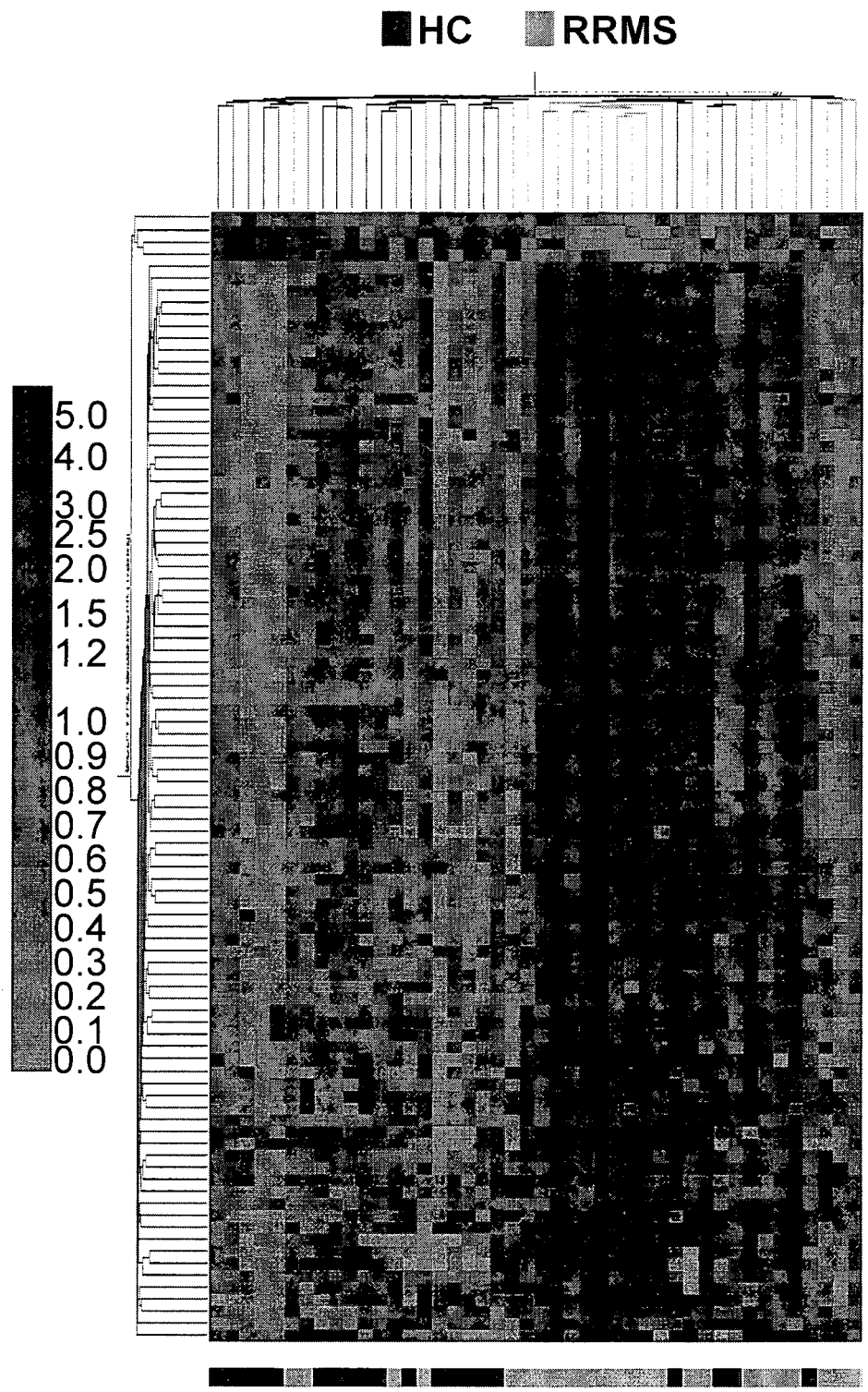
FIGS. 2A and 2B show antibody reactivities discriminating RRMS (FIG. 2A) or PPMS (FIG. 2B) from HC. Heatmap in which each column represents a patient, color-coded at the bottom to indicate whether it corresponds to a RRMS (FIG. 2A), PPMS (FIG. 2A) or HC (FIG. 2A and FIG. 2B) sample, and each row shows the normalized antibody reactivity (detailed in the Examples 2 and 3 below) to an antigen according to the colorimetric scale shown on the left.

As shown in the heatmap in FIG. 2A, a pattern of reactivity that distinguished RRMS from HC (P<0.0001, Fisher's exact test) was identified. The antibody reactivities included in the heatmap shown in FIG. 2A are listed herein (in the same order as in the heatmap, i.e. from top to bottom): IgG_MBP 31-50; IgG_HSP70 481-500; IgG_PLP 65-84; IgG_GFAP; IgM_HSP70 511-530; IgM_MBP 41-60; IgM_HSP60 286-305; IgM_HSP60 496-515; IgM_HSP70 151-170; IgM_HSP60 526-545; IgM_MBP 84-94; IgM_OSP 61-80; IgM_HSP70 31-50; IgM_CNP 286-305; IgM_HSP60 255-275; IgM_HSP60 106-125; IgM_OSP 31-50; IgM_P2 61-80; IgM_MBP 11-30; IgM_HSP60 376-395; IgM_HSP70 286-305; IgM_HSP60 136-155; IgM_HSP70 136-155; IgM_P2 46-65; IgM_OSP 136-155; IgM_P2 1-20; IgM_MOG 91-110; IgM_HSP60 361-380; IgM_HSP70 451-470; IgM_HSP70 210-229; IgM_HSP60 240-259; IgM_HSP60 271-290; IgM_OSP 76-95; IgM_PLP 178-191; IgM_CNP 271-290; IgM_P2 76-95; IgM_HSP70 631-640; IgM_PLP 248-259; IgM_HSP60 195-214; IgM_CNP 61-80; IgM_MOG 196-215; IgM_HSP60 46-65; IgM_HSP70 195-214; IgM_HSP70 436-455; IgM_HSP60 166-185; IgM_MBP 104-123; IgM_MBP 71-92; IgM_PLP 180-199; IgM_HSP70 255-275; IgM_MOBP 166-185; IgM_CNP 240-259; IgM_HSP60 16-35; IgM_HSP60 301-320; IgM_MOBP 151-170; IgM_CNP 91-110; IgM_HSP70 106-125; IgM_CNP 406-421; IgM_HSP60 421-40; IgM_HSP60 61-80; IgM_Amyloid beta 10-20; IgM_HSP60 511-530; IgM_Lactocerebroside; IgM_HSP70 406-425; IgM_MOG 76-95; IgM_HSP70 316-335; IgM_HSP60 225-244; IgM_HSP60 76-95; IgM_MOG 106-125; IgM_HSP70 466-485; IgM_CNP 1-21; IgM_HSP70 166-185; IgM_HSP70 121-140; IgM_Amyloid beta 1-42; IgM_MBP 89-101; IgM_CNP 301-320; IgM_HSP70 1-20; IgM_MBP 51-70; IgM_HSP70 496-515; IgM_CNP 16-35; IgM_CNP 76-95; IgM_PLP 10-29; IgM_PLP 190-209; IgM_HSP60 346-365; IgM_HSP60 151-170; IgM_HSP70 376-395; IgM_bovineMBP; IgM_HSP70 556-575; IgM_CNP 391-410; IgM_MOG 211-230; IgM_PLP 220-249; IgM_HSP70 616-635; IgM_Amyloid beta 1-12; IgM_HSP60 556-573; and IgM_PLP 250-269.

This pattern consisted of 94 antibody reactivities. Of the 94 reactivities, 90 were up-regulated and 4 were down-regulated in MS versus controls (HC). Thus, RRMS is associated with both a gain and a loss of particular autoreactivities. Of the up-regulated reactivities, 50% were IgM antibodies binding to peptides of CNS antigens and 49% were IgM antibodies binding to peptides of heat shock proteins. The ability to distinguish MS vs. controls was not observed at dilutions of 1:100 or 1:1000.

To validate the discriminating pattern shown in FIG. 2A, a leave-one-out cross-validation analysis (LOOCV) was performed in the training set (Stekel, D., 2003, *Microarray Bioinformatics*, Cambridge University Press, Cambridge), which was then validated on the test set. For the LOOCV in the training set, the number of true (correct) and false (incorrect) classifications was computed to estimate the success rate, positive predictive value (PPV), negative predictive value (NPV) in the training set. The LOOCV revealed a positive predictive value (PPV)—defined as the fraction of RRMS patients identified as RRMS by their antigen microarray reactivity—of 0.75 and a negative predictive value (NPV)—defined as the fraction of HC identified as HC by their antigen microarray reactivity—of 0.90; the success rate was 0.83 (P<0.0001). The most rigorous validation is to test the patterns identified in the training set to determine whether they can differentiate MS subjects from HC in the test set. Significantly, the pattern identified in the training set was able to classify the test set of samples with a PPV of 0.85, a NPV of 0.80, and with a success rate of 0.83 (P=0.004, Fisher's exact test).

To further validate these findings, 51 untreated RRMS obtained from the University of Seville, Spain, were analyzed to determine if whether RRMS may be distinguished from HC using an independent cohort of samples from another institution and geographic area. The identified pattern was able to discriminate RRMS from HC in this independent cohort with a success rate of 0.69 with a PPV of 0.73 and a NPV of 0.58 (P=0.01, Fisher's exact test).

As a specificity control for the patterns detected in MS, sera from patients with systemic lupus erythematosus (SLE), adrenoleukodystrophy (ALD) and Alzheimer's disease (AD) was investigated. SLE is a chronic autoimmune disease characterized by circulating antibodies to a broad range of self-antigens. ALD is a degenerative disorder characterized by the accumulation of very long-chain fatty acids and a CNS neuroinflammatory process that shares features with MS. AD is not considered an autoimmune disease; however, immune responses to β-amyloid derived peptides have been reported. Significantly, the antibody patterns detected on antigen microarrays discriminated RRMS from SLE, ALD and AD samples (P<0.0001, Fisher's exact test).

Example 3

Autoantibody Pattern Analysis Identifies an Immune Signature for PPMS

PPMS has a different clinical course than RRMS, and it has been suggested that PPMS may involve disease mechanisms different from those in RRMS (Miller & Leary, 2007, *Lancet Neurol.* 6, 903-12). 24 PPMS and 25 age- and gender-matched HC in a training set, and 13 PPMS and 12 controls in a test set of samples were studied.

Figure 2B:
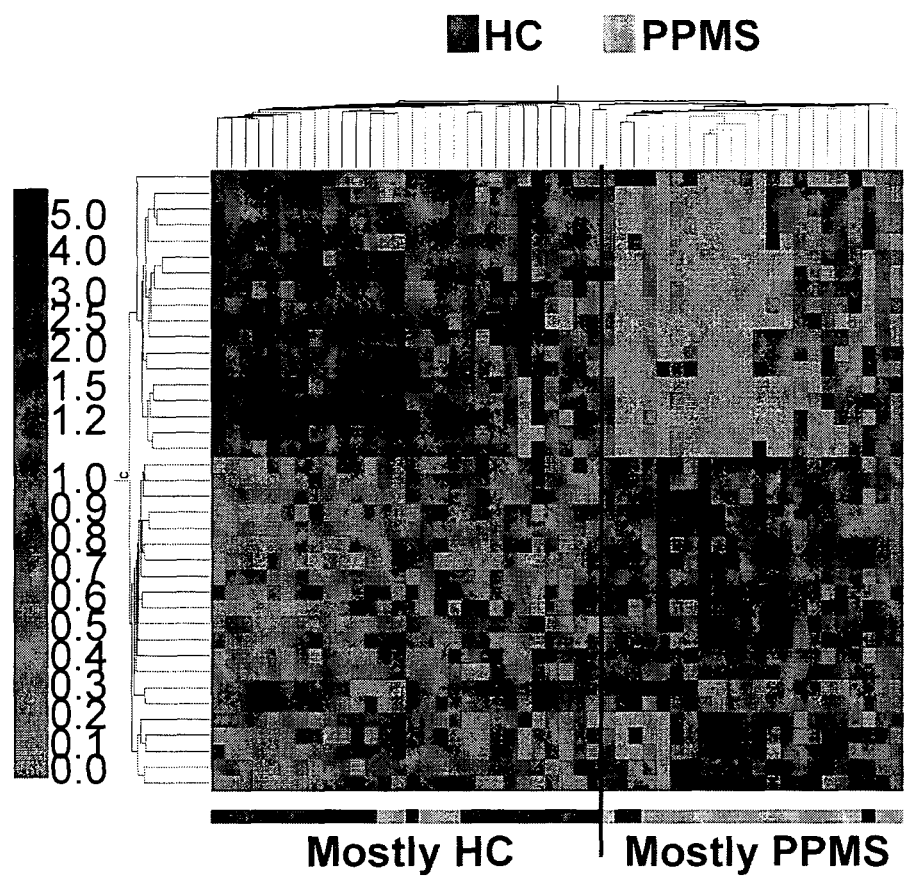

The antibody reactivities included in the heatmap shown in FIG. 2B are listed herein (in the same order as in the heatmap, i.e. from top to bottom): IgM_PLP 215-232; IgG_PLP 215-232; IgM_mMBP; IgG_HSP70 195-214; IgM_smLPS; IgM_HSP70 210-229; IgM_Chondroitin 4-Sulfate; IgG_HSP70 166-185; IgG_bovineMBP; IgM_bovineMBP; IgG_PLP 137-150; IgG_MOG 46-65; IgG_CNP 406-421; IgG_P2 31-50; IgG_CNP 1-20; IgG_MOG 16-35; IgG_P2 76-95; IgM_Neurofilament 68 kDa; IgM_Beta Amyloid; IgG_HSP70 466-485; IgM_AB 1-40; IgM_PLP 161-180; IgM_PLP 40-59; IgM_PLP 137-150; IgG_HSP60 76-95; IgG_MOG 151-170; IgG_P2 1-20; IgG_OSP 61-80; IgM_Secreted APPalpha; IgG_PLP 178-191; IgM_gpMBP; IgG_HSP70 16-35; IgM_MBP 104-123; IgM_SOD; IgM_CNP 1-20; IgM_ecLPS; IgG_HSP70 121-140; IgM_MOBP 61-80; and IgG_OSP 1-20.

The heatmap (FIG. 2B) shows the antibody reactivities that passed significance tests and could discriminate PPMS and HC both in the training set (P<0.0001, Fisher's exact test) and the test set (P<0.01, Fisher's exact test). The LOOCV on the learning set revealed an overall efficiency of 86%, with PPV=0.87 and NPV=0.85. The efficiency for the test set was 72%; the PPV=0.79 and the NPV=0.75. As with RRMS, antigen microarrays were able to discriminate PPMS from control subjects at a 1:10 dilution but not at dilutions of 1:100 or 1:1000. Furthermore, as with RRMS, the antigen microarray analysis discriminated between PPMS and other diseases (SLE, ALD, AD; P<0.001, Fisher's exact test).

Figure 2C:
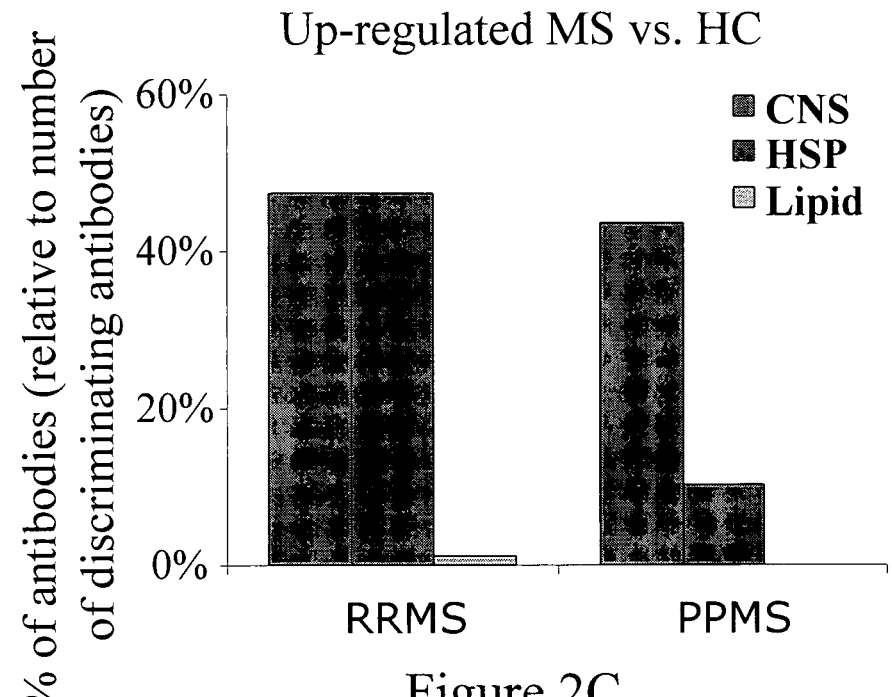
FIGS. 2C-2D show the antigen specificity in RRMS and PPMS. The specificity of the discriminating antibodies in RRMS and PPMS is shown as the relative contribution of CNS, HSP and lipid antigens (% relative to total number of discriminating antigens) found to be up- or down-regulated (FIGS. 2C and 2D respectively) in MS relative to HC.
Figure 2D:
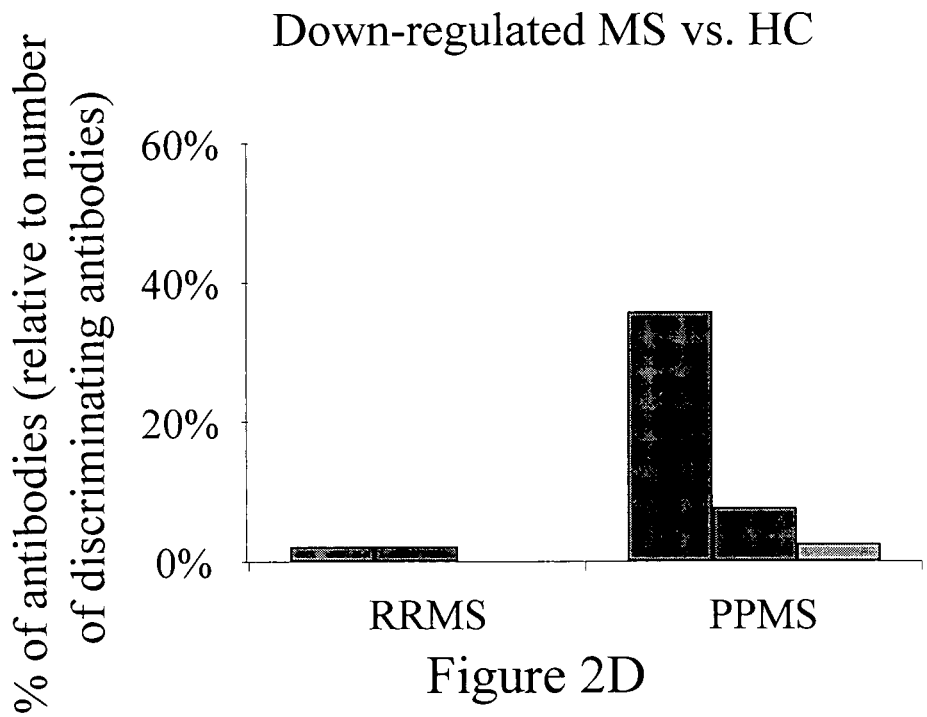

The discriminating reactivities in PPMS were IgG (51%) and IgM (49%) and were mainly directed against CNS antigens (FIGS. 2B-2D). The CNS antigens in the PPMS immune signature were different from those in the RRMS signature. The RRMS CNS signature was termed CNS[1] and the PPMS CNS signature was termed CNS[2] (FIG. 2H and Table 8). Further comparison of RRMS and PPMS revealed a pronounced reactivity against HSP60 or HSP70 in RRMS that was not observed in PPMS (FIGS. 2A-2D). Furthermore, 46% of the discriminating reactivities in PPMS consisted of antibodies that were decreased in PPMS compared to HC, whereas in RRMS only 4% of the discriminating antibodies were decreased compared to HC (FIGS. 2B-2D and Tables 8 and 9). There was only a minor overlap between the reactivities that discriminated PPMS and those that discriminated RRMS compared to HC. This finding is compatible with the view that different immune processes occur in these two forms of MS (Miller & Leary, 2007).

Example 4

Autoantibody Pattern Analysis Identifies an Immune Signature for SPMS

Approximately 50% of the RRMS patients become progressive (SPMS). Although there is no consensus on the mechanisms involved in the transition to SPMS, several studies suggest changes in the nature of the inflammatory response and the emergence of neurodegenerative processes occur in the secondary progressive phase of MS. Having identified an autoantibody signature in RRMS which consisted of increased reactivity to HSP and a unique pattern of reactivity to CNS antigens (CNS[1]), the antibody signature associated with SPMS was studied by comparing antibody reactivity in 37 RRMS vs. 30 SPMS samples (FIG. 2E).

Figure 2E:
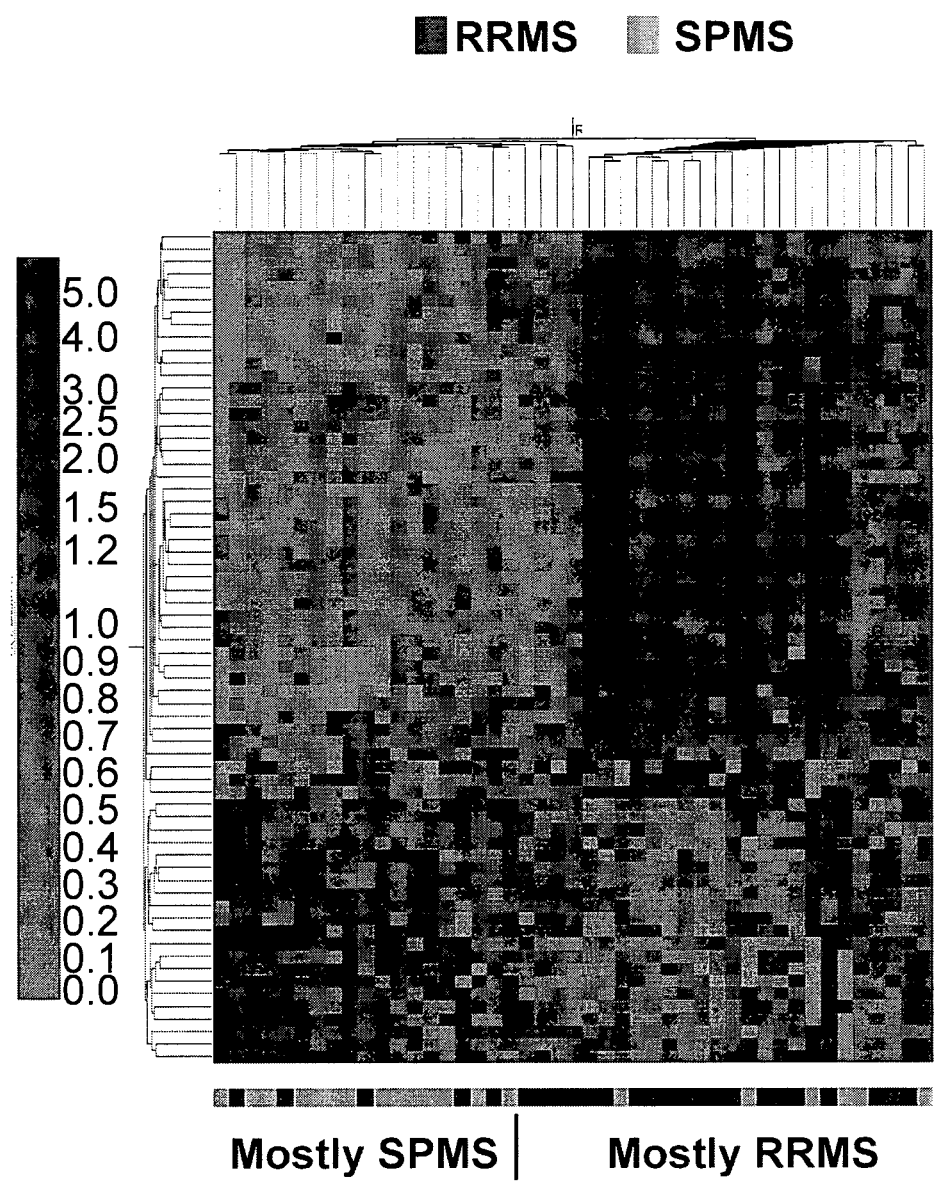
FIG. 2E shows heatmap depicting the antibody reactivities in SPMS and RRMS samples.
Figure 2F:
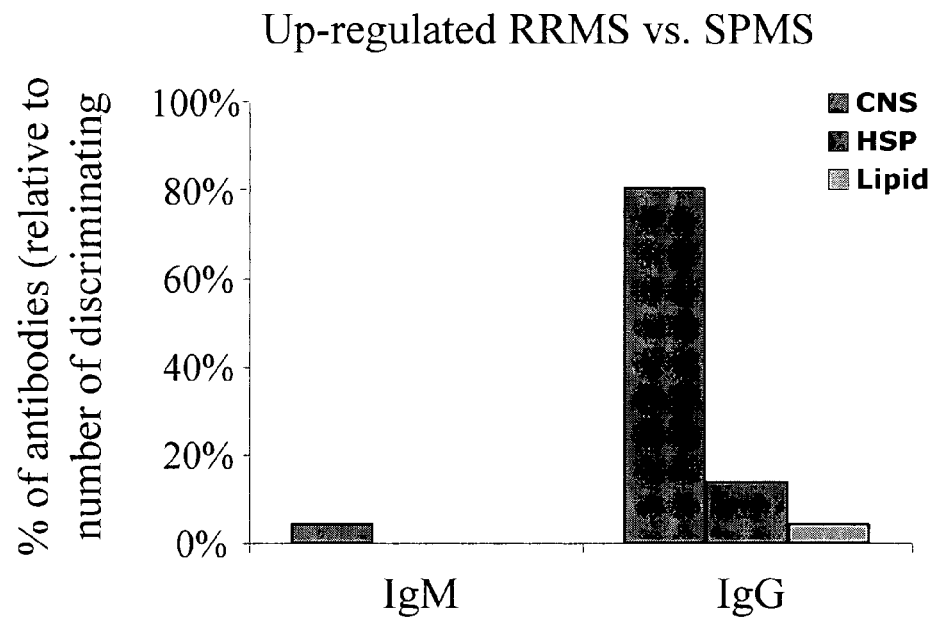
FIGS. 2F and 2G show the antigen specificity in SPMS, shown as the relative contribution of CNS, HSP and lipid antigens (% relative to total number of discriminating antigens) found to be up- or down-regulated (FIGS. 2F and 2G respectively) in SPMS relative to RRMS.
Figure 2G:
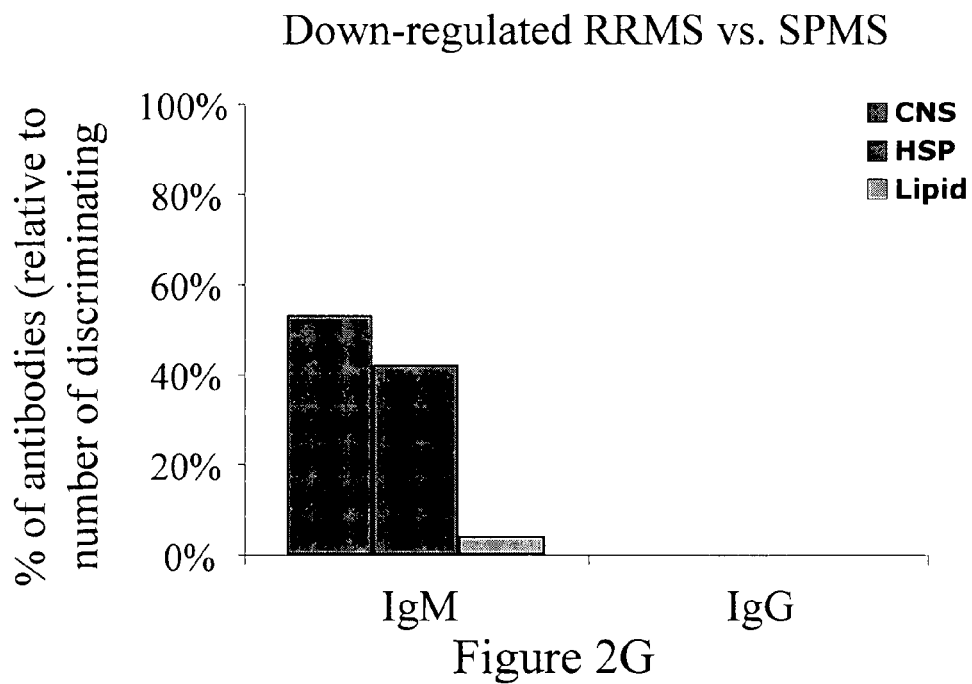
Figure 2H:
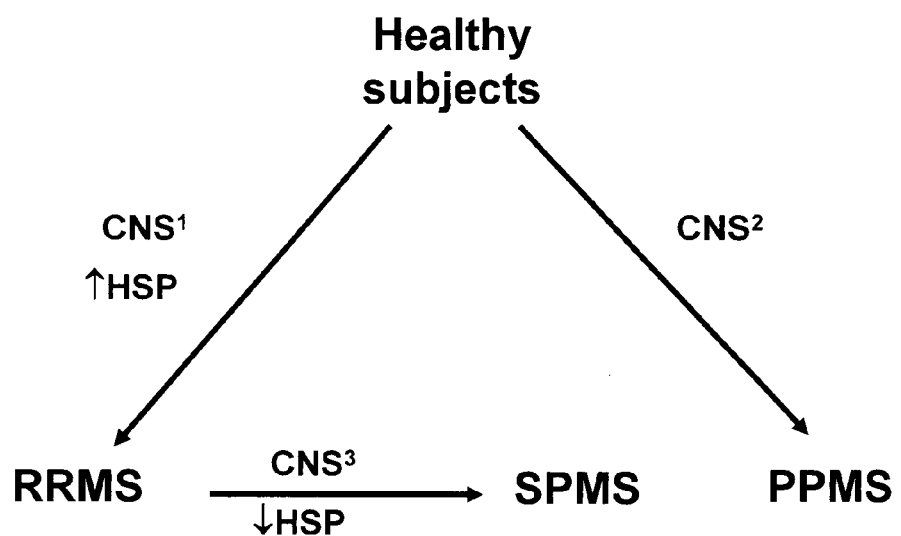
FIG. 2H is a diagram summarizing the immune signature associated with RRMS, SPMS and PPMS.

The antibody reactivities included in the heatmap shown in FIG. 2E are listed herein (in the same order as in the heatmap, i.e. from top to bottom): IgM_MOG 61-80; IgM_HSP60 376-395; IgM_MOG 31-50; IgM_CNP 361-380; IgM_Amyloid beta 1-23; IgM_CNP 346-365; IgM_HSP60 496-515; IgM_OSP 1-20; IgM_HSP60 511-530; IgM_OSP 61-80; IgM_HSP60 286-305; IgM_CNP 240-259; IgM_HSP70 601-620; IgM_HSP60 210-229; IgM_HSP60 451-470; IgM_MOBP 166-185; IgM_HSP60 166-185; IgM_MBP 138-147; IgM_CNP 195-214; IgM_MBP 1-20; IgM_HSP60 526-545; IgM_P2 1-20; IgM_HSP70 286-305; IgM_MBP 155-178; IgM_P2 46-65; IgM_HSP60 195-214; IgM_P2 31-50; IgM_HSP60 271-290; IgM_HSP60 136-155; IgM_CNP 286-305; IgM_HSP70 210-229; IgM_HSP70 136-155; IgM_PLP 150-163; IgM_HSP70 166-185; IgM_HSP60 255-275; IgM_HSP60 16-35; IgM_bovineMBP; IgM_CNP 181-199; IgM_CNP 121-140; IgM_Asialoganglioside-GM2; IgM_Amyloid beta 1-12; IgM_OSP 121-140; IgM_Secreted APPbeta; IgM_Cardiolipin; IgM_HSP70 406-425; IgG_HSP60 361-380; IgG_Amyloid beta 17-40; IgG_Cholesterol; IgG_Amyloid beta 1-42; IgG_PLP 80-99; IgG_PLP 65-84; IgG_PLP 40-59; IgG_PLP 1-19; IgM_PLP 1-19; IgG_PLP 151-173; IgG_HSP70 421-440; IgG_huMBP; IgG_MOBP 16-35; IgG_CNP 16-35; IgG_RBP; IgG_HSP70 331-350; IgG_OSP 121-140; IgG_MBP 113-132; IgG_beta Crystallin; IgG_CNP 240-259; and IgG_PLP 178-191.

The results show that SPMS could be discriminated from RRMS with a success rate of 71% (P=0.0073). SPMS was characterized by a decrease in the IgM antibodies to HSP60 and HSP70 that were found in RRMS (FIG. 2E and Tables 8 and 9). Thus, SPMS and PPMS are similar in that both have only minimal reactivity to HSP. Examination of the CNS reactivity in SPMS revealed a decrease in CNS IgM antibodies that were upregulated in RRMS, and an increase in CNS-reactive IgG antibodies. The CNS signature for SPMS differed from both RRMS and PPMS and was termed CNS[3] (FIGS. 2E-2H, Table 8).

TABLE 8

Reactivity to CNS antigens in RRMS, PPMS and SPMS

IgM

| Antigen | RRMS (CNS1) | PPMS (CNS2) | SPMS (CNS3) |
|---|---|---|---|
| IgM_Beta Amyloid | | ● | |
| IgM_Beta Amyloid 1-12 | ● | | ● |
| IgM_Beta Amyloid 1-23 | | | ● |
| IgM_Beta Amyloid 10-20 | ● | | |
| IgM_Beta Amyloid 12-28 | | | |
| IgG_Beta Amyloid 17-40 | | | ● |
| IgM_Beta Amyloid 1-42 | ● | | ● |
| IgM_Beta Amyloid 1-40 | | ● | |
| IgG_beta Crystallin | | | ● |
| IgM_bovineMBP | ● | ● | |
| IgM_CNP 1-20 | ● | ● | |
| IgM_CNP 16-35 | ● | | ● |
| IgM_CNP 61-80 | ● | | |
| IgM_CNP 76-95 | ● | | |
| IgM_CNP 91-110 | ● | | |
| IgM_CNP 121-140 | | | ● |
| IgM_CNP 181-199 | | | ● |
| IgM_CNP 195-214 | | | ● |
| IgM_CNP 240-259 | ● | | ● |
| IgM_CNP 271-290 | ● | | |
| IgM_CNP 286-305 | ● | | ● |
| IgM_CNP 301-320 | ● | | |
| IgM_CNP 346-365 | | | ● |
| IgM_CNP 361-380 | | | ● |
| IgM_CNP 376-395 | | | |
| IgM_CNP 391-410 | ● | | |
| IgM_CNP 406-421 | | | |
| IgM_Neurofilament 68kDa | | | ● |
| IgM_gpMBP | ● | | |
| IgM_bovineMBP | | | ● |
| IgM_mMBP | | | ● |
| IgM_MBP 1-20 | | | ● |
| IgM_MBP 11-30 | ● | | |
| IgM_MBP 41-60 | ● | | |
| IgM_MBP 51-70 | ● | | |
| IgM_MBP 71-92 | ● | | |
| IgM_MBP 84-94 | ● | | |
| IgM_MBP 89-101 | ● | | |
| IgM_MBP 104-123 | ● | ● | |
| IgM_MBP 138-147 | | | ● |
| IgM_MBP 155-178 | | | ● |
| IgM_MOBP 61-80 | | ● | |
| IgM_MOBP 151-170 | ● | | |
| IgM_MOBP 166-185 | ● | | ● |
| IgM_MOG 31-50 | | | ● |
| IgM_MOG 61-80 | | | ● |
| IgM_MOG 106-125 | ● | | |
| IgM_MOG 196-215 | ● | | |
| IgM_MOG 211-230 | ● | | |

TABLE 8-continued

IgG

| Antigen | RRMS (CNS1) | PPMS (CNS2) | SPMS (CNS3) |
|---|---|---|---|
| IgG_CNP 1-20 | | ● | |
| IgG_CNP 406-421 | | ● | |
| IgG_GFAP | ● | | |
| IgG_bovineMBP | | ● | |
| IgG_huMBP | | | ● |
| IgG_MBP 31-50 | ● | | |
| IgG_MBP 113-132 | | | ● |
| IgG_PLP 65-84 | ● | | |
| IgG_MOBP 16-35 | | | ● |
| IgG_MOG 16-35 | | ● | |
| IgG_MOG 46-65 | | ● | |
| IgG_MOG 151-170 | | | ● |
| IgG_OSP 1-20 | | | ● |
| IgG_OSP 61-80 | | | ● |
| IgG_OSP 121-140 | | | ● |
| IgG_P2 1-20 | | | ● |
| IgG_P2 31-50 | | ● | |
| IgG_P2 76-95 | | | ● |
| IgG_PLP 1-19 | | | ● |
| IgG_PLP 40-59 | | | ● |
| IgG_PLP 65-84 | | | ● |
| IgG_PLP 137-150 | | ● | |
| IgG_PLP 151-173 | | | ● |
| IgG_PLP 178-191 | | ● | ● |
| IgG_PLP 215-232 | | ● | |

TABLE 9

Reactivity to HSP in RRMS, SPMS and PPMS

| Antigen | RRMS | PPMS | RRMS vs. SPMS |
|---|---|---|---|
| IgM_HSP60 16-35 | ● | | ● |
| IgM_HSP60 46-65 | ● | | |
| IgM_HSP60 106-125 | ● | | |
| IgM_HSP60 136-155 | ● | | ● |
| IgM_HSP60 151-170 | ● | | |
| IgM_HSP60 166-185 | ● | | ● |
| IgM_HSP60 195-214 | ● | | ● |
| IgM_HSP60 210-229 | | | ● |
| IgM_HSP60 225-244 | ● | | |
| IgM_HSP60 240-259 | ● | | |
| IgM_HSP60 255-275 | ● | | ● |
| IgM_HSP60 271-290 | ● | | |
| IgM_HSP60 286-305 | ● | | ● |
| IgM_HSP60 301-320 | ● | | |
| IgM_HSP60 346-365 | ● | | |
| IgM_HSP60 361-380 | ● | | |
| IgM_HSP60 376-395 | ● | | ● |

TABLE 9-continued

| | | |
|---|---|---|
| IgM_HSP60 421-440 | s | |
| IgM_HSP60 451-470 | | t |
| IgM_HSP60 496-515 | s | t |
| IgM_HSP60 511-530 | s | t |
| IgM_HSP60 526-545 | s | t |
| IgM_HSP60 556-573 | s | |
| IgM_HSP60 60-80 | s | |
| IgM_HSP60 76-95 | s | s |
| IgM_HSP70 1-20 | s | |
| IgM_HSP70 31-50 | s | |
| IgM_HSP70 106-125 | s | |
| IgM_HSP70 121-140 | s | s |
| IgM_HSP70 136-155 | s | t |
| IgM_HSP70 151-170 | s | |
| IgM_HSP70 166-185 | s | t | t |
| IgM_HSP70 195-214 | s | t | |
| IgM_HSP70 210-229 | s | t | t |
| IgM_HSP70 255-275 | s | | |
| IgM_HSP70 286-305 | s | | t |
| IgM_HSP70 316-335 | s | | |
| IgM_HSP70 376-395 | s | | |
| IgM_HSP70 406-425 | s | | t |
| IgM_HSP70 436-455 | s | | |
| IgM_HSP70 451-470 | s | | |
| IgM_HSP70 466-485 | s | s | |
| IgM_HSP70 496-515 | s | | |
| IgM_HSP70 511-530 | s | | |
| IgM_HSP70 556-575 | s | | |

The detection of significant changes in the antibody reactivity to CNP and HSP, in Tables 8 and 9, respectively, is shown as a black square, wherein 's' indicates up regulated and 't' indicates down regulation relative to HC (for RRMS and PPMS) or RRMS (for SPMS).

Example 5

Autoantibody Patterns Distinguish Pathologic Subtypes of MS

Lucchinetti, Bruck and Lassman have defined four immunopathologic patterns of MS (Lucchinetti et al., 200; Lucchinetti et al., 2004). Investigation was performed on serum taken at the time of brain biopsy from 15 Pattern 1 and 30 Pattern II subjects.

Figure 3:
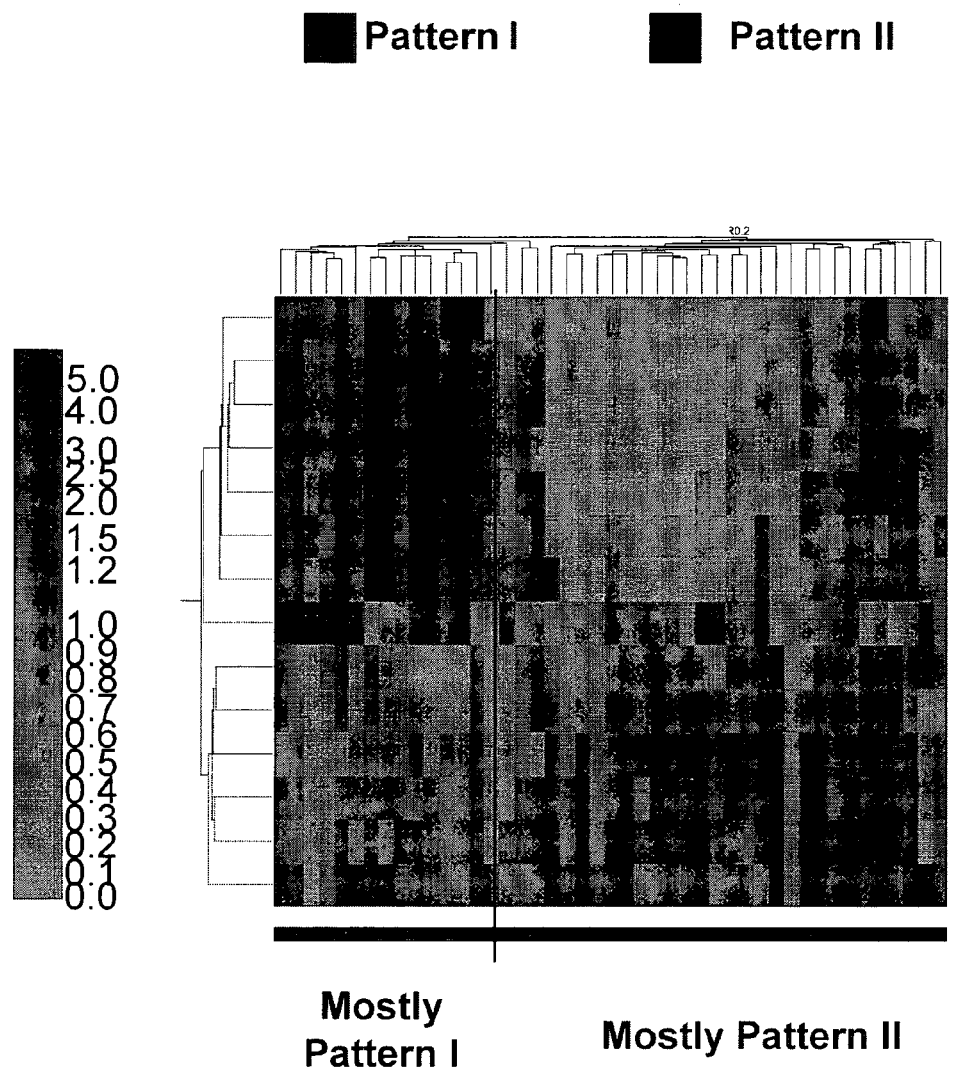
FIG. 3 shows the antibody reactivity associated with brain pathology. Heatmap in which each column represents a patient, color-coded at the bottom to indicate whether it corresponds to a Pattern I or Pattern II sample, shows the normalized antibody reactivity to an antigen according to the colorimetric scale shown on the left. The antibody reactivities used to construct this heatmap are listed in Example 5 below.

The antibody reactivities included in the heatmap shown in FIG. 3 are listed herein (in the same order as in the heatmap, i.e. from top to bottom): IgG__15-ketocholestane; IgG__15α-hydroxycholestene; IgG_Ganglioside-GM4; IgG__15-ketocholestene; IgG Tetrasialoganglioside-GQ1B; IgG_Brain L-α-lysophosphatidylserine; IgG_Lactosylceramide; IgM__160 kDa. Neurofilament; IgG_HSP60 240-259; IgG_OSP 166-185; IgG_MOG 196-215; IgG_OSP 61-80; IgG_OSP 1-20; and IgG_PLP 215-232. As shown in FIG. 3, the autoantibody patterns was able to discriminate pattern I from patterns II (P=0.0082, Fisher's exact test). To validate this finding, analysis was performed on a blinded set of samples that contained the 15 pattern I used for analysis above mixed randomly with 23 new pattern II samples. In this validation test, pattern I was distinguished from pattern II (P=0.0017, Fisher's exact test). The LOOCV on the learning set revealed a success rate of 0.78, with PPV=0.78 and NPV=0.67, the success rate for the test set was 0.78; the PPV=0.82 and the NPV=0.73.

The immune signature that distinguished pattern I from pattern II consisted of 13 IgG and 1 IgM reactivities against lipids, HSP and CNS antigens (FIG. 3). Pattern II subjects showed increased IgG reactivity to HSP60, MOG, OSP and PLP peptide epitopes. Noteworthy, the up-regulated reactivities in pattern I subjects were IgG antibodies to 7 lipids; 3 of these lipids were oxidized derivatives of cholesterol (15-ketocholestene, 15-ketocholestane and 15α-hydroxycholestene).

Example 6

Cholesterol Derivatives Worsen Experimental Autoimmune Encephalomyelitis (EAE)

It has been postulated that the oxidized derivative of cholesterol, 7-ketocholesterol, contributes to MS pathology by activating microglial cells via a poly (ADP-ribose)-polymerase-1 enzyme (PARP) dependent pathway. To explore the relationship between autoantibodies to oxidized cholesterol derivatives (oxChol) and disease pathology, the effect of the lipids found in Example 5 was examined on EAE, an immune model of MS.

EAE was induced in C57BL/6 mice with MOG35-55, and 15-ketocholestene, 15-ketocholestane and 15α-hydroxycholestene were administered at days 0, 4, 7 and 10 after EAE induction (10 μg/mice). AIQ was administered intraperitoneally (60 μg/mice) on daily basis. The course of EAE in these mice is shown as the mean EAE score+s.e.m. ($MOG_{35-55}$ n=22, $MOG_{35-55}$+oxChol n=24, $MOG_{35-55}$+oxChol+AIQ n=18).

Figure 4A:
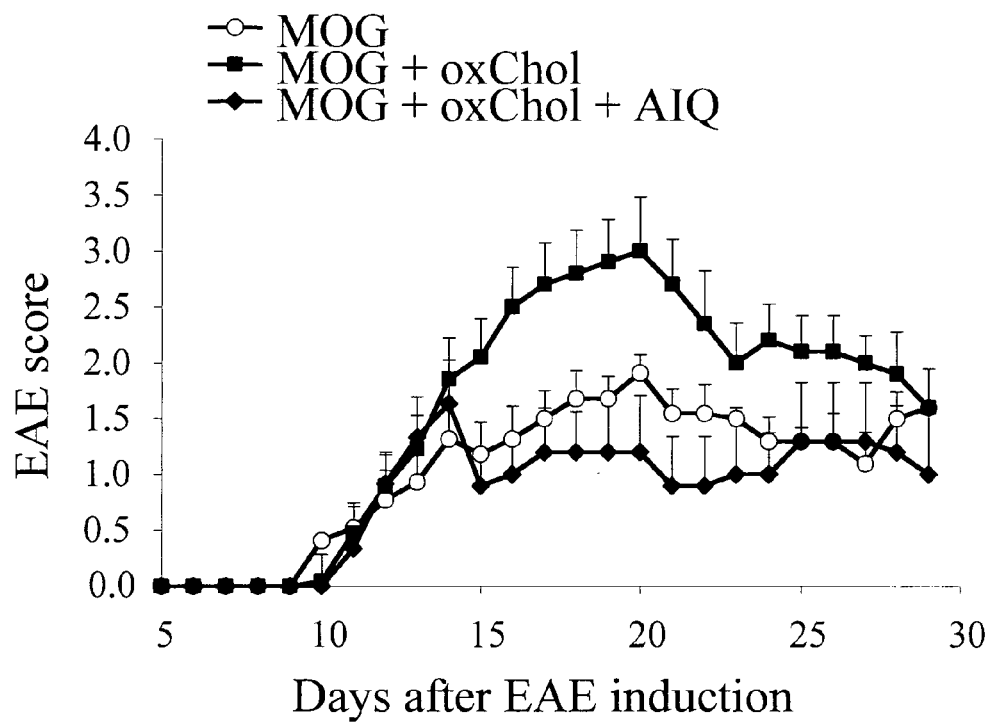
FIG. 4A shows that the administration of oxidized cholesterol derivatives to EAE worsens EAE.
Figure 4B:
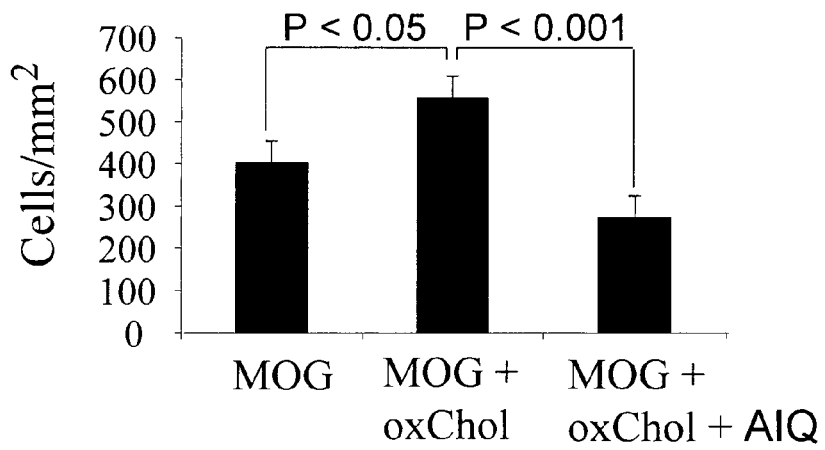
FIGS. 4B-BD depict quantification of the cellular infiltrate (FIG. 4B), demyelination (FIG. 4C) and axonal loss on the spinal cord (FIG. 4D) of $MOG_{35-55}$, $MOG_{35-55}$+oxChol or $MOG_{35-55}$+oxChol+AIQ mice.
Figure 4C:
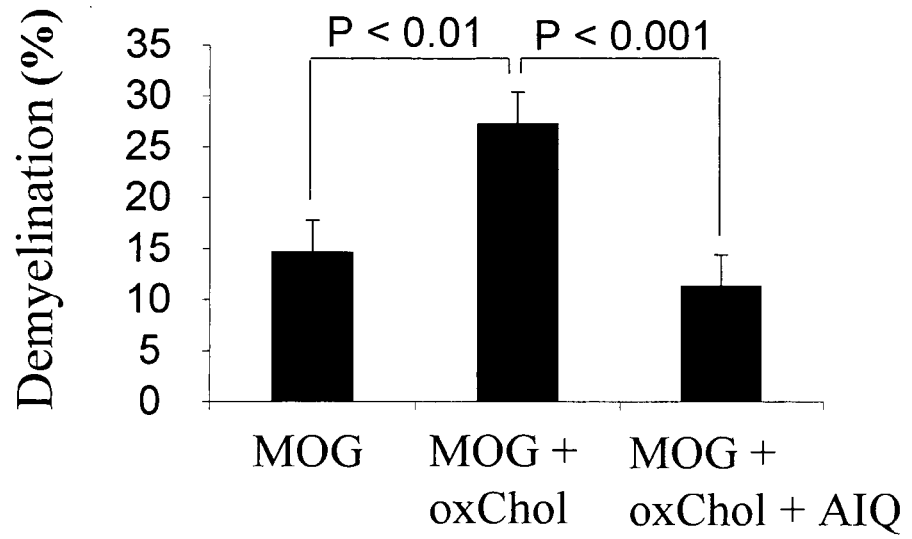
FIG. 4 shows the effect of administration of oxidized cholesterol derivatives to EAE.
Figure 4D:
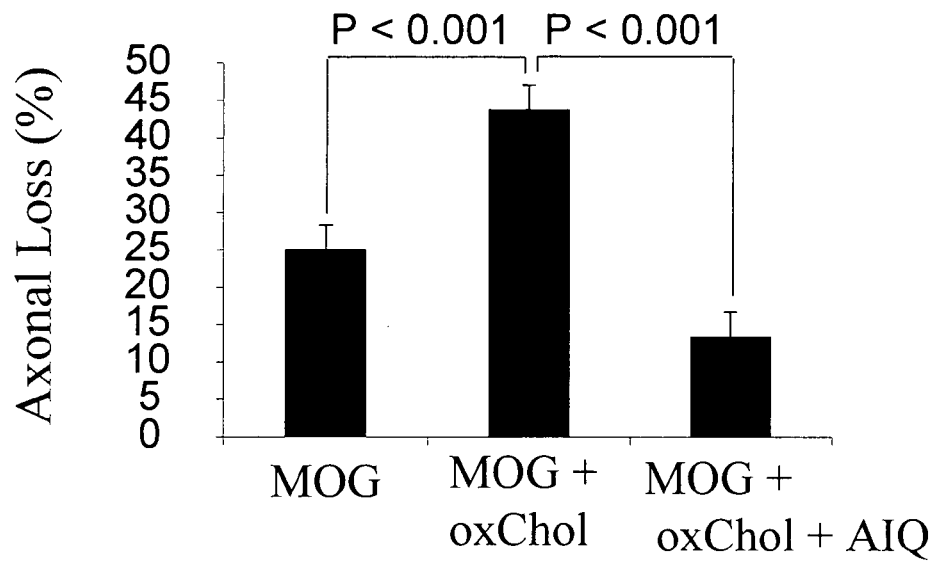

Spinal cords were taken on day 19 and stained with hematoxylin and eosin, luxol fast blue or silver stain to quantify the cellular infiltrate, demyelination and axonal loss, respectively. Each column represents the mean±SEM resulting from the analysis of at least 8 sections. Administration of oxChol enhanced EAE as measured clinically (FIG. 4A, P<0.0001, two-way ANOVA), and augmented inflammatory infiltrates (FIG. 4B; P<0.05, one-way ANOVA), demyelination (FIG. 4C; P<0.01, one-way ANOVA) and axonal loss (FIG. 4D; P<0.001, one-way ANOVA); these effects were inhibited by treatment with AIQ (P<0.001, one-way ANOVA).

Further investigations were performed to determine whether the effect of oxChol on EAE was mediated by PARP. Using a PARP inhibitor, 5-Aminoisoquinolinone (AIQ) it was found that AIQ abrogated the worsening of EAE caused by oxChol both clinically (P<0.0001, two-way ANOVA) and histopathologically (P<0.001, one-way ANOVA) (FIGS. 4A-D) but did not affect T cell responses to $MOG_{35-55}$ as measured by cytokines (IFN-γ and IL-17) or proliferation. In addition, transfer of serum from oxChol-treated mice did not enhance EAE. Taken together, these results suggest that the effect of oxChol on EAE is due to the effect of oxChol through PARP and not through the induction of anti-lipid antibodies or affecting adaptive T cell responses to $MOG_{35-55}$.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of diagnosing a subtype of multiple sclerosis (MS) in a subject, the method comprising determining the reactivity of antibodies in a sample obtained from the subject to a plurality of antigens selected from the group consisting of the antigens listed in Tables 1 to 4, thereby determining the reactivity pattern of the sample to the plurality of antigens, and comparing the reactivity pattern of said sample to a control reactivity pattern, wherein the subtype of MS is selected from the group consisting of:
   (i) relapsing remitting multiple sclerosis (RRMS) wherein said plurality of antigens comprises at least 5 different antigens selected from the group consisting of the antigens listed in Table 1;
   (ii) primary progressive multiple sclerosis (PPMS) wherein said plurality of antigens comprises at least 5 different antigens selected from the group consisting of the antigens listed in Table 2;
   (iii) secondary progressive multiple sclerosis (SPMS) wherein said plurality of antigens comprises at least 5 different antigens selected from the group consisting of the antigens listed in Table 3; and
   (iv) a pathologic subtype of MS selected form Pattern I lesions and Pattern II lesions wherein said plurality of antigens comprises at least 5 different antigens selected from the group consisting of the antigens listed in Table 4;
wherein said plurality of antigens is used in the form of an antigen array comprising a glass support, wherein determining the reactivity of antibodies in the sample to the plurality of antigens is performed using a system providing quantitative measurement of antigen-antibody binding by fluorescence detection, and wherein a significant difference between the reactivity pattern of said sample obtained from the subject compared to a reactivity pattern of a control sample is an indication that the subject is afflicted with the subtype of MS.

2. The method of claim 1, wherein the glass support is an epoxy glass support.

3. The method of claim 2, wherein each antigen is attached to at least three separate specific addressable locations of the array.

4. The method of claim 1 for diagnosing relapsing remitting multiple sclerosis (RRMS) in a subject, wherein the plurality of antigens are selected from the antigens listed in Table 1 and the control reactivity pattern is obtained from healthy subjects.

5. The method of claim 1, wherein each antigen is attached to at least three separate specific addressable locations of the array.

6. The method of claim 4, wherein the plurality of antigens comprises all the antigens listed in Table 1.

7. The method of claim 1, for diagnosing primary progressive multiple sclerosis (PPMS) in a subject, wherein the plurality of antigens are selected from the antigens listed in Table 2 and the control reactivity pattern is obtained from healthy subjects.

8. The method of claim 7, wherein the plurality of antigens comprises all the antigens listed in Table 2.

9. The method of claim 1 for diagnosing secondary progressive multiple sclerosis (SPMS) in a subject, wherein the plurality of antigens are selected from the antigens listed in Table 3 and the control reactivity pattern is obtained from RRMS subjects.

10. The method of claim 9, wherein the plurality of antigens comprises all the antigens listed in Table 3.

11. The method of claim 1 for diagnosing Pattern I lesions in a subject with MS, wherein the plurality of antigens is selected from the antigens listed in Table 4 and the control reactivity pattern is obtained from subjects having Pattern II lesions.

12. The method of claim 1 for diagnosing Pattern II lesions in a subject with MS, wherein the plurality of antigens is selected from the antigens listed in Table 4 and the control reactivity pattern is obtained from subjects having Pattern I lesions.

13. The method of claim 1, wherein the control is selected from the group consisting of a sample from at least one individual, a panel of control samples from a set of individuals, and a stored set of data from control individuals.

14. The method of claim 1, wherein the sample is a serum sample.

15. The method of claim 1, further comprising diluting the sample 1:10 before determining the reactivity of antibodies in the sample.

16. The method of claim 1, wherein the subtype of MS is selected from the group consisting of:
   (i) relapsing remitting multiple sclerosis (RRMS) wherein said plurality of antigens is HSP70 511-530, HSP60 286-305, LACTOCEREBROSIDE, AB1-42 and AB1-12, listed in Table 1;
   (ii) primary progressive multiple sclerosis (PPMS) wherein said plurality of antigens is Chondroitin 4-Sulfate, Neurofilament 68 kDa, Amyloid Beta, Secreted APPalpha and SOD, listed in Table 2;
   (iii) secondary progressive multiple sclerosis (SPMS) wherein said plurality of antigens is HSP60 376-395, Amyloid beta 1-23, HSP70 601-620, Cardiolipin and beta Crystallin, listed in Table 3; and
   (iv) a pathologic subtype of MS selected from Pattern I lesions and Pattern II lesions wherein said plurality of antigens is 15-ketocholestane, 15α-hydroxycholestene, 15-ketocholestene, Brain L-α-lysophosphatidylserine and 160 kDa. Neurofilament, listed in Table 4.

* * * * *

```
                          SEQUENCE LISTING

<160> NUMBER OF SEQ ID NOS: 103

<210> SEQ ID NO 1
<211> LENGTH: 573
<212> TYPE: PRT
<213> ORGANISM: Homo sapiens

<400> SEQUENCE: 1

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
```

```
            340                 345                 350
Asp Asp Ala Met Leu Lys Gly Lys Gly Asp Lys Ala Gln Ile Glu
        355                 360                 365
Lys Arg Ile Gln Glu Ile Ile Glu Gln Leu Asp Val Thr Thr Ser Glu
370                     375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
            420                 425                 430
Glu Glu Gly Ile Val Leu Gly Gly Gly Cys Ala Leu Leu Arg Cys Ile
        435                 440                 445
Pro Ala Leu Asp Ser Leu Thr Pro Ala Asn Glu Asp Gln Lys Ile Gly
    450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
Met Val Glu Lys Gly Ile Ile Asp Pro Thr Lys Val Val Arg Thr Ala
        515                 520                 525
Leu Leu Asp Ala Ala Gly Val Ala Ser Leu Leu Thr Thr Ala Glu Val
    530                 535                 540
Val Val Thr Glu Ile Pro Lys Glu Glu Lys Asp Pro Gly Met Gly Ala
545                 550                 555                 560
Met Gly Gly Met Gly Gly Gly Met Gly Gly Gly Met Phe
                565                 570

<210> SEQ ID NO 2
<211> LENGTH: 840
<212> TYPE: PRT
<213> ORGANISM: Homo sapiens

<400> SEQUENCE: 2

Met Ser Val Val Gly Ile Asp Leu Gly Phe Gln Ser Cys Tyr Val Ala
1               5                   10                  15
Val Ala Arg Ala Gly Gly Ile Glu Thr Ile Ala Asn Glu Tyr Ser Asp
            20                  25                  30
Arg Cys Thr Pro Ala Cys Ile Ser Phe Gly Pro Lys Asn Arg Ser Ile
        35                  40                  45
Gly Ala Ala Ala Lys Ser Gln Val Ile Ser Asn Ala Lys Asn Thr Val
    50                  55                  60
Gln Gly Phe Lys Arg Phe His Gly Arg Ala Phe Ser Asp Pro Phe Val
65                  70                  75                  80
Glu Ala Glu Lys Ser Asn Leu Ala Tyr Asp Ile Val Gln Leu Pro Thr
                85                  90                  95
Gly Leu Thr Gly Ile Lys Val Thr Tyr Met Glu Glu Glu Arg Asn Phe
            100                 105                 110
Thr Thr Glu Gln Val Thr Ala Met Leu Leu Ser Lys Leu Lys Glu Thr
        115                 120                 125
Ala Glu Ser Val Leu Lys Lys Pro Val Val Asp Cys Val Val Ser Val
    130                 135                 140
```

```
Pro Cys Phe Tyr Thr Asp Ala Glu Arg Arg Ser Val Met Asp Ala Thr
145                 150                 155                 160

Gln Ile Ala Gly Leu Asn Cys Leu Arg Leu Met Asn Glu Thr Thr Ala
            165                 170                 175

Val Ala Leu Ala Tyr Gly Ile Tyr Lys Gln Asp Leu Pro Ala Leu Glu
        180                 185                 190

Glu Lys Pro Arg Asn Val Val Phe Val Asp Met Gly His Ser Ala Tyr
    195                 200                 205

Gln Val Ser Val Cys Ala Phe Asn Arg Gly Lys Leu Lys Val Leu Ala
        210                 215                 220

Thr Ala Phe Asp Thr Thr Leu Gly Gly Arg Lys Phe Asp Glu Val Leu
225                 230                 235                 240

Val Asn His Phe Cys Glu Glu Phe Gly Lys Lys Tyr Lys Leu Asp Ile
                245                 250                 255

Lys Ser Lys Ile Arg Ala Leu Leu Arg Leu Ser Gln Glu Cys Glu Lys
            260                 265                 270

Leu Lys Lys Leu Met Ser Ala Asn Ala Ser Asp Leu Pro Leu Ser Ile
        275                 280                 285

Glu Cys Phe Met Asn Asp Val Asp Val Ser Gly Thr Met Asn Arg Gly
290                 295                 300

Lys Phe Leu Glu Met Cys Asn Asp Leu Leu Ala Arg Val Glu Pro Pro
305                 310                 315                 320

Leu Arg Ser Val Leu Glu Gln Thr Lys Leu Lys Lys Glu Asp Ile Tyr
                325                 330                 335

Ala Val Glu Ile Val Gly Gly Ala Thr Arg Ile Pro Ala Val Lys Glu
            340                 345                 350

Lys Ile Ser Lys Phe Phe Gly Lys Glu Leu Ser Thr Thr Leu Asn Ala
        355                 360                 365

Asp Glu Ala Val Thr Arg Gly Cys Ala Leu Gln Cys Ala Ile Leu Ser
370                 375                 380

Pro Ala Phe Lys Val Arg Glu Phe Ser Ile Thr Asp Val Val Pro Tyr
385                 390                 395                 400

Pro Ile Ser Leu Arg Trp Asn Ser Pro Ala Glu Glu Gly Ser Ser Asp
                405                 410                 415

Cys Glu Val Phe Ser Lys Asn His Ala Ala Pro Phe Ser Lys Val Leu
            420                 425                 430

Thr Phe Tyr Arg Lys Glu Pro Phe Thr Leu Glu Ala Tyr Tyr Ser Ser
        435                 440                 445

Pro Gln Asp Leu Pro Tyr Pro Asp Pro Ala Ile Ala Gln Phe Ser Val
450                 455                 460

Gln Lys Val Thr Pro Gln Ser Asp Gly Ser Ser Ser Lys Val Lys Val
465                 470                 475                 480

Lys Val Arg Val Asn Val His Gly Ile Phe Ser Val Ser Ser Ala Ser
                485                 490                 495

Leu Val Glu Val His Lys Ser Glu Glu Asn Glu Pro Met Glu Thr
        500                 505                 510

Asp Gln Asn Ala Lys Glu Glu Lys Met Gln Val Asp Gln Glu Glu
    515                 520                 525

Pro His Val Glu Glu Gln Gln Gln Thr Pro Ala Glu Asn Lys Ala
        530                 535                 540

Glu Ser Glu Glu Met Glu Thr Ser Gln Ala Gly Ser Lys Asp Lys Lys
545                 550                 555                 560

Met Asp Gln Pro Pro Gln Ala Lys Lys Ala Lys Val Lys Thr Ser Thr
```

```
                    565                 570                 575

Val Asp Leu Pro Ile Glu Asn Gln Leu Leu Trp Gln Ile Asp Arg Glu
            580                 585                 590

Met Leu Asn Leu Tyr Ile Glu Asn Glu Gly Lys Met Ile Met Gln Asp
            595                 600                 605

Lys Leu Glu Lys Glu Arg Asn Asp Ala Lys Asn Ala Val Glu Glu Tyr
            610                 615                 620

Val Tyr Glu Met Arg Asp Lys Leu Ser Gly Glu Tyr Glu Lys Phe Val
625                 630                 635                 640

Ser Glu Asp Asp Arg Asn Ser Phe Thr Leu Lys Leu Glu Asp Thr Glu
                645                 650                 655

Asn Trp Leu Tyr Glu Asp Gly Glu Asp Gln Pro Lys Gln Val Tyr Val
            660                 665                 670

Asp Lys Leu Ala Glu Leu Lys Asn Leu Gly Gln Pro Ile Lys Ile Arg
            675                 680                 685

Phe Gln Glu Ser Glu Glu Arg Pro Lys Leu Phe Glu Glu Leu Gly Lys
            690                 695                 700

Gln Ile Gln Gln Tyr Met Lys Ile Ile Ser Ser Phe Lys Asn Lys Glu
705                 710                 715                 720

Asp Gln Tyr Asp His Leu Asp Ala Ala Asp Met Thr Lys Val Glu Lys
                725                 730                 735

Ser Thr Asn Glu Ala Met Glu Trp Met Asn Asn Lys Leu Asn Leu Gln
            740                 745                 750

Asn Lys Gln Ser Leu Thr Met Asp Pro Val Val Lys Ser Lys Glu Ile
            755                 760                 765

Glu Ala Lys Ile Lys Glu Leu Thr Ser Thr Cys Ser Pro Ile Ile Ser
770                 775                 780

Lys Pro Lys Pro Lys Val Glu Pro Pro Lys Glu Gln Lys Asn Ala
785                 790                 795                 800

Glu Gln Asn Gly Pro Val Asp Gly Gln Gly Asp Asn Pro Gly Pro Gln
            805                 810                 815

Ala Ala Glu Gln Gly Thr Asp Thr Ala Val Pro Ser Asp Ser Asp Lys
            820                 825                 830

Lys Leu Pro Glu Met Asp Ile Asp
            835                 840

<210> SEQ ID NO 3
<211> LENGTH: 421
<212> TYPE: PRT
<213> ORGANISM: Homo sapiens

<400> SEQUENCE: 3

Met Asn Arg Gly Phe Ser Arg Lys Ser His Thr Phe Leu Pro Lys Ile
1               5                   10                  15

Phe Phe Arg Lys Met Ser Ser Ser Gly Ala Lys Asp Lys Pro Glu Leu
            20                  25                  30

Gln Phe Pro Phe Leu Gln Asp Glu Asp Thr Val Ala Thr Leu Leu Glu
        35                  40                  45

Cys Lys Thr Leu Phe Ile Leu Arg Gly Leu Pro Gly Ser Gly Lys Ser
    50                  55                  60

Thr Leu Ala Arg Val Ile Val Asp Lys Tyr Arg Asp Gly Thr Lys Met
65              70                  75                  80

Val Ser Ala Asp Ala Tyr Lys Ile Thr Pro Gly Ala Arg Gly Ala Phe
                85                  90                  95
```

-continued

```
Ser Glu Glu Tyr Lys Arg Leu Asp Glu Asp Leu Ala Ala Tyr Cys Arg
                100                 105                 110

Arg Arg Asp Ile Arg Ile Leu Val Leu Asp Asp Thr Asn His Glu Arg
            115                 120                 125

Glu Arg Leu Glu Gln Leu Phe Glu Met Ala Asp Gln Tyr Gln Tyr Gln
        130                 135                 140

Val Val Leu Val Glu Pro Lys Thr Ala Trp Arg Leu Asp Cys Ala Gln
145                 150                 155                 160

Leu Lys Glu Lys Asn Gln Trp Gln Leu Ser Ala Asp Asp Leu Lys Lys
                165                 170                 175

Leu Lys Pro Gly Leu Glu Lys Asp Phe Leu Pro Leu Tyr Phe Gly Trp
            180                 185                 190

Phe Leu Thr Lys Lys Ser Ser Glu Thr Leu Arg Lys Ala Gly Gln Val
        195                 200                 205

Phe Leu Glu Glu Leu Gly Asn His Lys Ala Phe Lys Lys Glu Leu Arg
210                 215                 220

Gln Phe Val Pro Gly Asp Glu Pro Arg Glu Lys Met Asp Leu Val Thr
225                 230                 235                 240

Tyr Phe Gly Lys Arg Pro Pro Gly Val Leu His Cys Thr Thr Lys Phe
                245                 250                 255

Cys Asp Tyr Gly Lys Ala Pro Gly Ala Glu Glu Tyr Ala Gln Gln Asp
            260                 265                 270

Val Leu Lys Lys Ser Tyr Ser Lys Ala Phe Thr Leu Thr Ile Ser Ala
        275                 280                 285

Leu Phe Val Thr Pro Lys Thr Thr Gly Ala Arg Val Glu Leu Ser Glu
290                 295                 300

Gln Gln Leu Gln Leu Trp Pro Ser Asp Val Asp Lys Leu Ser Pro Thr
305                 310                 315                 320

Asp Asn Leu Pro Arg Gly Ser Arg Ala His Ile Thr Leu Gly Cys Ala
                325                 330                 335

Ala Asp Val Glu Ala Val Gln Thr Gly Leu Asp Leu Leu Glu Ile Leu
            340                 345                 350

Arg Gln Glu Lys Gly Gly Ser Arg Gly Glu Val Gly Glu Leu Ser
        355                 360                 365

Arg Gly Lys Leu Tyr Ser Leu Gly Asn Gly Arg Trp Met Leu Thr Leu
370                 375                 380

Ala Lys Asn Met Glu Val Arg Ala Ile Phe Thr Gly Tyr Tyr Gly Lys
385                 390                 395                 400

Gly Lys Pro Val Pro Thr Gln Gly Ser Arg Lys Gly Gly Ala Leu Gln
                405                 410                 415

Ser Cys Thr Ile Ile
            420

<210> SEQ ID NO 4
<211> LENGTH: 183
<212> TYPE: PRT
<213> ORGANISM: Homo sapiens

<400> SEQUENCE: 4

Met Ser Gln Lys Pro Ala Lys Glu Gly Pro Arg Leu Ser Lys Asn Gln
1               5                   10                  15

Lys Tyr Ser Glu His Phe Ser Ile His Cys Cys Pro Pro Phe Thr Phe
            20                  25                  30

Leu Asn Ser Lys Lys Glu Ile Val Asp Arg Lys Tyr Ser Ile Cys Lys
        35                  40                  45
```

```
Ser Gly Cys Phe Tyr Gln Lys Lys Glu Glu Asp Trp Ile Cys Cys Ala
    50                  55                  60

Cys Gln Lys Thr Arg Thr Ser Arg Arg Ala Lys Pro Pro Gln Arg Pro
65                  70                  75                  80

Lys Gln Gln Pro Ala Ala Pro Ala Val Val Arg Ala Pro Ala Lys
                85                  90                  95

Pro Arg Ser Pro Pro Arg Ser Glu Arg Gln Pro Arg Ser Pro Pro Arg
                100                 105                 110

Ser Glu Arg Gln Pro Arg Ser Pro Pro Arg Ser Glu Arg Gln Pro Arg
            115                 120                 125

Ser Pro Pro Arg Ser Glu Arg Gln Pro Arg Pro Arg Pro Glu Val Arg
        130                 135                 140

Pro Pro Pro Ala Lys Gln Arg Pro Pro Gln Lys Ser Lys Gln Pro
145                 150                 155                 160

Arg Ser Ser Pro Leu Arg Gly Pro Gly Ala Ser Arg Gly Gly Ser Pro
                165                 170                 175

Val Lys Ala Ser Arg Phe Trp
            180
```

<210> SEQ ID NO 5
<211> LENGTH: 247
<212> TYPE: PRT
<213> ORGANISM: Homo sapiens

<400> SEQUENCE: 5

```
Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
                20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
    210                 215                 220

Ile Ile Cys Tyr Asn Trp Leu His Arg Arg Leu Ala Gly Gln Phe Leu
```

```
            225                 230                 235                 240

Glu Glu Leu Arg Asn Pro Phe
                245

<210> SEQ ID NO 6
<211> LENGTH: 197
<212> TYPE: PRT
<213> ORGANISM: Homo sapiens

<400> SEQUENCE: 6

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 7
<211> LENGTH: 179
<212> TYPE: PRT
<213> ORGANISM: Bos taurus

<400> SEQUENCE: 7

Ser Asp Glu Leu Gln Thr Ile Gln Glu Asp Ser Ala Ala Ala Pro Gly
1               5                   10                  15

Ala Val Asp Ala Met Ala Ala Gln Lys Arg Pro Ser Gln Arg Ser Lys
            20                  25                  30

Tyr Leu Ala Ser Ala Ser Thr Met Asp His Ala Arg His Gly Phe Leu
        35                  40                  45

Pro Arg His Arg Asp Thr Gly Ile Leu Asp Ser Leu Gly Arg Phe Phe
    50                  55                  60

Gly Ser Asp Arg Gly Ala Pro Lys Arg Gly Gly Gly Lys Asp Gly His
65                  70                  75                  80

His Ala Ala Arg Thr Thr His Tyr Gly Ser Leu Pro Gln Lys Ala Gln
                85                  90                  95

His Gly Arg Pro Gln Asp Glu Asn Pro Val Val His Phe Phe Lys Asn
```

Ile Val Thr Pro Arg Thr Pro Pro Ser Gln Gly Lys Gly Ala Glu
            100                 105                 110
Gly Gln Lys Pro Gly Phe Gly Tyr Gly Gly Arg Ala Ser Asp Tyr Lys
        115                 120                 125
Ser Ala His Lys Gly Leu Lys Gly His Asp Ala Gln Gly Thr Leu Ser
130                 135                 140                 
Lys Ile Phe Lys Leu Gly Gly Arg Asp Ser Arg Ser Gly Ser Pro Met
        145                 150                 155                 160
Ala Arg Arg
        165                 170                 175

<210> SEQ ID NO 8
<211> LENGTH: 250
<212> TYPE: PRT
<213> ORGANISM: Mus musculus

<400> SEQUENCE: 8

Met Gly Asn His Ser Gly Lys Arg Glu Leu Ser Ala Glu Lys Ala Ser
1               5                   10                  15

Lys Asp Gly Glu Ile His Arg Gly Glu Ala Gly Lys Lys Arg Ser Val
            20                  25                  30

Gly Lys Leu Ser Gln Thr Ala Ser Glu Asp Ser Asp Val Phe Gly Glu
        35                  40                  45

Ala Asp Ala Ile Gln Asn Asn Gly Thr Ser Ala Glu Asp Thr Ala Val
    50                  55                  60

Thr Asp Ser Lys His Thr Ala Asp Pro Lys Asn Asn Trp Gln Gly Ala
65                  70                  75                  80

His Pro Ala Asp Pro Gly Asn Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Pro Thr Ala Ala Ser
        115                 120                 125

Gly Gly Leu Asp Val Met Ala Ser Gln Lys Arg Pro Ser Gln Arg Ser
    130                 135                 140

Lys Tyr Leu Ala Thr Ala Ser Thr Met Asp His Ala Arg His Gly Phe
145                 150                 155                 160

Leu Pro Arg His Arg Asp Thr Gly Ile Leu Asp Ser Ile Gly Arg Phe
                165                 170                 175

Phe Ser Gly Asp Arg Gly Ala Pro Lys Arg Gly Ser Gly Lys Asp Ser
            180                 185                 190

His Thr Arg Thr Thr His Tyr Gly Ser Leu Pro Gln Lys Ser Gln His
        195                 200                 205

Gly Arg Thr Gln Asp Glu Asn Pro Val Val His Phe Phe Lys Asn Ile
    210                 215                 220

Val Thr Pro Arg Thr Pro Pro Ser Gln Gly Lys Gly Gly Arg Asp
225                 230                 235                 240

Ser Arg Ser Gly Ser Pro Met Ala Arg Arg
                245                 250

<210> SEQ ID NO 9
<211> LENGTH: 150
<212> TYPE: PRT
<213> ORGANISM: Cavia porcellus

<400> SEQUENCE: 9

```
Ser Gln Arg His Gly Ser Lys Tyr Leu Ala Thr Ala Ser Thr Met Asp
1               5                   10                  15

His Ala Arg His Gly Phe Leu Pro Arg His Arg Asp Thr Gly Ile Leu
                20                  25                  30

Asp Ser Ile Gly Arg Phe Phe Gly Ser Asp Arg Ala Ala Pro Lys Arg
            35                  40                  45

Gly Ser Gly Lys Asp Ser His His Ala Ala Arg Thr Thr His Tyr Gly
        50                  55                  60

Ser Leu Pro Gln Lys Ser Gln Arg Ser Gln Asp Glu Asn Pro Val Val
65                  70                  75                  80

His Phe Phe Lys Asn Ile Val Thr Pro Arg Thr Pro Pro Ser Gln
                85                  90                  95

Gly Lys Gly Arg Gly Leu Ser Leu Ser Arg Phe Ser Trp Gly Ala Glu
            100                 105                 110

Gly Gln Lys Pro Gly Phe Gly Tyr Gly Gly Arg Ala Asp Tyr Lys Ser
            115                 120                 125

Lys Gly Phe Lys Gly Ala His Asp Ala Gln Gly Thr Leu Ser Lys Ile
            130                 135                 140

Phe Lys Leu Gly Gly Arg
145                 150

<210> SEQ ID NO 10
<211> LENGTH: 132
<212> TYPE: PRT
<213> ORGANISM: Homo sapiens

<400> SEQUENCE: 10

Met Ser Asn Lys Phe Leu Gly Thr Trp Lys Leu Val Ser Ser Glu Asn
1               5                   10                  15

Phe Asp Asp Tyr Met Lys Ala Leu Gly Val Gly Leu Ala Thr Arg Lys
                20                  25                  30

Leu Gly Asn Leu Ala Lys Pro Thr Val Ile Ile Ser Lys Lys Gly Asp
            35                  40                  45

Ile Ile Thr Ile Arg Thr Glu Ser Thr Phe Lys Asn Thr Glu Ile Ser
        50                  55                  60

Phe Lys Leu Gly Gln Glu Phe Glu Glu Thr Thr Ala Asp Asn Arg Lys
65                  70                  75                  80

Thr Lys Ser Ile Val Thr Leu Gln Arg Gly Ser Leu Asn Gln Val Gln
                85                  90                  95

Arg Trp Asp Gly Lys Glu Thr Thr Ile Lys Arg Lys Leu Val Asn Gly
            100                 105                 110

Lys Met Val Ala Glu Cys Lys Met Lys Gly Val Val Cys Thr Arg Ile
            115                 120                 125

Tyr Glu Lys Val
            130

<210> SEQ ID NO 11
<211> LENGTH: 217
<212> TYPE: PRT
<213> ORGANISM: Homo sapiens

<400> SEQUENCE: 11

Val Ala Thr Cys Leu Gln Val Val Gly Phe Val Thr Ser Phe Val Gly
1               5                   10                  15

Trp Ile Gly Val Ile Val Thr Thr Ser Thr Asn Asp Trp Val Val Thr
                20                  25                  30
```

```
Cys Gly Tyr Thr Ile Pro Thr Cys Arg Lys Leu Asp Glu Leu Gly Ser
            35                  40                  45

Lys Gly Leu Trp Ala Asp Cys Val Met Ala Thr Gly Leu Tyr His Cys
 50                  55                  60

Lys Pro Leu Val Asp Ile Leu Ile Leu Pro Gly Tyr Val Gln Ala Cys
 65                  70                  75                  80

Arg Ala Leu Met Ile Ala Ala Ser Val Leu Gly Leu Pro Ala Ile Leu
                85                  90                  95

Leu Leu Leu Thr Val Leu Pro Cys Ile Arg Met Gly Gln Glu Pro Gly
            100                 105                 110

Val Ala Lys Tyr Arg Arg Ala Gln Leu Ala Gly Val Leu Leu Ile Leu
            115                 120                 125

Leu Ala Leu Cys Ala Leu Val Ala Thr Ile Trp Phe Pro Val Cys Ala
            130                 135                 140

His Arg Glu Thr Thr Ile Val Ser Phe Gly Tyr Ser Leu Tyr Ala Gly
145                 150                 155                 160

Trp Ile Gly Ala Val Leu Cys Leu Val Gly Gly Cys Val Ile Leu Cys
                165                 170                 175

Cys Ala Gly Asp Ala Gln Ala Phe Gly Glu Asn Val Ser Thr Thr Leu
            180                 185                 190

Arg Ala Leu Ala Pro Arg Leu Met Arg Arg Val Pro Thr Tyr Lys Arg
            195                 200                 205

Ala Ala Arg Leu Pro Thr Glu Val Leu
            210                 215

<210> SEQ ID NO 12
<211> LENGTH: 277
<212> TYPE: PRT
<213> ORGANISM: Homo sapiens

<400> SEQUENCE: 12

Met Gly Leu Leu Glu Cys Cys Ala Arg Cys Leu Val Gly Ala Pro Phe
 1               5                  10                  15

Ala Ser Leu Val Ala Thr Gly Leu Cys Phe Phe Gly Val Ala Leu Phe
                20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
 50                  55                  60

Ile His Ala Phe Gln Tyr Val Ile Tyr Gly Thr Ala Ser Phe Phe Phe
 65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
            115                 120                 125

Gln His Gln Ala His Ser Leu Glu Arg Val Cys His Cys Leu Gly Lys
            130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
```

```
            180                 185                 190
Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
    210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275

<210> SEQ ID NO 13
<211> LENGTH: 43
<212> TYPE: PRT
<213> ORGANISM: Homo sapiens

<400> SEQUENCE: 13

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
            35                  40

<210> SEQ ID NO 14
<211> LENGTH: 432
<212> TYPE: PRT
<213> ORGANISM: Homo sapiens

<400> SEQUENCE: 14

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
                20                  25                  30

Pro Gly Thr Arg Leu Ser Leu Ala Arg Met Pro Pro Pro Leu Pro Thr
            35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
    130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
```

```
                180                 185                 190
Leu Glu Glu Glu Ile Arg Phe Leu Arg Lys Ile His Glu Glu Val
            195                 200                 205
Arg Glu Leu Gln Glu Gln Leu Ala Arg Gln Gln Val His Val Glu Leu
        210                 215                 220
Asp Val Ala Lys Pro Asp Leu Thr Ala Ala Leu Lys Glu Ile Arg Thr
225                 230                 235                 240
Gln Tyr Glu Ala Met Ala Ser Ser Asn Met His Glu Ala Glu Trp
                245                 250                 255
Tyr Arg Ser Lys Phe Ala Asp Leu Thr Asp Ala Ala Ala Arg Asn Ala
                260                 265                 270
Glu Leu Leu Arg Gln Ala Lys His Glu Ala Asn Asp Tyr Arg Arg Gln
            275                 280                 285
Leu Gln Ser Leu Thr Cys Asp Leu Glu Ser Leu Arg Gly Thr Asn Glu
        290                 295                 300
Ser Leu Glu Arg Gln Met Arg Glu Gln Glu Glu Arg His Val Arg Glu
305                 310                 315                 320
Ala Ala Ser Tyr Gln Glu Ala Leu Ala Arg Leu Glu Glu Gly Gln
                325                 330                 335
Ser Leu Lys Asp Glu Met Ala Arg His Leu Gln Glu Tyr Gln Asp Leu
            340                 345                 350
Leu Asn Val Lys Leu Ala Leu Asp Ile Glu Ile Ala Thr Tyr Arg Lys
        355                 360                 365
Leu Leu Glu Gly Glu Glu Asn Arg Ile Thr Ile Pro Val Gln Thr Phe
    370                 375                 380
Ser Asn Leu Gln Ile Arg Glu Thr Ser Leu Asp Thr Lys Ser Val Ser
385                 390                 395                 400
Glu Gly His Leu Lys Arg Asn Ile Val Val Lys Thr Val Glu Met Arg
                405                 410                 415
Asp Gly Glu Val Ile Lys Glu Ser Lys Gln Glu His Lys Asp Val Met
            420                 425                 430

<210> SEQ ID NO 15
<211> LENGTH: 215
<212> TYPE: PRT
<213> ORGANISM: Homo sapiens

<400> SEQUENCE: 15

Met Glu Thr Gln Ala Glu Gln Gln Leu Glu Thr Leu Pro Thr Thr
1               5                   10                  15
Lys Met Ala Gln Thr Asn Pro Thr Pro Gly Ser Leu Gly Pro Trp Lys
                20                  25                  30
Ile Thr Ile Tyr Asp Gln Glu Asn Phe Gln Gly Lys Arg Met Glu Phe
            35                  40                  45
Thr Ser Ser Cys Pro Asn Val Ser Glu Arg Ser Phe Asp Asn Val Arg
        50                  55                  60
Ser Leu Lys Val Glu Ser Gly Ala Trp Ile Gly Tyr Glu His Thr Ser
65                  70                  75                  80
Phe Cys Gly Gln Gln Phe Ile Leu Glu Arg Gly Glu Tyr Pro Arg Trp
                85                  90                  95
Asp Ala Trp Ser Gly Ser Asn Ala Tyr His Ile Glu Arg Leu Met Ser
            100                 105                 110
Phe Arg Pro Ile Cys Ser Ala Asn His Lys Glu Ser Lys Met Thr Ile
        115                 120                 125
```

```
Phe Glu Lys Glu Asn Phe Ile Gly Arg Gln Trp Glu Ile Ser Asp Asp
    130                 135                 140
Tyr Pro Ser Leu Gln Ala Met Gly Trp Phe Asn Asn Glu Val Gly Ser
145                 150                 155                 160
Met Lys Ile Gln Ser Gly Ala Trp Val Cys Tyr Gln Tyr Pro Gly Tyr
                165                 170                 175
Arg Gly Tyr Gln Tyr Ile Leu Glu Cys Asp His His Gly Gly Asp Tyr
            180                 185                 190
Lys His Trp Arg Glu Trp Gly Ser His Ala Gln Thr Ser Gln Ile Gln
        195                 200                 205
Ser Ile Arg Arg Ile Gln Gln
    210                 215
```

<210> SEQ ID NO 16
<211> LENGTH: 543
<212> TYPE: PRT
<213> ORGANISM: Homo sapiens

<400> SEQUENCE: 16

```
Met Ser Ser Phe Ser Tyr Glu Pro Tyr Tyr Ser Thr Ser Tyr Lys Arg
1               5                   10                  15
Arg Tyr Val Glu Thr Pro Arg Val His Ile Ser Ser Val Arg Ser Gly
            20                  25                  30
Tyr Ser Thr Ala Arg Ser Ala Tyr Ser Ser Tyr Ser Ala Pro Val Ser
        35                  40                  45
Ser Ser Leu Ser Val Arg Arg Ser Tyr Ser Ser Ser Gly Ser Leu
    50                  55                  60
Met Pro Ser Leu Glu Asn Leu Asp Leu Ser Gln Val Ala Ala Ile Ser
65                  70                  75                  80
Asn Asp Leu Lys Ser Ile Arg Thr Gln Glu Lys Ala Gln Leu Gln Asp
                85                  90                  95
Leu Asn Asp Arg Phe Ala Ser Phe Ile Glu Arg Val His Glu Leu Glu
            100                 105                 110
Gln Gln Asn Lys Val Leu Glu Ala Glu Leu Leu Val Leu Arg Gln Lys
        115                 120                 125
His Ser Glu Pro Ser Arg Phe Arg Ala Leu Tyr Glu Gln Glu Ile Arg
    130                 135                 140
Asp Leu Arg Leu Ala Ala Glu Asp Ala Thr Asn Glu Lys Gln Ala Leu
145                 150                 155                 160
Gln Gly Glu Arg Glu Gly Leu Glu Glu Thr Leu Arg Asn Leu Gln Ala
                165                 170                 175
Arg Tyr Glu Glu Glu Val Leu Ser Arg Glu Asp Ala Glu Gly Arg Leu
            180                 185                 190
Met Glu Ala Arg Lys Gly Ala Asp Glu Ala Ala Leu Ala Arg Ala Glu
        195                 200                 205
Leu Glu Lys Arg Ile Asp Ser Leu Met Asp Glu Ile Ser Phe Leu Lys
    210                 215                 220
Lys Val His Glu Glu Glu Ile Ala Glu Leu Gln Ala Gln Ile Gln Tyr
225                 230                 235                 240
Ala Gln Ile Ser Val Glu Met Asp Val Thr Lys Pro Asp Leu Ser Ala
                245                 250                 255
Ala Leu Lys Asp Ile Arg Ala Gln Tyr Glu Lys Leu Ala Ala Lys Asn
            260                 265                 270
Met Gln Asn Ala Glu Glu Trp Phe Lys Ser Arg Phe Thr Val Leu Thr
        275                 280                 285
```

Glu Ser Ala Ala Lys Asn Thr Asp Ala Val Arg Ala Ala Lys Asp Glu
    290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                325                 330                 335

Glu Asp Lys Gln Asn Ala Asp Ile Ser Ala Met Gln Asp Thr Ile Asn
            340                 345                 350

Lys Leu Glu Asn Glu Leu Arg Thr Thr Lys Ser Glu Met Ala Arg Tyr
        355                 360                 365

Leu Lys Glu Tyr Gln Asp Leu Leu Asn Val Lys Met Ala Leu Asp Ile
    370                 375                 380

Glu Ile Ala Ala Tyr Arg Lys Leu Leu Glu Gly Glu Thr Arg Leu
385                 390                 395                 400

Ser Phe Thr Ser Val Gly Ser Ile Thr Ser Gly Tyr Ser Gln Ser Ser
                405                 410                 415

Gln Val Phe Gly Arg Ser Ala Tyr Gly Gly Leu Gln Thr Ser Ser Tyr
            420                 425                 430

Leu Met Ser Thr Arg Ser Phe Pro Ser Tyr Tyr Thr Ser His Val Gln
        435                 440                 445

Glu Glu Gln Ile Glu Val Glu Glu Thr Ile Glu Ala Ala Lys Ala Glu
    450                 455                 460

Glu Ala Lys Asp Glu Pro Pro Ser Glu Gly Glu Ala Glu Glu Glu Glu
465                 470                 475                 480

Lys Asp Lys Glu Glu Ala Glu Glu Glu Ala Ala Glu Glu Glu Glu
                485                 490                 495

Ala Ala Lys Glu Glu Ser Glu Glu Ala Lys Glu Glu Glu Glu Gly Gly
            500                 505                 510

Glu Gly Glu Glu Gly Glu Glu Thr Lys Glu Ala Glu Glu Glu Glu Lys
        515                 520                 525

Lys Val Glu Gly Ala Gly Glu Glu Gln Ala Ala Lys Lys Lys Asp
    530                 535                 540

<210> SEQ ID NO 17
<211> LENGTH: 916
<212> TYPE: PRT
<213> ORGANISM: Homo sapiens

<400> SEQUENCE: 17

Met Ser Tyr Thr Leu Asp Ser Leu Gly Asn Pro Ser Ala Tyr Arg Arg
1               5                   10                  15

Val Thr Glu Thr Arg Ser Ser Phe Ser Arg Val Ser Gly Ser Pro Ser
            20                  25                  30

Ser Gly Phe Arg Ser Gln Ser Trp Ser Arg Gly Ser Pro Ser Thr Val
        35                  40                  45

Ser Ser Ser Tyr Lys Arg Ser Met Leu Ala Pro Arg Leu Ala Tyr Ser
    50                  55                  60

Ser Ala Met Leu Ser Ser Ala Glu Ser Ser Leu Asp Phe Ser Gln Ser
65                  70                  75                  80

Ser Ser Leu Leu Asn Gly Gly Ser Gly Pro Gly Gly Asp Tyr Lys Leu
                85                  90                  95

Ser Arg Ser Asn Glu Lys Glu Gln Leu Gln Gly Leu Asn Asp Arg Phe
            100                 105                 110

Ala Gly Tyr Ile Glu Lys Val His Tyr Leu Glu Gln Gln Asn Lys Glu

-continued

```
            115                 120                 125
Ile Glu Ala Glu Ile Gln Ala Leu Arg Gln Lys Gln Ala Ser His Ala
            130                 135                 140
Gln Leu Gly Asp Ala Tyr Asp Gln Glu Ile Arg Glu Leu Arg Ala Thr
145                 150                 155                 160
Leu Glu Met Val Asn His Glu Lys Ala Gln Val Gln Leu Asp Ser Asp
                    165                 170                 175
His Leu Glu Glu Asp Ile His Arg Leu Lys Glu Arg Phe Glu Glu Glu
                    180                 185                 190
Ala Arg Leu Arg Asp Asp Thr Glu Ala Ala Ile Arg Ala Leu Arg Lys
                    195                 200                 205
Asp Ile Glu Glu Ala Ser Leu Val Lys Val Glu Leu Asp Lys Lys Val
            210                 215                 220
Gln Ser Leu Gln Asp Glu Val Ala Phe Leu Arg Ser Asn His Glu Glu
225                 230                 235                 240
Glu Val Ala Asp Leu Leu Ala Gln Ile Gln Ala Ser His Ile Thr Val
                    245                 250                 255
Glu Arg Lys Asp Tyr Leu Lys Thr Asp Ile Ser Thr Ala Leu Lys Glu
                    260                 265                 270
Ile Arg Ser Gln Leu Glu Ser His Ser Asp Gln Asn Met His Gln Ala
            275                 280                 285
Glu Glu Trp Phe Lys Cys Arg Tyr Ala Lys Leu Thr Glu Ala Ala Glu
290                 295                 300
Gln Asn Lys Glu Ala Ile Arg Ser Ala Lys Glu Glu Ile Ala Glu Tyr
305                 310                 315                 320
Arg Arg Gln Leu Gln Ser Lys Ser Ile Glu Leu Glu Ser Val Arg Gly
                    325                 330                 335
Thr Lys Glu Ser Leu Glu Arg Gln Leu Ser Asp Ile Glu Glu Arg His
                    340                 345                 350
Asn His Asp Leu Ser Ser Tyr Gln Asp Thr Ile Gln Gln Leu Glu Asn
            355                 360                 365
Glu Leu Arg Gly Thr Lys Trp Glu Met Ala Arg His Leu Arg Glu Tyr
370                 375                 380
Gln Asp Leu Leu Asn Val Lys Met Ala Leu Asp Ile Glu Ile Ala Ala
385                 390                 395                 400
Tyr Arg Lys Leu Leu Glu Gly Glu Glu Thr Arg Phe Ser Thr Phe Ala
                    405                 410                 415
Gly Ser Ile Thr Gly Pro Leu Tyr Thr His Arg Pro Ile Thr Ile
                    420                 425                 430
Ser Ser Lys Ile Gln Lys Pro Lys Val Glu Ala Pro Lys Leu Lys Val
            435                 440                 445
Gln His Lys Phe Val Glu Ile Ile Glu Glu Thr Lys Val Glu Asp
            450                 455                 460
Glu Lys Ser Glu Met Glu Glu Ala Leu Thr Ala Ile Thr Glu Glu Leu
465                 470                 475                 480
Ala Val Ser Met Lys Glu Lys Lys Glu Ala Ala Glu Lys Glu
                    485                 490                 495
Glu Glu Pro Glu Ala Glu Glu Glu Val Ala Ala Lys Lys Ser Pro
                    500                 505                 510
Val Lys Ala Thr Ala Pro Glu Val Lys Glu Glu Gly Lys Glu
            515                 520                 525
Glu Glu Glu Gly Gln Glu Glu Glu Glu Glu Asp Glu Gly Ala Lys
            530                 535                 540
```

```
Ser Asp Gln Ala Glu Glu Gly Gly Ser Glu Lys Gly Ser Glu
545                 550                 555                 560

Lys Glu Glu Gly Glu Gln Glu Gly Glu Thr Glu Ala Glu Ala Glu
                565                 570                 575

Gly Glu Glu Ala Glu Ala Lys Glu Glu Lys Lys Val Glu Lys Ser
            580                 585                 590

Glu Glu Val Ala Thr Lys Glu Glu Leu Val Ala Asp Ala Lys Val Glu
            595                 600                 605

Lys Pro Glu Lys Ala Lys Ser Pro Val Pro Lys Ser Pro Val Glu Glu
            610                 615                 620

Lys Gly Lys Ser Pro Val Pro Lys Ser Pro Val Glu Glu Lys Gly Lys
625                 630                 635                 640

Ser Pro Val Pro Lys Ser Pro Val Glu Glu Lys Gly Lys Ser Pro Val
                645                 650                 655

Pro Lys Ser Pro Val Glu Glu Lys Gly Lys Ser Pro Val Ser Lys Ser
            660                 665                 670

Pro Val Glu Glu Lys Ala Lys Ser Pro Val Pro Lys Ser Pro Val Glu
            675                 680                 685

Glu Ala Lys Ser Lys Ala Glu Val Gly Lys Gly Glu Gln Lys Glu Glu
            690                 695                 700

Glu Glu Lys Glu Val Lys Glu Ala Pro Lys Glu Glu Lys Val Glu Lys
705                 710                 715                 720

Lys Glu Glu Lys Pro Lys Asp Val Pro Glu Lys Lys Ala Glu Ser
                725                 730                 735

Pro Val Lys Glu Glu Ala Val Ala Glu Val Val Thr Ile Thr Lys Ser
            740                 745                 750

Val Lys Val His Leu Glu Lys Glu Thr Lys Glu Glu Gly Lys Pro Leu
            755                 760                 765

Gln Gln Glu Lys Glu Lys Glu Lys Ala Gly Gly Glu Gly Gly Ser Glu
            770                 775                 780

Glu Glu Gly Ser Asp Lys Gly Ala Lys Gly Ser Arg Lys Glu Asp Ile
785                 790                 795                 800

Ala Val Asn Gly Glu Val Glu Gly Lys Glu Glu Val Glu Gln Glu Thr
                805                 810                 815

Lys Glu Lys Gly Ser Gly Arg Glu Glu Glu Lys Gly Val Val Thr Asn
            820                 825                 830

Gly Leu Asp Leu Ser Pro Ala Asp Glu Lys Lys Gly Gly Asp Lys Ser
            835                 840                 845

Glu Glu Lys Val Val Val Thr Lys Thr Val Glu Lys Ile Thr Ser Glu
            850                 855                 860

Gly Gly Asp Gly Ala Thr Lys Tyr Ile Thr Lys Ser Val Thr Val Thr
865                 870                 875                 880

Gln Lys Val Glu Glu His Glu Glu Thr Phe Glu Glu Lys Leu Val Ser
                885                 890                 895

Thr Lys Lys Val Glu Lys Val Thr Ser His Ala Ile Val Lys Glu Val
            900                 905                 910

Thr Gln Ser Asp
            915

<210> SEQ ID NO 18
<211> LENGTH: 695
<212> TYPE: PRT
<213> ORGANISM: Homo sapiens
```

```
<400> SEQUENCE: 18

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285

Val Pro Thr Thr Ala Ala Ser Thr Pro Asp Ala Val Asp Lys Tyr Leu
290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415
```

```
Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
            595                 600                 605

His His Gln Lys Leu Val Phe Phe Ala Glu Asp Val Gly Ser Asn Lys
            610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
            690             695

<210> SEQ ID NO 19
<211> LENGTH: 201
<212> TYPE: PRT
<213> ORGANISM: Homo sapiens

<400> SEQUENCE: 19

Met Lys Trp Val Trp Ala Leu Leu Leu Leu Ala Ala Leu Gly Ser Gly
1               5                   10                  15

Arg Ala Glu Arg Asp Cys Arg Val Ser Ser Phe Arg Val Lys Glu Asn
                20                  25                  30

Phe Asp Lys Ala Arg Phe Ser Gly Thr Trp Tyr Ala Met Ala Lys Lys
            35                  40                  45

Asp Pro Glu Gly Leu Phe Leu Gln Asp Asn Ile Val Ala Glu Phe Ser
        50                  55                  60

Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
```

```
                85                  90                  95
Asp Thr Glu Asp Pro Ala Lys Phe Lys Met Lys Tyr Trp Gly Val Ala
                100                 105                 110

Ser Phe Leu Gln Lys Gly Asn Asp Asp His Trp Ile Val Asp Thr Asp
                115                 120                 125

Tyr Asp Thr Tyr Ala Val Gln Tyr Ser Cys Arg Leu Leu Asn Leu Asp
            130                 135                 140

Gly Thr Cys Ala Asp Ser Tyr Ser Phe Val Phe Ser Arg Asp Pro Asn
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
                180                 185                 190

Asp Gly Arg Ser Glu Arg Asn Leu Leu
                195                 200

<210> SEQ ID NO 20
<211> LENGTH: 770
<212> TYPE: PRT
<213> ORGANISM: Homo sapiens

<400> SEQUENCE: 20

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
                35                  40                  45

Asn Gly Lys Trp Asp Ser Asp Pro Ser Gly Thr Lys Thr Cys Ile Asp
            50                  55                  60

Thr Lys Glu Gly Ile Leu Gln Tyr Cys Gln Glu Val Tyr Pro Glu Leu
65              70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
                115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255
```

-continued

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu

```
              675                 680                 685
Val Phe Phe Ala Glu Asp Val Gly Ser Asn Lys Gly Ala Ile Ile Gly
            690                 695                 700

Leu Met Val Gly Gly Val Ile Ala Thr Val Ile Val Ile Thr Leu
705                 710                 715                 720

Val Met Leu Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
                755                 760                 765

Gln Asn
    770

<210> SEQ ID NO 21
<211> LENGTH: 751
<212> TYPE: PRT
<213> ORGANISM: Homo sapiens

<400> SEQUENCE: 21

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270
```

```
Ala Thr Thr Thr Thr Thr Thr Glu Ser Val Glu Val Val Arg
    275             280             285

Glu Val Cys Ser Glu Gln Ala Glu Thr Gly Pro Cys Arg Ala Met Ile
290             295             300

Ser Arg Trp Tyr Phe Asp Val Thr Glu Gly Lys Cys Ala Pro Phe Phe
305             310             315             320

Tyr Gly Gly Cys Gly Gly Asn Arg Asn Asn Phe Asp Thr Glu Glu Tyr
                325             330             335

Cys Met Ala Val Cys Gly Ser Ala Ile Pro Thr Thr Ala Ala Ser Thr
            340             345             350

Pro Asp Ala Val Asp Lys Tyr Leu Glu Thr Pro Gly Asp Glu Asn Glu
        355             360             365

His Ala His Phe Gln Lys Ala Lys Glu Arg Leu Glu Ala Lys His Arg
    370             375             380

Glu Arg Met Ser Gln Val Met Arg Glu Trp Glu Glu Ala Glu Arg Gln
385             390             395             400

Ala Lys Asn Leu Pro Lys Ala Asp Lys Lys Ala Val Ile Gln His Phe
                405             410             415

Gln Glu Lys Val Glu Ser Leu Glu Gln Glu Ala Ala Asn Glu Arg Gln
            420             425             430

Gln Leu Val Glu Thr His Met Ala Arg Val Glu Ala Met Leu Asn Asp
        435             440             445

Arg Arg Arg Leu Ala Leu Glu Asn Tyr Ile Thr Ala Leu Gln Ala Val
    450             455             460

Pro Pro Arg Pro Arg His Val Phe Asn Met Leu Lys Lys Tyr Val Arg
465             470             475             480

Ala Glu Gln Lys Asp Arg Gln His Thr Leu Lys His Phe Glu His Val
                485             490             495

Arg Met Val Asp Pro Lys Lys Ala Ala Gln Ile Arg Ser Gln Val Met
            500             505             510

Thr His Leu Arg Val Ile Tyr Glu Arg Met Asn Gln Ser Leu Ser Leu
        515             520             525

Leu Tyr Asn Val Pro Ala Val Ala Glu Glu Ile Gln Asp Glu Val Asp
    530             535             540

Glu Leu Leu Gln Lys Glu Gln Asn Tyr Ser Asp Asp Val Leu Ala Asn
545             550             555             560

Met Ile Ser Glu Pro Arg Ile Ser Tyr Gly Asn Asp Ala Leu Met Pro
                565             570             575

Ser Leu Thr Glu Thr Lys Thr Thr Val Glu Leu Leu Pro Val Asn Gly
            580             585             590

Glu Phe Ser Leu Asp Asp Leu Gln Pro Trp His Ser Phe Gly Ala Asp
        595             600             605

Ser Val Pro Ala Asn Thr Glu Asn Glu Val Glu Pro Val Asp Ala Arg
    610             615             620

Pro Ala Ala Asp Arg Gly Leu Thr Thr Arg Pro Gly Ser Gly Leu Thr
625             630             635             640

Asn Ile Lys Thr Glu Glu Ile Ser Glu Val Lys Met Asp Ala Glu Phe
                645             650             655

Arg His Asp Ser Gly Tyr Glu Val His His Gln Lys Leu Val Phe Phe
            660             665             670

Ala Glu Asp Val Gly Ser Asn Lys Gly Ala Ile Ile Gly Leu Met Val
        675             680             685

Gly Gly Val Val Ile Ala Thr Val Ile Val Ile Thr Leu Val Met Leu
```

```
                690                 695                 700
Lys Lys Lys Gln Tyr Thr Ser Ile His His Gly Val Glu Val Asp
705                 710                 715                 720

Ala Ala Val Thr Pro Glu Arg His Leu Ser Lys Met Gln Gln Asn
                725                 730                 735

Gly Tyr Glu Asn Pro Thr Tyr Lys Phe Phe Glu Gln Met Gln Asn
                740                 745                 750

<210> SEQ ID NO 22
<211> LENGTH: 154
<212> TYPE: PRT
<213> ORGANISM: Homo sapiens

<400> SEQUENCE: 22

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Ala Asn Gly Ile Leu Asn Val Thr Ala Thr Asp Lys Ser Thr Gly Lys
1               5                   10                  15

Ala Asn Lys Ile
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

Lys Glu Glu Ile Glu Arg Met Val Gln Glu Ala Glu Lys Tyr Lys Ala
1               5                   10                  15

Glu Asp Glu Val
```

20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptide

<400> SEQUENCE: 25

Leu Val Leu Asn Arg Leu Lys Val Gly Leu Gln Val Val Ala Val Lys
1               5                   10                  15

Ala Pro Gly Phe
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Gln Ser Ser Ser Glu Val Gly Tyr Asp Ala Met Ala Gly Asp Phe Val
1               5                   10                  15

Asn Met Val Glu
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Asn Asp Ser Gln Arg Gln Ala Thr Lys Asp Ala Gly Val Ile Ala Gly
1               5                   10                  15

Leu Asn Val Leu
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

<400> SEQUENCE: 28

Arg Thr Ala Leu Leu Asp Ala Ala Gly Val Ala Ser Leu Leu Thr Thr
1               5                   10                  15

Ala Glu Val Val
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Gly Leu Tyr His Cys Lys Pro Leu Val Asp Ile Leu Ile Leu Pro Gly
1               5                   10                  15

Tyr Val Gln Ala
        20

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Asn Asp Gln Gly Asn Arg Thr Thr Pro Ser Tyr Val Ala Phe Thr Asp
1               5                   10                  15

Thr Glu Arg Leu
        20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide

<400> SEQUENCE: 31

Ile Ser Ala Leu Phe Val Thr Pro Lys Thr Thr Gly Ala Arg Val Glu
1               5                   10                  15

Leu Ser Glu Gly
        20

<210> SEQ ID NO 32
<211> LENGTH: 21
<212> TYPE: PRT
<213> ORGANISM: Artificial Sequence
<220> FEATURE:
<223> OTHER INFORMATION: Synthetic peptide

<400> SEQUENCE: 32

Gln Ser Ile Val Pro Ala Leu Glu Ile Ala Asn Ala His Arg Lys Pro
1               5                   10                  15

Leu Val Ile Ile Ala
        20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Asn Glu Glu Ala Gly Asp Gly Thr Thr Thr Ala Thr Val Leu Ala Arg
1               5                   10                  15

Ser Ile Ala Lys
        20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Val Val Thr Cys Gly Tyr Thr Ile Pro Thr Cys Arg Lys Leu Asp Glu
1               5                   10                  15

```
Leu Gly Ser Lys
        20

<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Glu Gln Leu Asp Val Thr Thr Ser Glu Tyr Glu Lys Glu Lys Leu Asn
1               5                   10                  15

Glu Arg Leu Ala
        20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Ser Leu Phe Glu Gly Ile Asp Phe Tyr Thr Ser Ile Thr Arg Ala Arg
1               5                   10                  15

Phe Glu Glu Leu
        20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Asn Pro Val Glu Ile Arg Arg Gly Val Met Leu Ala Val Asp Ala Val
1               5                   10                  15

Ile Ala Glu Leu
        20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Gly Tyr Pro Val Thr Asn Ala Val Ile Thr Val Pro Ala Tyr Phe Asn
1               5                   10                  15

Asp Ser Gln Arg
        20

<210> SEQ ID NO 39
<211> LENGTH: 20
<212> TYPE: PRT
<213> ORGANISM: Artificial Sequence
<220> FEATURE:
<223> OTHER INFORMATION: Synthetic peptide

<400> SEQUENCE: 39

Val Ala Thr Ile Trp Phe Pro Val Cys Ala His Arg Glu Thr Thr Ile
```

-continued

```
1               5                   10                  15

Val Ser Phe Gly
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

Lys Gly Asp Lys Ala Gln Ile Glu Lys Arg Ile Gln Glu Ile Ile Glu
1               5                   10                  15

Gln Leu Asp Val
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

Lys Asp Asn Asn Leu Leu Gly Arg Phe Glu Leu Ser Gly Ile Pro Pro
1               5                   10                  15

Ala Pro Gly Val
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide

<400> SEQUENCE: 42

Thr Ile Asp Asp Gly Ile Phe Glu Val Lys Ala Thr Ala Gly Asp Thr
1               5                   10                  15

His Leu Gly Gly
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic peptide

<400> SEQUENCE: 43

Gln Asp Ala Tyr Val Leu Leu Ser Glu Lys Lys Ile Ser Ser Ile Gln
1               5                   10                  15

Ser Ile Val Pro
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic peptide

<400> SEQUENCE: 44
```

```
Leu Val Ile Ile Ala Glu Asp Val Asp Gly Glu Ala Leu Ser Thr Leu
1               5                   10                  15

Val Leu Asn Arg
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

<400> SEQUENCE: 45

Gly Tyr Val Gln Ala Cys Arg Ala Leu Met Ile Ala Ala Ser Val Leu
1               5                   10                  15

Gly Leu Pro Ala
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Gln Asp Val Leu Lys Lys Ser Tyr Ser Lys Ala Phe Thr Leu Thr Ile
1               5                   10                  15

Ser Ala Leu Phe
            20

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Gly Ser Gly Pro Thr Ile Glu Glu Val Asp
1               5                   10

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Arg Lys Gly Val Ile Thr Val Lys Asp Gly Lys Thr Leu Asn Asp Glu
1               5                   10                  15

Leu Glu Ile Ile
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Ser Gly Lys Ser Thr Leu Ala Arg Val Ile Val Asp Lys Tyr Arg Asp
1               5                   10                  15
```

```
Gly Thr Lys Met
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Leu Leu Ala Asp Ala Val Ala Val Thr Met Gly Pro Lys Gly Arg Thr
1               5                   10                  15

Val Ile Ile Glu
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide

<400> SEQUENCE: 51

Leu Ile Phe Asp Leu Gly Gly Gly Thr Phe Asp Val Ser Ile Leu Thr
1               5                   10                  15

Ile Asp Asp Gly
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Pro Gly Val Leu Ile Gln Val Tyr Glu Gly Glu Arg Ala Met Thr Lys
1               5                   10                  15

Asp Asn Asn Leu
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Glu Glu Ile Ala Gln Val Ala Thr Ile Ser Ala Asn Gly Asp Lys Glu
1               5                   10                  15

Ile Gly Asn Ile
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Asn Lys Arg Ala Val Arg Arg Leu Arg Thr Ala Cys Glu Arg Ala Lys
```

-continued

```
1               5                   10                  15

Arg Thr Leu Ser
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Tyr Phe Gly Lys Arg Pro Pro Gly Val Leu His Cys Thr Thr Lys Phe
1               5                   10                  15

Cys Asp Tyr Gly
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Arg Val Leu Ala Pro His Leu Thr Arg Ala Tyr Ala Lys Asp Val Lys
1               5                   10                  15

Phe Gly Ala Asp
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic peptide

<400> SEQUENCE: 57

Lys Ala Pro Gly Phe Gly Asp Asn Arg Lys Asn Gln Leu Lys Asp Met
1               5                   10                  15

Ala Ile Ala Thr
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Gly Ala Arg Gly Ala Phe Ser Glu Glu Tyr Lys Arg Leu Asp Glu Asp
1               5                   10                  15

Leu Ala Ala Tyr
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide

<400> SEQUENCE: 59
```

```
Ser Tyr Lys Gly Glu Thr Lys Ala Phe Tyr Pro Glu Glu Ile Ser Ser
1               5                   10                  15

Met Val Leu Thr
            20

<210> SEQ ID NO 60
<211> LENGTH: 16
<212> TYPE: PRT
<213> ORGANISM: Artificial Sequence
<220> FEATURE:
<223> OTHER INFORMATION: Synthetic peptide

<400> SEQUENCE: 60

Thr Gln Gly Ser Arg Lys Gly Gly Ala Leu Gln Ser Cys Thr Ile Ile
1               5                   10                  15

<210> SEQ ID NO 61
<211> LENGTH: 20
<212> TYPE: PRT
<213> ORGANISM: Artificial Sequence
<220> FEATURE:
<223> OTHER INFORMATION: Synthetic peptide

<400> SEQUENCE: 61

Val Thr Asp Ala Leu Asn Ala Thr Arg Ala Ala Val Glu Glu Gly Ile
1               5                   10                  15

Val Leu Gly Gly
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic peptide

<400> SEQUENCE: 62

Thr Val Ile Ile Glu Gln Ser Trp Gly Ser Pro Lys Val Thr Lys Asp
1               5                   10                  15

Gly Val Thr Val
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide

<400> SEQUENCE: 63

Val Asn Met Val Glu Lys Gly Ile Ile Asp Pro Thr Lys Val Val Arg
1               5                   10                  15

Thr Ala Leu Leu
            20

<210> SEQ ID NO 64
<211> LENGTH: 20
<212> TYPE: PRT
<213> ORGANISM: Artificial Sequence
<220> FEATURE:
<223> OTHER INFORMATION: Synthetic peptide

<400> SEQUENCE: 64

Ala Gly Gly Val Met Thr Ala Leu Ile Lys Arg Asn Ser Thr Ile Pro
1               5                   10                  15
```

```
Thr Lys Gln Thr
        20

<210> SEQ ID NO 65
<211> LENGTH: 20
<212> TYPE: PRT
<213> ORGANISM: Artificial Sequence
<220> FEATURE:
<223> OTHER INFORMATION: Synthetic peptide

<400> SEQUENCE: 65

Pro Val Glu Lys Ala Leu Arg Asp Ala Lys Leu Asp Lys Ala Gln Ile
1               5                  10                  15

His Asp Leu Val
        20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide

<400> SEQUENCE: 66

Ser Pro Tyr Phe Ile Asn Thr Ser Lys Gly Gln Lys Cys Glu Phe Gln
1               5                  10                  15

Asp Ala Tyr Val
        20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide

<400> SEQUENCE: 67

Asp Gly Val Thr Val Ala Lys Ser Ile Asp Leu Lys Asp Lys Tyr Lys
1               5                  10                  15

Asn Ile Gly Ala
        20

<210> SEQ ID NO 68
<211> LENGTH: 20
<212> TYPE: PRT
<213> ORGANISM: Artificial Sequence
<220> FEATURE:
<223> OTHER INFORMATION: Synthetic peptide

<400> SEQUENCE: 68

Pro Ala Pro Gly Val Pro Gln Ile Glu Val Thr Phe Asp Ile Asp Ala
1               5                  10                  15

Asn Gly Ile Leu
        20

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide

<400> SEQUENCE: 69

Met Asn Arg Gly Phe Ser Arg Lys Ser His Thr Phe Leu Pro Lys Ile
```

```
                   1               5                  10                 15

Phe Phe Arg Lys
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide

<400> SEQUENCE: 70

Gly Leu Asn Val Leu Arg Ile Ile Asn Glu Pro Thr Ala Ala Ala Ile
1               5                   10                  15

Ala Tyr Gly Leu
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide

<400> SEQUENCE: 71

Ser Met Val Leu Thr Lys Met Lys Glu Ile Ala Glu Ala Tyr Leu Gly
1               5                   10                  15

Tyr Pro Val Thr
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide

<400> SEQUENCE: 72

Glu Leu Ser Glu Gln Gln Leu Gln Leu Trp Pro Ser Asp Val Asp Lys
1               5                   10                  15

Leu Ser Pro Thr
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide

<400> SEQUENCE: 73

Met Ala Lys Ala Ala Ala Val Gly Ile Asp Leu Gly Thr Thr Tyr Ser
1               5                   10                  15

Cys Val Gly Val
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide

<400> SEQUENCE: 74
```

```
Lys Ala Asn Lys Ile Thr Ile Thr Asn Asp Lys Gly Arg Leu Ser Lys
1               5                   10                  15

Glu Glu Ile Glu
            20

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide

<400> SEQUENCE: 75

Ile Phe Phe Arg Lys Met Ser Ser Ser Gly Ala Lys Asp Lys Pro Glu
1               5                   10                  15

Leu Gln Phe Pro
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic peptide

<400> SEQUENCE: 76

Asp Gly Thr Lys Met Val Ser Ala Asp Ala Tyr Lys Ile Thr Pro Gly
1               5                   10                  15

Ala Arg Gly Ala
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic peptide

<400> SEQUENCE: 77

Gly Glu Val Ile Val Thr Lys Asp Asp Ala Met Leu Leu Lys Gly Lys
1               5                   10                  15

Gly Asp Lys Ala
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide

<400> SEQUENCE: 78

Val Ile Ala Glu Leu Lys Lys Gln Ser Lys Pro Val Thr Thr Pro Glu
1               5                   10                  15

Glu Ile Ala Gln
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic peptide

<400> SEQUENCE: 79
```

```
Gln Ala Ala Ile Leu Met Gly Asp Lys Ser Glu Asn Val Gln Asp Leu
1               5                   10                  15

Leu Leu Leu Asp
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide

<400> SEQUENCE: 80

Gly Leu Lys Gly Lys Ile Ser Glu Ala Asp Lys Lys Val Leu Asp
1               5                   10                  15

Lys Cys Gln Glu
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic peptide

<400> SEQUENCE: 81

Arg Ala Ile Phe Thr Gly Tyr Tyr Gly Lys Gly Lys Pro Val Pro Thr
1               5                   10                  15

Gln Gly Ser Arg
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide

<400> SEQUENCE: 82

Pro Gly Pro Gly Gly Phe Gly Ala Gln Gly Pro Lys Gly Gly Ser Gly
1               5                   10                  15

Ser Gly Pro Thr
            20

<210> SEQ ID NO 83
<211> LENGTH: 18
<212> TYPE: PRT
<213> ORGANISM: Artificial Sequence
<220> FEATURE:
<223> OTHER INFORMATION: Synthetic peptide

<400> SEQUENCE: 83

Pro Gly Met Gly Ala Met Gly Gly Met Gly Gly Gly Met Gly Gly
1               5                   10                  15

Met Phe

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide

<400> SEQUENCE: 84
```

```
Ser Cys Val Gly Val Phe Gln His Gly Lys Val Glu Ile Ile Ala Asn
1               5                   10                  15

Asp Gln Gly Asn
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptide

<400> SEQUENCE: 85

Met Val Ala Thr Cys Leu Gln Val Val Gly Phe Val Thr Ser Phe Val
1               5                   10                  15

Gly Trp Ile Gly
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic peptide

<400> SEQUENCE: 86

Gly Glu Glu Val Gly Glu Leu Ser Arg Gly Lys Leu Tyr Ser Leu Gly
1               5                   10                  15

Asn Gly Arg Trp
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic peptide

<400> SEQUENCE: 87

Leu Asp Leu Leu Glu Ile Leu Arg Gln Glu Lys Gly Gly Ser Arg Gly
1               5                   10                  15

Glu Glu Val Gly
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic peptide

<400> SEQUENCE: 88

Val Cys Asn Pro Ile Ile Ser Gly Leu Tyr Gln Gly Ala Gly Gly Pro
1               5                   10                  15

Gly Pro Gly Gly
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 89

Glu Leu Glu Ile Ile Glu Gly Met Lys Phe Asp Arg Gly Tyr Ile Ser
1               5                   10                  15

Pro Tyr Phe Ile
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide

<400> SEQUENCE: 90

Leu Asp Ser Leu Thr Pro Ala Asn Glu Asp Gln Lys Ile Gly Ile Glu
1               5                   10                  15

Ile Ile Lys Arg
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide

<400> SEQUENCE: 91

Lys Lys Ser Ser Glu Thr Leu Arg Lys Ala Gly Gln Val Phe Leu Glu
1               5                   10                  15

Glu Leu Gly Asn
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic peptide

<400> SEQUENCE: 92

Leu Glu Lys Asp Phe Leu Pro Leu Tyr Phe Gly Trp Phe Leu Thr Lys
1               5                   10                  15

Lys Ser Ser Glu
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide

<400> SEQUENCE: 93

Leu Asp Asp Thr Asn His Glu Arg Glu Arg Leu Glu Gln Leu Phe Glu
1               5                   10                  15

Met Ala Asp Gln
            20

<210> SEQ ID NO 94
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 94

Gln Leu Ala Gly Val Leu Leu Ile Leu Leu Ala Leu Cys Ala Leu Val
1               5                   10                  15

Ala Thr Ile Trp
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic peptide

<400> SEQUENCE: 95

Pro Thr Lys Gln Thr Gln Ile Phe Thr Thr Tyr Ser Asp Asn Gln Pro
1               5                   10                  15

Gly Val Leu Ile
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptide

<400> SEQUENCE: 96

Ile His Asp Leu Val Leu Val Gly Gly Ser Thr Arg Ile Pro Lys Val
1               5                   10                  15

Gln Lys Leu Leu
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide

<400> SEQUENCE: 97

Val Leu Cys Leu Val Gly Gly Cys Val Ile Leu Cys Cys Ala Gly Asp
1               5                   10                  15

Ala Gln Ala Phe
            20

<210> SEQ ID NO 98
<211> LENGTH: 11
<212> TYPE: PRT
<213> ORGANISM: Artificial Sequence
<220> FEATURE:
<223> OTHER INFORMATION: Synthetic peptide

<400> SEQUENCE: 98

Tyr Glu Val His His Gln Lys Leu Val Phe Phe
1               5                   10

<210> SEQ ID NO 99
<211> LENGTH: 42
<212> TYPE: PRT
<213> ORGANISM: Artificial Sequence
<220> FEATURE:
<223> OTHER INFORMATION: Synthetic peptide

<400> SEQUENCE: 99
```

-continued

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 100
<211> LENGTH: 12
<212> TYPE: PRT
<213> ORGANISM: Artificial Sequence
<220> FEATURE:
<223> OTHER INFORMATION: Synthetic peptide

<400> SEQUENCE: 100

Asp Ala Glu Phe Arg His Asp Ser Gly Tyr Glu Val
1               5                   10

<210> SEQ ID NO 101
<211> LENGTH: 40
<212> TYPE: PRT
<213> ORGANISM: Artificial Sequence
<220> FEATURE:
<223> OTHER INFORMATION: Synthetic peptide

<400> SEQUENCE: 101

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 102
<211> LENGTH: 23
<212> TYPE: PRT
<213> ORGANISM: Artificial Sequence
<220> FEATURE:
<223> OTHER INFORMATION: Synthetic peptide

<400> SEQUENCE: 102

Asp Ala Glu Phe Arg His Asp Ser Gly Tyr Glu Val His His Gln Lys
1               5                   10                  15

Leu Val Phe Phe Ala Glu Asp
            20

<210> SEQ ID NO 103
<211> LENGTH: 24
<212> TYPE: PRT
<213> ORGANISM: Artificial Sequence
<220> FEATURE:
<223> OTHER INFORMATION: Synthetic peptide

<400> SEQUENCE: 103

Leu Val Phe Phe Ala Glu Asp Val Gly Ser Asn Lys Gly Ala Ile Ile
1               5                   10                  15

Gly Leu Met Val Gly Gly Val Val
            20